(12) United States Patent
Yousaf

(10) Patent No.: US 10,017,460 B2
(45) Date of Patent: Jul. 10, 2018

(54) COMPOUNDS FOR PROMOTING LIPOSOMAL AND CELLULAR ADHESION AND COMPOSITIONS AND METHODS OF USE THEREOF

(71) Applicant: Muhammad Naveed Yousaf, Mississauga (CA)

(72) Inventor: Muhammad Naveed Yousaf, Mississauga (CA)

(73) Assignee: ORGANOLINX CORP., Mississauga (CA)

( * ) Notice: Subject to any disclaimer, the term of this patent is extended or adjusted under 35 U.S.C. 154(b) by 0 days.

(21) Appl. No.: 14/896,069

(22) PCT Filed: Jun. 11, 2014

(86) PCT No.: PCT/CA2014/050547
§ 371 (c)(1),
(2) Date: Dec. 4, 2015

(87) PCT Pub. No.: WO2014/197991
PCT Pub. Date: Dec. 18, 2014

(65) Prior Publication Data
US 2016/0130216 A1    May 12, 2016

Related U.S. Application Data

(60) Provisional application No. 61/834,176, filed on Jun. 12, 2013.

(51) Int. Cl.
| | | |
|---|---|---|
| *A61K 9/127* | (2006.01) | |
| *C07C 235/20* | (2006.01) | |
| *C12N 5/00* | (2006.01) | |
| *C07F 9/50* | (2006.01) | |
| *C07C 43/14* | (2006.01) | |
| *C07C 217/08* | (2006.01) | |
| *C07C 323/12* | (2006.01) | |
| *C07C 239/20* | (2006.01) | |
| *C07C 243/14* | (2006.01) | |
| *C07C 247/04* | (2006.01) | |
| *C07D 495/04* | (2006.01) | |
| *C07D 207/46* | (2006.01) | |
| *C07C 50/28* | (2006.01) | |
| *C07D 307/60* | (2006.01) | |
| *C07F 9/40* | (2006.01) | |
| *C07C 43/172* | (2006.01) | |
| *C07C 49/175* | (2006.01) | |
| *C12N 15/88* | (2006.01) | |

(52) U.S. Cl.
CPC ............ *C07C 235/20* (2013.01); *A61K 9/127* (2013.01); *C07C 43/14* (2013.01); *C07C 43/172* (2013.01); *C07C 49/175* (2013.01); *C07C 50/28* (2013.01); *C07C 217/08* (2013.01); *C07C 239/20* (2013.01); *C07C 243/14* (2013.01); *C07C 247/04* (2013.01); *C07C 323/12* (2013.01); *C07D 207/46* (2013.01); *C07D 307/60* (2013.01); *C07D 495/04* (2013.01); *C07F 9/4084* (2013.01); *C07F 9/5022* (2013.01); *C12N 5/0006* (2013.01); *C12N 15/88* (2013.01); *C07C 2601/10* (2017.05)

(58) Field of Classification Search
CPC .. A61K 9/127; C07C 2101/10; C07C 217/08; C07C 235/20; C07C 239/20; C07C 243/14; C07C 247/04; C07C 323/12; C07C 43/14; C07C 43/172; C07C 49/175; C07C 50/28; C07C 207/46; C07C 307/60
USPC ................................. 424/450; 435/375, 458
See application file for complete search history.

(56) References Cited

U.S. PATENT DOCUMENTS

| | | | |
|---|---|---|---|
| 4,861,597 | A | 8/1989 | Kida et al. |
| 6,417,326 | B1 | 7/2002 | Cullis et al. |
| 9,080,144 | B2 | 7/2015 | Yousaf |
| 2007/0249060 | A1 | 10/2007 | Kirschner et al. |
| 2010/0063135 | A1 | 3/2010 | Dande et al. |
| 2012/0100077 | A1 | 4/2012 | Hoffmann et al. |
| 2013/0302891 | A1 | 11/2013 | Yousaf |

FOREIGN PATENT DOCUMENTS

| | | |
|---|---|---|
| CN | 102051239 A1 | 5/2011 |
| WO | 2013/173392 A1 | 11/2013 |

OTHER PUBLICATIONS

Dutta et al. (Bioconjugate Chemistry, 2011, 22:8704-8713; reference cited in IDS).*
Holland et al. Biochemistry, 1996, 35(8), 2618-2624.*
Selden et al. JACS 2012, 134(2), 765-768.*
Alberts_2002_Lipid bilayers_https___www.ncbi.nlm.nih.*
Karlberg et al. Contact Dermatitis 2003: 49: 241-247.*
STN International Search—dated Dec. 10, 2014.
International Search Report and Written Opinion of PCT/CA2014/050547 dated Sep. 29, 2014.
Dutta et al., Synthetic Chemoselective Rewiring of Cell Surfaces: Generation of Three-Dimensional Tissue Structures, J. Am. Chem. Soc., 2011, 133 (22), 8704-8713.
Dutta et al., "Engineering Cell Surfaces via Liposome Fusion", Bioconjugate Chem., 2011, 22 (12), 2423-2433.
Selden, Nicholas et al., "Chemically Programmed Cell Adhesion with Membrane-Anchored Oligonucleotides", J. Am. Chem. Soc., 2012, 134(2), 765-768.

(Continued)

*Primary Examiner* — Janet L Epps-Smith
(74) *Attorney, Agent, or Firm* — Bereskin & Parr LLP/S.E.N.C.R.L. s.r.l.; Patricia Folkins

(57) ABSTRACT

The present application describes amphiphatic compounds like compound IIa below, compositions and methods for incorporating chemoselective and bio-orthogonal complementary functional groups into liposomes. Such compounds are incorporated in greater numbers in liposome and fused cell surfaces, leading to greater adhesion and conjugation efficiency. The present application also describes various uses of these modified liposomes including for tethering the chemoselective and bioorthogonal complementary functional groups from cell surfaces by liposome delivery toward the goal of rewiring the cell surface.

22 Claims, 27 Drawing Sheets

(56) References Cited

OTHER PUBLICATIONS

Wilson, J.T. et al., "Noncovalent Cell Surface Engineering with Cationic Graft Copolymers", J. Am. Chem. Soc., 2009, 131 (51), 18228-18229.

Gong, Yun et al., "Membrane Activation: Selective Vesicle Fusion via Small Molecule Recognition", J. Am. Chem. Soc., 2006, 128 (45), 14430-14431.

Holland, JW et al., "Poly(ethylene glycol)—Lipid Conjugates Regulate the Calcium-Induced Fusion of Liposomes Composed of Phosphatidylethanolamine and Phosphatidylserine", Biochemistry., 1996, 35(8), 2618-2624.

Faiss, Simon et al., "Adhesion and rupture of liposomes mediated by electrostatic interaction monitored by thickness shear mode resonators" Eur Biophys J (2004) 33, 551-561.

\* cited by examiner

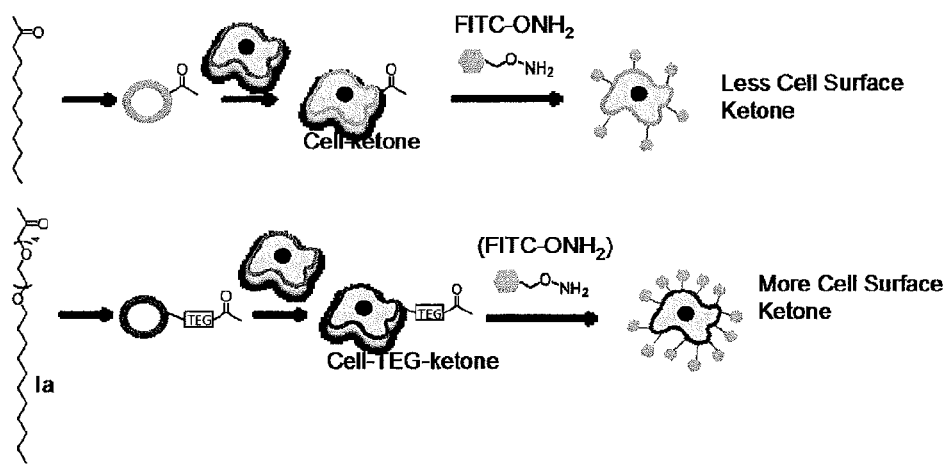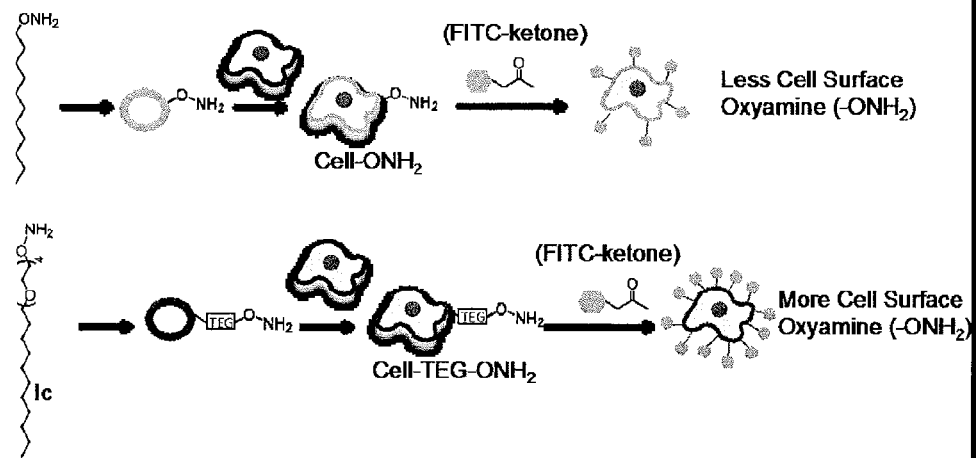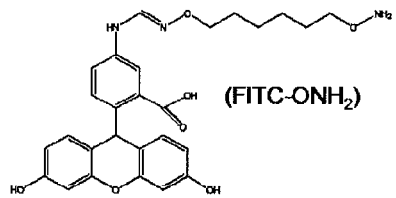
Figure 1

Cell Viability

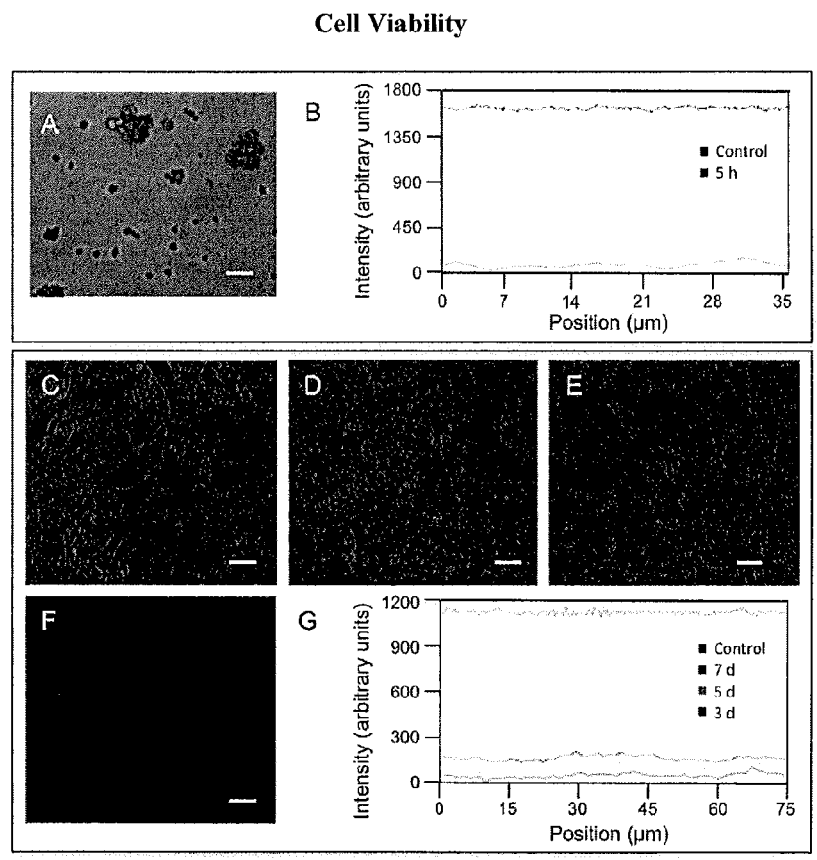

3D spheroid and multi-layer structure cell viability, assayed with trypan blue. (A) Ketone- and oxyamine presenting swiss 3T3 albino fibroblasts were mixed together in solution for 1, 2, 3, and 5 h, resulting in 3D spheroid formation and were then tested for viability using trypan blue dye (0.4 % in PBS, 2 min). (B) Trypan blue linescans (fluorescence false-colored for enhanced visualization) of the spheroids generated after 5 h of culture were compared to a control population in which spheroids were generated for 5 h, fixed with formaldehyde, and stained with trypan blue under the same conditions. Greater than 99 % of cells were determined to be viable. Similarly, 3D multi-layered tissue-like structures were generated and cultured for (C) 3 (D) 5, and (E) 7 days and tested for viability using trypan blue dye. (F) Again as a control, cells were grown in a multilayer for 7 days, then fixed with formaldehyde, and stained with trypan blue, and linescans were constructed for all samples and compared to the control. Cell viability decreased with time and number of cell layers from 3 to 5 to 7 days of culture with approximated viabilities of (C) 98, (D) 91, and (E) 84 %, respectively. The scale bars represent 60 (A) and 30 μm (C-F).

COMPOUNDS FOR PROMOTING LIPOSOMAL AND CELLULAR ADHESION AND COMPOSITIONS AND METHODS OF USE THEREOF

This application is a National Stage of co-pending International Application No. PCT/CA2014/050547 filed Jun. 11, 2014, which claims the benefit of Provisional Application No. 61/834,176, filed Jun. 12, 2013, the contents of both of which are herein incorporated in their entirety by reference.

The present application relates to compounds containing complementary, bio-orthogonal functional groups and to their incorporation into liposomes and the use of the resulting liposomes for promoting liposomal and cellular adhesion.

BACKGROUND OF THE APPLICATION

Cells that make up tissues and organs exist and communicate within a complex, three-dimensional (3D) environment. The spatial orientation and distribution of extracellular matrix (ECM) components directly influences the manner in which cells receive, integrate, and respond to a range of input signals.[1] As such, cellular interactions with ECM molecules and/or other cells have been extensively investigated for fundamental studies in development, cell motility, differentiation, apoptosis, paracrine signaling, and applications in tissue engineering.[2,3] There has been tremendous effort toward the design and fabrication of 3D scaffolds that mimic ECM properties and induce tissue formation in vitro, utilizing various biomaterials, biodegradable polymers,[4] collagen,[5] and hydrogels.[6,7] Among the major challenges facing the use of these technologies for tissue engineering are the abilities to force contact between multiple cell types in 3D to control the spatial and temporal arrangement of cellular interactions and tailor and mold the biomaterial to recapitulate the 3D, in vivo environment under laboratory constraints. Without the use of engineered scaffolds in culture, most cells are unable to form the necessary higher-order 3D structure required for the anatomical mimicry of tissue and are limited to random migration, generating two-dimensional (2D) monolayers. As a result, several approaches, including the use of dielectrophoretic forces,[8,9] laser-guided writing,[10-12] surface manipulation,[13] and a number of lithographic printing techniques[14-17] have been integrated with 3D scaffold designs to produce multi-type cellular arrays[9,11,17,18] or 3D cell clusters or spheroids.[7,8,13] In a recent study, 3D aggregates consisting of multiple cell types were formed within a hydrogel matrix through DNA hybridization after cell surfaces were engineered with complementary short oligonucleotides via a metabolic labeling approach.[7] However, for some applications, the presentation of cell-surface DNA may not be stable for extended time periods in cell culture or in vivo.

Cell-surface engineering methodologies have primarily been of interest in molecular biology. As such, biosynthetic approaches have been employed to introduce different functional groups on cell surfaces. In a pioneering study, an unnatural derivative of N-acetyl-mannosamine, which bears a ketone group, was converted to the corresponding sialic acid and metabolically incorporated onto cell-surface oligosaccharides, resulting in the cell surface display of ketone groups.[19] However, metabolic or genetic methods may alter many of the biochemical pathways required for normal cell function and not all cell lines possess this metabolic machinery. Thus, there is a growing demand for general tools that can provide simple alternatives to the complex genetic and biosynthetic methods. Other approaches to cell-surface engineering have also been undertaken to incorporate a functional group into a target biomolecule, such as an endogenous protein, utilizing a cell's biosynthetic machinery.[20,21] These strategies aim to produce a site that can then be covalently modified with its delivered counterpart or probe. However, most of these protein-based tags are large and bulky and become problematic when interacting with the other glycans and biomolecules on the cell suface.[22,23] Additionally, the perturbation of cellular physiology with biomolecules at the cell surface may result in the interference of significant biochemical pathways or cellular functions.[24,25].

Membrane fusion processes are ubiquitous in biology and span multi-cellular communication, extracellular signaling, the reconstruction of damaged organelles, and integration of cells into complex tissues and organs.[26] As a result, there has been much interest in developing model systems to mimic biological membranes to investigate the mechanisms of fusion and for use in various biotechnological applications. For example, cells secrete and display proteins and lipids during vesicle trafficking events that either diffuse into the ECM or become components of the cell membrane after fusion.[27] Naturally, lipid vesicles provide an ideal platform for such studies and have been widely used to examine various membrane-related processes, including fusion.[26-30] In order for fusion to occur, the membranes must be brought into close proximity, followed by bilayer destabilization.[31] Fusion of such lipid vesicles or liposomes can be initiated by using divalent cations, polycations,[32] positively charged amino acids[33] and membrane-disrupting peptides.[34,35] Historically, synthetic chemical agents have also been employed to fuse vesicle membranes[36-39] through non-specific interactions. However, recent efforts to improve selectivity and control over vesicle fusion have been achieved through the use of small, synthetic molecular recognition pairs.[40-41] Since vesicle fusion is a natural process and has been shown to influence the construction of cells into multicellular organisms, much research has focused on using liposomes to deliver cargoes, reagents, nanomaterials, and therapeutic agents to cells.

Noncovalent cell-surface engineering strategies via cationic graft copolymer adsorption and a fluorescent cell labeling technique via cationic and aromatic lipid fusion have been previously reported.[42]

The incorporation of chemoselective and bio-orthogonal complementary ketone and oxyamine groups into separate liposomes, which when mixed, resulted in chemical recognition, producing stable oxime bonds under physiological conditions has been reported.[54-66] The liposomes combined in this manner reacted chemoselectively to form an interfacial, covalent oxime linkage, resulting in liposome docking and adhesion. Adhered liposomes either fused or formed multiadherent structures. These liposomes comprising ketone and oxyamine groups were also cultured with various cell types resulting in membrane fusion and the display of ketones and oxyamines on the cell surface in a manner such that they were available for further chemical manipulation.[54-55]

SUMMARY OF THE APPLICATION

The present application describes compounds useful for incorporating chemoselective and bio-orthogonal complementary functional groups, such as ketone and oxyamine groups, and aldehyde and amine groups, into liposomes. In one embodiment, the compounds of the application are amphiphatic molecules comprising a lipophilic portion, a hydrophilic portion and a functional group, wherein the functional group is bonded, optionally through a linker group, to the hydrophilic portion and is one of a complementary functional group pair. The presence of the hydrophilic portion in the amphiphatic molecules results in a greater amount of the amphiphatic molecules remaining at the surface of the liposome compared to amphiphatic molecules that do not contain this portion. This allows for greater numbers of functional groups to be at the surface of the liposome, available for chemical reaction, and therefore enhances the efficiency of, for example, fusion of liposomes comprising the compounds of the application.

In an embodiment, the compounds of the present application are compounds of Formula I:

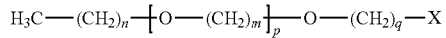
(I)

wherein:
n is 5, 6, 7, 8, 9, 10, 11, 12, 13, 14, 15, 16, 17, 18, 19, 20, 21, 22, 23, 24, 25, 26, 27, 28 or 29;
m is 1, 2, 3, or 4;
p is 1, 2, 3, 4, 5, 6, 7, 8, 9 or 10;
q is 0, 1, 2, 3, 4, 5 or 6; and
X is one of a complementary functional group pair.

In an embodiment of the application, the compounds of the application further comprise at least one of a fluorescent moiety, an electroactive moiety, a photocleavable moiety, a radioactive moiety, a chelating moiety and a spin label. These moieties are bonded to any available node on the compounds of the application. For example, in an embodiment, the fluorescent moiety, electroactive moiety, photocleavable moiety, radioactive moiety, chelating moiety and/or spin label is located between the lipophilic portion and the hydrophilic portion. Alternatively, in a further embodiment the fluorescent moiety, electroactive moiety, photocleavable moiety, radioactive moiety, chelating moiety and/or spin label is located between the hydrophilic portion and the functional group.

In an embodiment, the compounds of the present application comprising a fluorescent moiety, an electroactive moiety and/or a photocleavable moiety are compounds of Formula II:

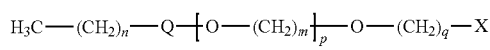
(II)

wherein:
n is 5, 6, 7, 8, 9, 10, 11, 12, 13, 14, 15, 16, 17, 18, 19, 20, 21, 22, 23, 24, 25, 26, 27, 28 or 29;
m is 1, 2, 3, or 4;
p is 1, 2, 3, 4, 5, 6, 7, 8, 9 or 10;
q is 0, 1, 2, 3, 4, 5 or 6;
Q comprises at least one of a fluorescent moiety, an electroactive moiety, a photocleavable moiety, a radioactive moiety, a chelating moiety and a spin label; and
X is one of a complementary functional group pair.

In another embodiment, the compounds of the present application comprising a fluorescent moiety, an electroactive moiety and/or a photocleavable moiety are compounds of Formula III:

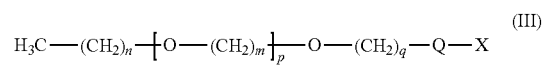
(III)

wherein:
n is 5, 6, 7, 8, 9, 10, 11, 12, 13, 14, 15, 16, 17, 18, 19, 20, 21, 22, 23, 24, 25, 26, 27, 28 or 29;
m is 1, 2, 3, or 4;
p is 1, 2, 3, 4, 5, 6, 7, 8, 9 or 10;
q is 0, 1, 2, 3, 4, 5 or 6;
Q comprises at least one of a fluorescent moiety, an electroactive moiety, a photocleavable moiety, a radioactive moiety, a chelating moiety and a spin label; and
X is one of a complementary functional group pair.

Accordingly, in combination, the present application includes a compound of the Formula IV:

R—X    (IV)

wherein R is selected from:

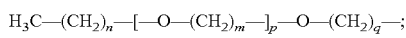

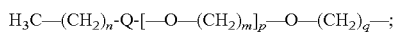

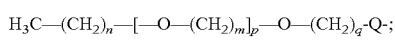

n is 5, 6, 7, 8, 9, 10, 11, 12, 13, 14, 15, 16, 17, 18, 19, 20, 21, 22, 23, 24, 25, 26, 27, 28 or 29;
m is 1, 2, 3, or 4;
p is 1, 2, 3, 4, 5, 6, 7, 8, 9 or 10;
q is 0, 1, 2, 3, 4, 5 or 6;
Q comprises at least one of a fluorescent moiety, an electroactive moiety, a photocleavable moiety, a radioactive moiety, a chelating moiety and a spin label; and
X is one of a complementary functional group pair.

The present application also includes a compound of the Formula V:

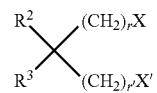
(V)

wherein $R^2$ and $R^3$ are each, independently selected from

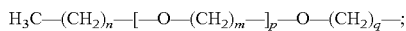

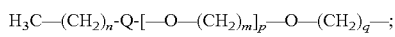

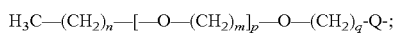

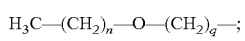

n is 5, 6, 7, 8, 9, 10, 11, 12, 13, 14, 15, 16, 17, 18, 19, 20, 21, 22, 23, 24, 25, 26, 27, 28 or 29;
m is 1, 2, 3, or 4;
p is 1, 2, 3, 4, 5, 6, 7, 8, 9 or 10;
q is 0, 1, 2, 3 or 46;
Q comprises at least one of a fluorescent moiety, an electroactive moiety, a photocleavable moiety, a radioactive moiety, a chelating moiety and a spin label; r and r' are each independently, 1, 2 or 3; and
X and X' are each, independently, one of a complementary functional group pair.

The present application also includes a liposome comprising amphiphatic molecules, wherein the amphiphatic molecules comprise a lipophilic portion, a hydrophilic portion and a functional group, and the functional group is bonded to the hydrophilic portion and is one of a functional group pair. In an embodiment of the application, the amphiphatic molecules are selected from one or more of a compound of Formula I, II and Formula III. In another embodiment of the application, the amphiphatic molecules are selected from one or more of a compound of Formula IV. In another embodiment of the application, the amphiphatic molecules are selected from one or more of a compound of Formula V.

In one embodiment of the present application, amphiphatic molecules comprising complementary functional group pairs are inserted into separate liposomes. When these two types of liposomes are mixed, chemical recognition occurs, producing stable bonds between the complementary functional group pairs. The liposomes combined in this manner react chemoselectively to form an interfacial, chemical interaction, resulting in liposome docking and adhesion. Adhered liposomes either fuse or form multiadherent structures.

Accordingly, the present application also includes a mixture comprising a plurality of liposomes of type A and a plurality of liposomes of type B, wherein the liposomes of type A comprise a compound of the application having a functional group that is complementary to a functional group on compounds of the application comprised in the liposomes of type B to form a chemical interaction that results in adhesion of the liposomes of type A and the liposomes of type B.

In an embodiment of the application, the adhesion of the liposomes of type A and the liposomes of type B results in formation of multiadherant liposomes, the partial fusion of liposomes of type A and the liposomes of type B and/or the complete fusion of the liposomes of type A and type B.

It is an embodiment of the application that the complementary functional group pairs are bio-orthogonal. In a further embodiment of the application, the complementary functional group pair is a ketone and an oxyamine which when contacted with each other, form a stable oxime bond. Accordingly, in an embodiment of the application, X in the compounds of Formula I, II, and III is, independently, $C(O)R^1$, wherein $R^1$ is $C_{1-2}$alkyl, or X in the compounds of Formula I, II, and III is O—$NH_2$. In another embodiment of the application, X in the compounds of Formula IV is $C(O)R^{1'}$ wherein $R^1$ is $C_{1-2}$alkyl, or X in the compounds of Formula IV is O—$NH_2$. In another embodiment of the application, X and X' in the compounds of Formula V are both $C(O)R^1$, wherein $R^1$ is $C_{1-2}$alkyl, or X and X' in the compounds of Formula V are both O—$NH_2$.

In a further embodiment of the application, the complementary functional group pair is a aldehyde and an amine which when contacted with each other, form a stable imine bond. Accordingly, in an embodiment of the application, X in the compounds of Formula I, II and III is, independently, C(O)H or X in the compounds of Formula I, II and III is $NH_2$. In another embodiment of the application, X and X' in the compounds of Formula V are both C(O)H or X and X' in the compounds of Formula V are both $NH_2$.

In an embodiment of the application, aside from the compounds of the application, the liposomes further comprise any suitable amphipatic molecule, or mixture of molecules, that form liposomes. In general, liposome-forming amphiphatic molecules are lipids, in particular phospholipids. In a further embodiment, the amphiphatic molecules are selected based on the proposed use of the liposome.

In yet another embodiment, the liposomes further comprise other functional molecules, such as, fluorescent molecules, dyes and/or other indicator molecules, so that when the liposomes of type A and type B are fused, a physical change, such as a change in fluorescence, color or smell, occurs.

In yet another embodiment, the liposomes of the present application further comprise a nucleic acid molecule complexed with the liposomes.

In a further embodiment of the application, the liposomes further comprise biologically active agents, such as nucleic acids, proteins, peptides, small molecule drugs, carbohydrates and the like, and mixtures thereof, and fusion of the liposomes with any cell population results in the simultaneous delivery of the biological agents into the cells and modification of the cell's surface with at least one of a complementary functional group pair. The biologically active agents may be entrapped within the liposome or may be incorporated into the liposome membrane.

The present application also includes a method for promoting adhesion of liposomes comprising contacting a plurality of liposomes of type A with a plurality of liposomes of type B, wherein the liposomes of type A comprise a compound of the application having a functional group that is complementary to a functional group on compounds of the application comprised in the liposomes of type B to form a chemical interaction that results in adhesion of the liposomes of type A and the liposomes of type B.

The presence of amphiphatic molecules comprising at least one of a fluorescent moiety, an electroactive moiety and a photocleavable moiety allows for further manipulation and monitoring of the fusion of liposomes.

The present application also describes compounds, compositions and methods for tethering chemoselective and bio-orthogonal complementary functional groups, such as ketone and oxyamine groups or aldehyde and amine groups, from cell surfaces by liposome delivery, toward the goal of rewiring the cell's surface. In one embodiment, the liposomes described above comprising at least one of a complementary functional group pair are cultured with various cell types resulting in liposome membrane fusion and the display of the complementary functional group on the cell surface in a manner such it is available for further chemical manipulation. Therefore the synthetic functional groups fused on the cell membrane serve as cell-surface receptors, providing tools for the attachment of other functional materials, biomolecules, and probes on the cell surface. In sum, liposome fusion to cell membranes is employed herein as a method to deliver small chemical functional groups to tailor the cell membrane for subsequent bio-orthogonal and chemoselective ligation reactions and further manipulations as described hereinbelow.

In yet another embodiment, the liposomes are combined with one or more nucleic acid molecules to form a nucleic acid-liposome complex. These complexes, when delivered to cells result in simultaneous transfection of the cells with the nucleic acid molecule(s) and modification of the cell's surface with at least one of a complementary functional group pair. The transfected and cell surface modified cells can then undergo subsequent cell-cell assembly or reaction, for example, with a range of ligands, small molecules and proteins via bio-orthogonal ligation.

Accordingly, the present application includes a method of modifying a cell membrane comprising contacting the cell with a liposome comprising one of more compounds of the application under conditions for incorporation of the compounds into the cell membrane.

The present application also includes the use of one or more compounds of the application, or liposomes comprising one or more of the compounds of the application, for modifying a cell membrane.

In another embodiment, the present application includes a method for promoting the adhesion of cells comprising:
(a) contacting a first cell population with a liposome of type A under conditions for the fusion of the liposome of type A with the first cell population;
(b) contacting a second cell population with a liposome of type B under conditions for the fusion of the liposome of type B with the second cell population; and
(c) contacting the fused first cell population with the fused second cell population,
wherein the liposomes of type A comprise a functional group that reacts with a functional group comprised in the liposomes of type B to form a chemical interaction that results in the adhesion of the first and second cell populations.

The present application also includes a method for the simultaneous transfection of one or more nucleic acid molecules into a cell and modification of the cell's membrane comprising:
(a) combining the one or more nucleic acid molecules with a liposome under conditions to form a liposome-nucleic acid complex wherein the liposome comprises one or more amphiphatic molecules; and
(b) contacting the cell with the liposome-nucleic acid complex under conditions to simultaneously transfect the cell with the one or more nucleic acid molecules and incorporate the one or more compounds into the cell membrane,
wherein the one or more amphiphatic molecules are selected from a compound of Formula V as defined above and a compound of Formula VI:

$$R^4 - X \tag{VI}$$

wherein $R^4$ is selected from:

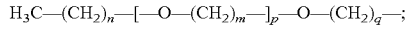

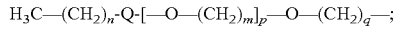

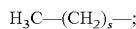

n is 5, 6, 7, 8, 9, 10, 11, 12, 13, 14, 15, 16, 17, 18, 19, 20, 21, 22, 23, 24, 25, 26, 27, 28 or 29;
m is 1, 2, 3, or 4;
p is 1, 2, 3, 4, 5, 6, 7, 8, 9 or 10;
q is 0, 1, 2, 3, 4, 5 or 6;
s is 6, 7, 8, 9, 10, 11, 12, 13, 14, 15, 16, 17, 18, 19, 20, 21, 22, 23, 24, 25, 26, 27, 28 or 30;
Q comprises at least one of a fluorescent moiety, an electroactive moiety, a photocleavable moiety, a radioactive moiety, a chelating moiety and a spin label; and
X is one of a complementary functional group pair.

The present application also includes the use of one or more compounds of the application, or liposomes comprising one or more of the compounds of the application, for simultaneous transfection of one or more nucleic acid molecules into a cell and modification of the cell's membrane.

Thus, the present application includes a methodology that combines cell-surface modification, without the use of molecular biology techniques or biomolecules, and a simple, stable bio-orthogonal conjugation bottom-up approach that is capable of directing tissue formation and cell surface modification, along with optional nucleic acid transfection, and that will greatly benefit a range of medical applications. This platform will also find wide use in studying fundamental cell behavior and provide a range of new tools for tissue engineering and biomedical applications.

Other features and advantages of the present application will become apparent from the following detailed description. It should be understood, however, that the scope of the claims should not be limited by the embodiments set forth in the examples, but should be given the broadest interpretation consistent with the description as a whole.

BRIEF DESCRIPTION OF THE DRAWINGS

The present application will now be described in greater detail with reference to the drawings in which:

FIG. 1 (a) shows a comparison of the amount of cell surface labeling between hydrophobic and hydrophilic ketone molecules and (c) shows a comparison of the amount of cell surface labeling between hydrophobic and hydrophilic oxyamine ($-ONH_2$) molecules, as exemplary embodiments of the present application.

FIG. 3 shows 3D spheroid and multilayer structure cell viability, assayed using trypan blue in an exemplary embodiment of the present application.

DETAILED DESCRIPTION OF THE APPLICATION

I. Definitions

Figure 2:
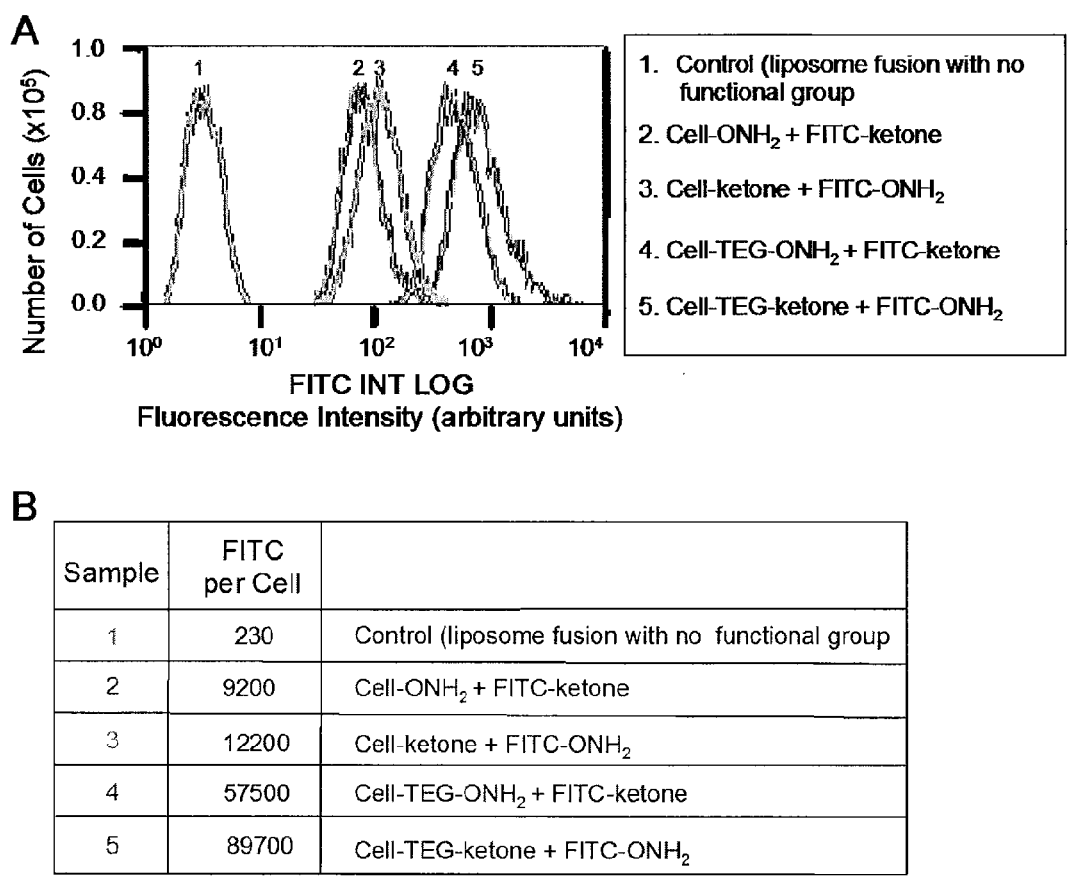
FIG. 2 shows a comparison of the amount of cell surface molecules (hydrophobic versus hydrophilic linkers) using flow cytometry in an exemplary embodiment of the present application.

Unless otherwise indicated, the definitions and embodiments described in this and other sections are intended to be applicable to all embodiments and aspects of the application herein described for which they are suitable as would be understood by a person skilled in the art.

As used in this application, the singular forms "a", "an" and "the" include plural references unless the content clearly dictates otherwise. For example, an embodiment including "a lipid" should be understood to present certain aspects with one lipid, or two or more additional lipids.

In embodiments comprising an "additional" or "second" component, such as an additional or second lipid, the second component as used herein is chemically different from the other components or first component. A "third" component is different from the other, first, and second components, and further enumerated or "additional" components are similarly different.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

The expression "compounds of the application" or "compounds of the present application" refers to amphiphatic molecules comprising a lipophilic portion, a hydrophilic portion and a functional group, wherein the functional group is bonded to the hydrophilic portion and is one of a functional group pair. In a specific embodiment, the compounds of the application" or "compounds of the present application" include compounds of Formula I, compounds of Formula II and compounds of Formula III. In a further specific embodiment, the compounds of the application" or "compounds of the present application" include compounds of Formula IV. In a still further specific embodiment, the compounds of the application" or "compounds of the present application" include compounds of Formula V.

The term "bio-orthogonal" as used herein refers to non-native, non-perturbing chemical functional groups that are introduced into naturally occurring, living systems and are modified in these living systems through selective reactions that do not interfere with any other chemical moieties in the natural surroundings.

The term "amphiphatic" or "amphiphilic" refers to a compound comprising both hydrophilic (water loving) and lipophilic (fat loving) portions.

The term "hydrophilic portion" as used herein refers to a portion of a molecule that has a tendency to interact with or be dissolved by water and other polar substances. The hydrophilic portion is typically charge-polarized and contains atoms that participate in hydrogen bonding. The hydrophilic portion may also be referred to as a polar portion. In one embodiment, the hydrophilic portion is any carbon-based moiety (or organic moiety) that has a solubility in water that is more than 1 mass %. In a further embodiment, the hydrophilic portion is any carbon-based moiety comprising at least one neutral hydrophile group per 5 carbons, or at least one electrically charged hydrophile group per 7 carbons. A representative example of a hydrophilic portion is an alkylene oxide chain, such as a methylene oxide, ethylene oxide, propylene oxide or butylene oxide chain.

The term "lipophilic portion" as used herein refers to a portion of a molecule that is soluble in fats, oils, lipids and non-polar solvents such as hexane and toluene. Lipophilic portions interact within themselves and with other substances through the London dispersion force. They have little to no capacity to form hydrogen bonds. A representative example of a lipophilic portion is a C6 or higher straight or branched chained alkyl or alkenyl group.

The term "fluorescent moiety" as used herein refers to any chemical grouping that contains electrons which can absorb a photon upon exposure to light and briefly enters an excited state before either dispersing the energy non-radioactively or emitting it as a photon, but with a lower energy.

The term "electroactive moiety" as used herein means any chemical grouping that has the ability to change electronic configuration, for example, by transferring electrons, acting as a conductor of electrons, and/or acting as an electron donor or acceptor.

The term "photocleavable moiety" as used herein means any chemical grouping that is cleaved (i.e. bonds are broken) upon exposure to light energy.

The term "radioactive moiety" as used herein means any chemical grouping that spontaneously emits energy in the form of particles of ionization (or radiation) from its nucleus. The particles of ionization include alpha particles, beta particles, and gamma rays. Examples of radioactive moieties, include, but are not limited to, $^{99}$Tc, $^{2}$H, $^{13}$C and $^{129}$I.

The term "chelating moiety" as used herein means any chemical grouping that forms two or more separate coordinate bonds with a single central atom. Chelating moieties are often referred to as ligands and are organic compounds containing heteroatoms, such as N, P, S and O that form two or more coordinate bonds with the central atom, which is often a metal.

The term "spin label" as used herein means a chemical grouping that acts as a molecular reporter because it is paramagnetic (contains an unpaired electron). Spin labels can be detected and monitored by electron paramagnetic resonance (EPR) or electron spin resonance (ESR) spectroscopy. A common example of a spin label is a nitroxide (N—O) group which is usually incorporated into a heterocyclic ring (e.g. pyrrolidine), and the unpaired electron is predominantly localized to the N—O bond.

The term "liposomes" as used herein refers to artificially prepared vesicles, the surface of which is a bilayer formed from amphiphatic molecules.

The term "liposomes of the application" or "liposomes of the present application" as used herein refers to liposomes comprising one or more compounds of the application.

The term "functional group" as used herein refers to a group of atoms or a single atom that will react with another group of atoms or a single atom (so called "complementary functional group") under bio-orthogonal reaction conditions to form a chemical interaction between the two groups or atoms.

The term "complementary functional group pair" as used herein means that the functional groups in the pair interact, or react with each other, to form a chemical interaction that is strong enough to promote the adhesion of the two types of liposomes or cells to each other. In an embodiment, the chemical interaction is a covalent bond or an ionic bond. In another embodiment, the chemical interaction is a covalent bond.

The term "one of a complementary functional group pair" as used refers to one member of a functional group pair.

The term "reacts with" as used herein generally means that there is a flow of electrons or a transfer of electrostatic charge resulting in the formation of a chemical interaction.

The term "chemical interaction" as used herein refers to the formation of either a covalent of ionic bond between the reactive functional groups. The chemical interaction is one that is strong enough to promote the adhesion of liposomes or cells.

The term "adhere" or "adhesion" as used herein means to bring two or more entities, such as two or more liposomes or two or more cells, into close proximity to each other and to remain in contact with each other. The adhered liposomes remain as separate entities or, their membranes destabilize and fuse together to result in the formation of a single liposome. In an embodiment, the adhered cells communicate with each other and/or divide and multiply forming, for example, tissues.

The term "alkyl" as used herein means straight or branched chain, saturated alkyl groups. The number of carbon atoms in the chain is defined by the $C_{\#-\#}$ prefix preceding the term. For example, the term $C_{6-30}$alkyl means an alkyl group having 6, 7, 8, 9, 10, 11, 12, 13, 14, 15, 16, 17, 18, 19, 20, 21, 22, 24, 25, 26, 27, 28, 29 or 30 carbon atoms.

The term "alkenyl" as used herein means straight or branched chain, unsaturated alkyl groups containing one or more, suitably one or three, more suitable one or two, double bonds. The number of carbon atoms in the chain is defined by the $C_{\#-\#}$ prefix preceding the term. For example, the term $C_{6-30}$alkyl means an alkenyl group having 6, 7, 8, 9, 10, 11, 12, 13, 14, 15, 16, 17, 18, 19, 20, 21, 22, 23, 24, 25, 26, 27, 28, 29 or 30 carbon atoms.

The term "oxyamine" as used herein refers to the functional group "—O—NH$_2$".

The term "amine" as used herein refers to the functional group "—NH$_2$".

The term "ketone" refers to the functional group

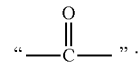

The term "aldehyde" as used herein refers to the functional group

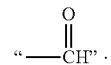

The term "nucleic acid" as used herein refers to both deoxyribonucleic acid (DNA) and ribonucleic acid (RNA).

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

II. Compounds of the Application and Compositions Thereof

The compounds of the application are amphiphatic molecules comprising a lipophilic portion, a hydrophilic portion and a functional group, wherein the functional group is bonded to the hydrophilic portion and is one of a complementary functional group pair.

In an embodiment, the compounds of the present application are compounds of Formula I:

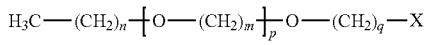   (I)

wherein:
n is 5, 6, 7, 8, 9, 10, 11, 12, 13, 14, 15, 16, 17, 18, 19, 20, 21, 22, 23, 24, 25, 26, 27, 28 or 29;
m is 1, 2, 3, or 4;
p is 1, 2, 3, 4, 5, 6, 7, 8, 9 or 10;
q is 0, 1, 2, 3, 4, 5 or 6; and
X is one of a complementary functional group pair.

In an embodiment of the application, the compounds of the application further comprise at least one of a fluorescent moiety, an electroactive moiety, a photocleavable moiety, a radioactive moiety, a chelating moiety and/or a spin label. These moieties are bonded to any available node on the compounds of the application. For example, in an embodiment, the fluorescent moiety, electroactive moiety, photocleavable moiety, radioactive moiety, chelating moiety and/or spin label is located between the lipophilic portion and the hydrophilic portion. Alternatively, in a further embodiment the fluorescent moiety, electroactive moiety, photocleavable moiety, radioactive moiety, chelating moiety and/or spin label is located between the hydrophilic portion and the functional group.

Therefore, in an embodiment, the compounds of the present application comprising a fluorescent moiety, an electroactive moiety, a photocleavable moiety, a radioactive moiety, a chelating moiety and/or a spin label are compounds of Formula II:

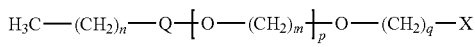   (II)

wherein:
n is 5, 6, 7, 8, 9, 10, 11, 12, 13, 14, 15, 16, 17, 18, 19, 20, 21, 22, 23, 24, 25, 26, 27, 28 or 29;
m is 1, 2, 3, or 4;
p is 1, 2, 3, 4, 5, 6, 7, 8, 9 or 10;
q is 0, 1, 2, 3, 4, 5 or 6;
Q comprises at least one of a fluorescent moiety, an electroactive moiety, a photocleavable moiety, a radioactive moiety, a chelating moiety and a spin label; and
X is one of a complementary functional group pair.

In another embodiment, the compounds of the present application comprising a fluorescent moiety and/or a photocleavable moiety are compounds of Formula III:

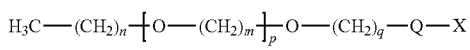   (III)

wherein:
n is 5, 6, 7, 8, 9, 10, 11, 12, 13, 14, 15, 16, 17, 18, 19, 20, 21, 22, 23, 24, 25, 26, 27, 28 or 29;
m is 1, 2, 3, or 4;
p is 1, 2, 3, 4, 5, 6, 7, 8, 9 or 10;
q is 0, 1, 2, 3, 4, 5 or 6;
Q comprises at least one of a fluorescent moiety, an electroactive moiety, a photocleavable moiety, a radioactive moiety, a chelating moiety and a spin label; and
X is one of a complementary functional group pair.

Accordingly, in combination, the present application includes a compound of the Formula IV:

   (IV)

wherein R is selected from:

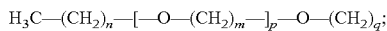

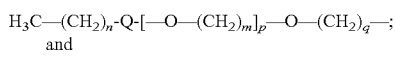
and

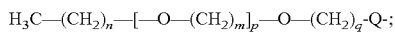

n is 5, 6, 7, 8, 9, 10, 11, 12, 13, 14, 15, 16, 17, 18, 19, 20, 21, 22, 23, 24, 25, 26, 27, 28 or 29;
m is 1, 2, 3, or 4;
p is 1, 2, 3, 4, 5, 6, 7, 8, 9 or 10;
q is 0, 1, 2, 3, 4, 5 or 6;
Q comprises at least one of a fluorescent moiety, an electroactive moiety, a photocleavable moiety, a radioactive moiety, a chelating moiety and a spin label; and
X is one of a complementary functional group pair.

The present application also includes a compound of the Formula V:

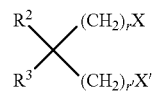   (V)

wherein $R^2$ and $R^3$ are each, independently selected from

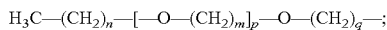

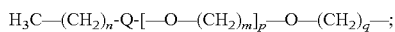

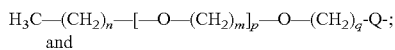
and

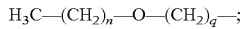

n is 5, 6, 7, 8, 9, 10, 11, 12, 13, 14, 15, 16, 17, 18, 19, 20, 21, 22, 23, 24, 25, 26, 27, 28 or 29;
m is 1, 2, 3, or 4;
p is 1, 2, 3, 4, 5, 6, 7, 8, 9 or 10;
q is 0, 1, 2, 3 or 46;
Q comprises at least one of a fluorescent moiety, an electroactive moiety, a photocleavable moiety, a radioactive moiety, a chelating moiety and a spin label; r and r' are each independently, 1, 2 or 3; and
X and X' are each, independently, one of a complementary functional group pair.

It is an embodiment of the application that the complementary functional group pairs in the compounds of the application are bio-orthogonal and chemoselective. Examples of complementary, bio-orthogonal pairs of functional groups include, but are not limited to:
(1) ketones and oxyamines which react to form an oxime;
(2) ketones and hydrazines which react to form a hydrazone;
(3) dienes and dienophiles which react to form a six membered ring (Diels Alder reaction);
(4) azides and alkynes which react to form a triazole (Huisgen reaction); and
(5) aldehydes and amines which react to form imines.

Other complementary functional group pairs that are not bio-orthogonal can be used for applications that do not involve naturally occurring living systems. Examples of such groups include thiols and disulfides, Michael donors and Michael acceptors, activated carboxylic acids and amines, two thiols, an azide and a triaryl phosphine (Staudinger reaction substrates) and a nitro phosphate and an alcohol (grafting).

In an embodiment, X is selected from a functional group comprising a ketone, an oxyamine, a hydrazine, a diene, a dienophile, an azide and an alkyne. In another embodiment, X is selected from a functional group comprising a ketone, an oxyamine, an aldehyde, an amine, a hydrazine, a diene, a dienophile, an azide and an alkyne. It another embodiment, the complementary functional group pair in the compounds of the application is a ketone and an oxyamine which react to form an oxime. Accordingly, it is an embodiment, that X is —C(O)R$^1$, wherein R$^1$ is C$_{1-2}$alkyl, or O—NH$_2$.

In a further embodiment of the application, the complementary functional group pair is a aldehyde and an amine which when contacted with each other, form a stable imine bond. Accordingly, in an embodiment of the application, X in the compounds of Formula I, II and III is, independently, C(O)H or X in the compounds of Formula I, II and III is NH$_2$. In another embodiment of the application, X and X' in the compounds of Formula V are, independently, C(O)H or X and X' in the compounds of Formula V are, independently, NH$_2$.

In an embodiment, n is 8, 9, 10, 11, 12, 13, 14, 15, 16, 17, 18, 19, 20, 21, 22, 23, 24, 25, 26, 27, 28 or 29.

In another embodiment, m is 2 or 3.

In another embodiment, p is 4, 5, 6, 7, 8, 9 or 10.

In another embodiment, q is 1, 2, 3 or 4.

As noted above, Q is group that comprises at least one of a fluorescent moiety, an electroactive moiety, a photocleavable moiety, a radioactive moiety, a chelating moiety and a spin label. In an embodiment, Q is a group that comprises at least one of a fluorescent moiety, an electroactive moiety and a photocleavable moiety. In an embodiment, the fluorescent moiety is a calcein or rhodamine or fluorescein moiety. In another embodiment, the electroactive moiety (hydroquinone or ferrocene). In a further embodiment, the photocleavable moiety is a 4-(1-hydroxyethyl)-2-methoxy-5-nitrophenoxy moiety.

In the compounds of Formula V, it is an embodiment that R$^2$ and R$^3$ are independently selected from:

H$_3$C—(CH$_2$)$_n$—[—O—(CH$_2$)$_m$—]$_p$—O—(CH$_2$)$_q$—;
and

H$_3$C—(CH$_2$)$_n$—O—(CH$_2$)$_q$—.

In a further embodiment, R$^2$ and R$^3$ in the compounds of Formula V are independently H$_3$C—(CH$_2$)$_n$—[—O—(CH$_2$)$_m$—]$_p$—O—(CH$_2$)$_q$—. In a further embodiment, R$^2$ and R$^3$ in the compounds of Formula V are both H$_3$C—(CH$_2$)$_n$—[—O—(CH$_2$)$_m$—]$_p$—O—(CH$_2$)$_q$—.

In an embodiment, n in the compounds of Formula V, is 8, 9, 10, 11, 12, 13, 14, 15, 16, 17, 18, 19, 20, 21 or 22.

In another embodiment, m in the compounds of Formula V is 2 or 3.

In another embodiment, p in the compounds of Formula V is 4, 5, 6, 7, 8, 9 or 10.

In another embodiment, q in the compounds of Formula V is 1 or 2.

In another embodiment of the application, X and X' in the compounds of Formula V are both C(O)R$^1$, wherein R$^1$ is C$_{1-2}$alkyl, or X and X' in the compounds of Formula V are both O—NH$_2$. In another embodiment of the application, X and X' in the compounds of Formula V are both C(O)H or X and X' in the compounds of Formula V are both NH$_2$. In another embodiment of the application, X and X' in the compounds of Formula V are both C(O)H.

In another embodiment of the application, r and r' in the compounds of Formula V are 1 or 2.

In a further embodiment, the compound of Formula I and II (or compound of Formula IV) is selected from:

CH$_3$(CH$_2$)$_{10}$—[OCH$_2$CH$_2$]$_3$OCH$_2$C(O)CH$_3$;  (Ia)

CH$_3$(CH$_2$)$_{10}$—[OCH$_2$CH$_2$]$_4$OCH$_2$CH$_2$CH$_2$SH;  (Ib)

CH$_3$(CH$_2$)$_{10}$—[OCH$_2$CH$_2$]$_3$OCH$_2$CH$_2$ONH$_2$;  (Ic)

CH$_3$(CH$_2$)$_{10}$—[OCH$_2$CH$_2$]$_4$OCH$_2$C≡CH;  (Id)

CH$_3$(CH$_2$)$_{10}$—[OCH$_2$CH$_2$]$_4$OCH$_2$CH$_2$N$_3$;  (Ie)

(If)

H$_3$C—(CH$_2$)$_{10}$—[O—(CH$_2$)$_2$]$_4$—O—(CH$_2$)$_4$—[benzoquinone];

CH$_3$(CH$_2$)$_{10}$—[OCH$_2$CH$_2$]$_4$OCH$_2$CH$_2$NH—NH$_2$;  (Ig)

(Ih)

H$_3$C—(CH$_2$)$_{10}$—[O—(CH$_2$)$_2$]$_4$—O—CH$_2$—[N-hydroxysuccinimide ester];

CH$_3$(CH$_2$)$_{10}$—[OCH$_2$CH$_2$]$_3$OCH$_2$CH$_2$NH$_2$;  (Ii)

CH$_3$(CH$_2$)$_{10}$—[OCH$_2$CH$_2$]$_4$OCH$_2$C≡CH$_2$;  (Id)

(Ii)

H$_3$C—(CH$_2$)$_{10}$—[O—(CH$_2$)$_2$]$_3$—O—(CH$_2$)$_2$—[cyclopentadiene];

(Ij)

H$_3$C—(CH$_2$)$_{10}$—[O—(CH$_2$)$_2$]$_4$—O—(CH$_2$)$_2$—[maleic anhydride];

(IIa)

H$_3$C—(CH$_2$)$_{10}$—O—CH(CH$_3$)—[2-nitro-5-methoxyphenyl]—O—(CH$_2$)$_3$—C(O)—NH—CH$_2$CH$_2$—[O—(CH$_2$)$_2$]$_2$O—(CH$_2$)$_2$-ONH$_2$;

-continued
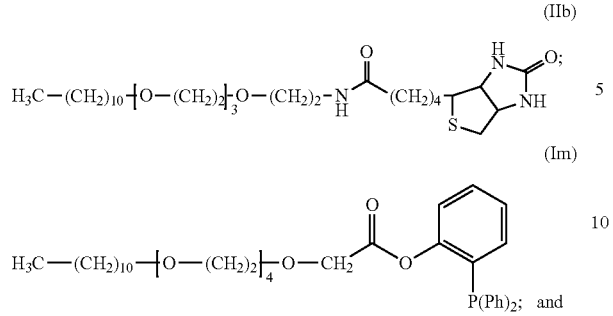
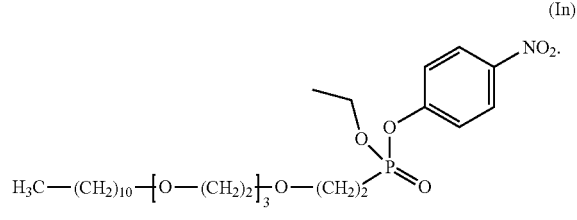
In another embodiment of the compound of Formula V is selected from
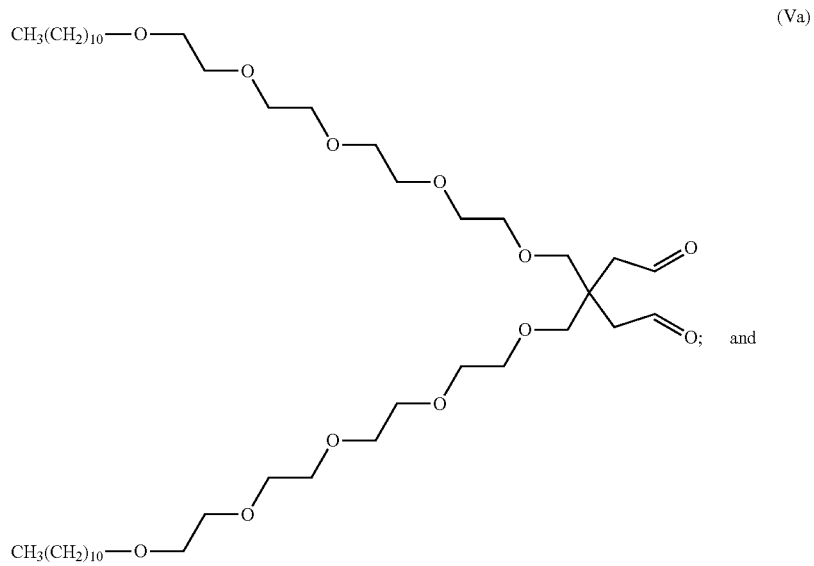
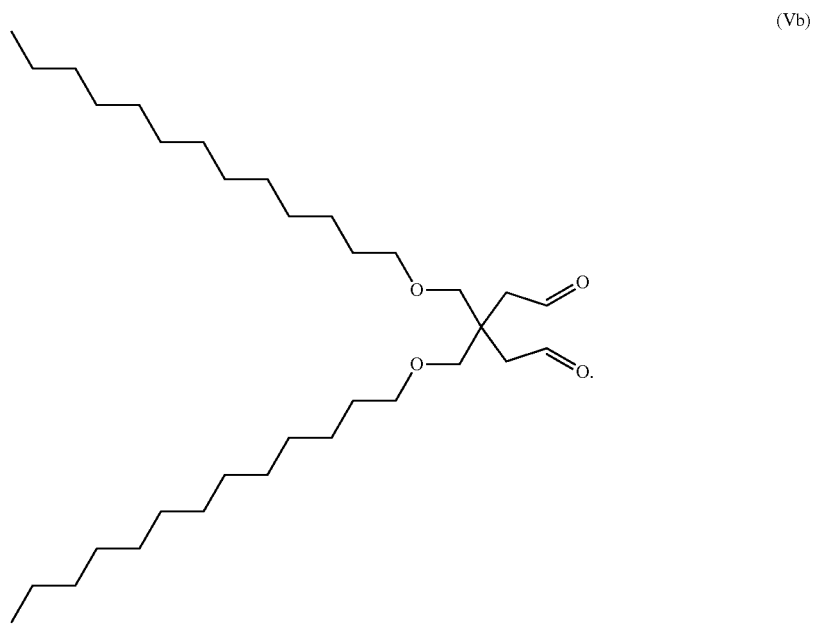

The compounds of the application, in certain embodiments, have at least one asymmetric centre. Where compounds possess more than one asymmetric centre, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (e.g. less than 20%, suitably less than 10%, more suitably less than 5%) of compounds of the application having alternate stereochemistry.

The present application also includes a liposome comprising one or more compounds of the application, that is one or more amphiphatic molecules, wherein the amphiphatic molecules comprise a lipophilic portion, a hydrophilic portion and a functional group, and the functional group is bonded to the hydrophilic portion and is one of a functional group pair. In an embodiment of the application, the compounds of the application are selected from one or more of a compound of Formula I, Formula II and Formula III. In an embodiment of the application, the compounds of the application are selected from one or more of a compound of Formula IV. In an embodiment of the application, the compounds of the application are selected from one or more of a compound of Formula V.

In an embodiment of the application, aside from the compounds of the application, the liposomes further comprise any suitable amphiphatic molecule, or mixture of molecules, that form liposomes. In general, liposome-forming amphiphatic molecules are lipids, in particular phospholipids. In a further embodiment, the liposome-forming amphiphatic molecules are selected based on the proposed use of the liposome. For example, if the liposomes are to be adhered to each other, the liposome-forming amphiphatic molecule is any suitable neutral, positively charged or negatively charged amphiphatic molecule or a mixture thereof. In general, to enhance the attraction between the two entities to be adhered or fused, the charges on each entity are opposite. Examples of suitable liposome-forming amphiphatic molecules are diverse and the present application is not limited to any specific type. Selection of the liposome-forming amphiphatic molecule and methods for the formation of liposomes are well within the skill of a person in the art.

Any known method for the preparation of liposomes is used to prepare the liposomes of the present application. For example, the liposomes are formed by dissolving the compounds of the application in an organic solvent and thoroughly combining the resulting solution with the liposome-forming amphiphatic molecule(s), also dissolved in an organic solvent, followed by removal of all of the organic solvents. The dried samples are then reconstituted and brought to the desired concentration in an aqueous buffer solution, such as an aqueous buffer having a pH of about 7 to about 7.5. Sonication and warming may be used to obtain a clear solution of large unilamellar vesicles (LUVs). The liposomes are optionally reduced in size, for example, using extrusion methods.

As a representative nonlimiting example, the liposome-forming amphiphatic molecule is selected from one or more of palmitoyl-oleoyl phosphatidylcholine (POPC—a neutral phospholipid), dipalmitoylphosphatidylcholine (DPPC—a neutral phospholipid), 1-palmitoyl-2-oleoyl-phophatidyl-glycerol (POPG, a negatively charged phospholipid) 1,2-dimyristoyl-sn-glycero-3-phosphoglycerol (DMPG, a negatively charged or anionic phospholipid) and 1,2,-dioleoyl-3-trimethylammonium-propane (DOTAP—a positively charged or cationic lipid).

As a further representative example, the liposome-forming amphiphatic molecule is selected from egg palmitoyl-oleoyl phosphatidylcholine (POPC—a neutral phospholipid), egg 1-palmitoyl-2-oleoyl-phophatidylglycerol (POPG, a negatively charged phospholipid) and 1,2,-dioleoyl-3-trimethylammonium-propane (DOTAP—a positively charged or cationic lipid).

In an embodiment, the amount of the compounds of the application in the liposome is about 1 mol % to about 10 mol %, or about 5 mol %. It is another embodiment, that the liposome comprises about 90 mol % to about 99 mol % of a neutral lipid and, optionally, about 1 mol % to about 5 mol % of a charged lipid.

In another embodiment of the application, the liposomes further comprise fluorescent reporter molecules. In one embodiment, the fluorescent reporter molecules are incorporated into the liposome-forming amphiphatic molecules. When present in the liposome-forming amphiphatic molecules, it is an embodiment that these molecules are incorporated into the liposomes in an amount of about 0.5 mol % to about 5 mol %, or about 2 mol %. As a representative example, the fluorescent phospholipids, egg 1,2-diphytanoyl-sn-glycero-3-phosphoethanolamine-N-(7-nitro-2-1,3-benzoxadiazol-4-yl) (ammonium salt) (NBD-PE), and egg 1,2-dipalmitoyl-sn-glycero-3-phosphoethanolamine-N-(lissamine rhodamine B sulfonyl) (ammonium salt) (Rhod-PE), are used. The incorporation of fluorescent reporter molecules into the liposome-forming amphiphatic molecules allows for easy monitoring of liposome adhesion and fusion. For example, the use of NBD-PE (a fluorescence donor) in one type of liposomes and rhod-PE (a fluorescence acceptor) in a second type liposomes results in a gradual decrease in the donor emission peak and increase in the acceptor emission peak upon adhesion of the two types of liposomes.

In yet another embodiment, the liposomes further comprise other functional molecules, such as fluorescent molecules, dyes and/or other indicator molecules, so that when the liposomes are fused, a physical change, such as a change in color, fluorescence or smell, occurs. These functional molecules may be entrapped within the liposomes or be incorporated into the liposome-forming amphiphatic molecules.

In a further embodiment of the application, the liposomes further comprise biologically active agents, such as nucleic acids, proteins, peptides, small molecule drugs, carbohydrates and the like, and mixtures thereof, and fusion of the liposomes with any cell population results in the simultaneous delivery of the biological agents into the cells and modification of the cell's surface with at least one of a complementary functional group pair. The biologically active agents may be entrapped within the liposome or may be incorporated into the liposome membrane.

In yet another embodiment, the liposomes are combined with one or more nucleic acid molecules to form a nucleic acid-liposome complex. These complexes, when delivered to cells result in simultaneous transfection of the cells with the nucleic acid molecule(s) and modification of the cell's surface with at least one of a complementary functional group pair. The transfected and cell surface modified cells can then undergo subsequent cell-cell assembly or reaction, for example, with a range of ligands, small molecules and proteins via bio-orthogonal ligation.

The present application also includes compositions comprising one or more of the above-identified liposomes. In a further embodiment, the composition further comprises a solvent, diluent or carrier, such as an aqueous buffer.

III. Methods of Preparation

The compounds of the present application are prepared using methods known in the art. For example the various portions, including the lipophilic portion, the hydrophilic portion and the functional group are coupled together using known chemistries, including nucleophilic displacements, activation of carboxylic acids followed by displacement of activating groups by nucleophiles and cross couplings. Active functional groups are protected with protecting groups, if needed, prior to the coupling reactions and then removed after the coupling reactions. The fluorescent moiety, electroactive moiety, photocleavable moiety, radioactive moiety, chelating moiety and spin label are incorporated into the compounds of the application using the same methodology. Representative examples of methods for preparing the compounds of the application are shown in Schemes 1 and 2.

Protecting groups are chemical moieties which protect or mask a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, 3$^{rd}$ Edition, 1999 and in Kocienski, P. Protecting Groups, 3rd Edition, 2003, Georg Thieme Verlag (The Americas). Examples of suitable protecting groups include, but are not limited to t-Boc, Ac, Ts, Ms, silyl ethers such as TMS, TBDMS, TBDPS, Tf, Ns, Bn, Fmoc, dimethoxytrityl, methoxyethoxymethyl ether, methoxymethyl ether, pivaloyl, p-methoxybenzyl ether, tetrahydropyranyl, trityl, ethoxyethyl ethers, carbobenzyloxy, benzoyl and the like.

IV. Liposome Fusion

The present application also includes a mixture comprising a plurality of liposomes of type A and a plurality of liposomes of type B, wherein the liposomes of type A comprise a compound of the application having a functional group that is complementary to a functional group on compounds of the application comprised in the liposomes of type B to form a chemical interaction that results in adhesion of the liposomes of type A and the liposomes of type B.

In an embodiment of the application, the adhesion of the liposomes of type A and the liposomes of type B results in formation of multiadherent liposomes, the partial fusion of liposomes of type A and the liposomes of type B and/or the complete fusion of the liposomes of type A and type B. In an further embodiment, the adhesion of the liposomes of type A and the liposomes of type B results in the complete fusion of the liposomes of type A and the liposomes of type B to make larger liposomes of type "AB".

The present application also includes a method for promoting adhesion of liposomes comprising contacting a plurality of liposomes of type A with a plurality of liposomes of type B, wherein the liposomes of type A comprise a compound of the application having a functional group that is complementary to a functional group on compounds of the application comprised in the liposomes of type B to form a chemical interaction that results in adhesion of the liposomes of type A and the liposomes of type B.

The application also includes a use of one or more compounds of the application to promote the adhesion of liposomes.

The present application further includes kits or commercial packages for performing the method of promoting the adhesion of liposomes. In an embodiment, the kit or package comprises, in separate containers, a solution of a plurality of liposomes of type A and a solution of a plurality of liposomes of type B, wherein the liposomes of type A comprise a compound of the application having a functional group that is complementary to a functional group on compounds of the application comprised in the liposomes of type B to form a chemical interaction that results in adhesion of the liposomes of type A and the liposomes of type B, along with instructions for performing the method. In one embodiment, the kit or package further comprises separate means for forming bubbles with the each of the plurality of liposomes of type A and a plurality of liposomes of type B. Any means for forming bubbles may be used, such as any shaped device upon which a film of the solution comprising the liposomes of type A and the solution of the liposomes of type B can form and the user can apply a flow of a gas, such as air, to form bubbles. Examples of such means include the typical bubble blowing devices that are found in children's bubble forming toy products. In an embodiment, the instructions include directions to form a bubble from each of the solutions of liposomes of types A and B and to bring the bubbles into contact with each other. In a further embodiment, each of the liposomes of type A and type B further comprise an indicator molecule, such as a dye, and contact of the bubbles of type A with the bubbles of type B results in a fused bubble having a different detectable property, such as a different colour. In an embodiment, these kits and commercial packages are used or sold as novelty items or toys.

V. Liposome Fusion to Cells

Liposome fusion to mammalian and bacterial cell membranes was directed through the use of a charged lipids and a molecular recognition pair for chemoselective ligation using the compounds of the application. Applications for this strategy, include, but are not limited to, small molecule delivery, cell-surface modification, tissue engineering, biologically active molecule delivery, vaccine generation, study of bacterial behavior, bacteria detection and study of bacteria pathogenicity. By employing this membrane tailoring strategy, the assembly of 3D spheroid clusters and tissue-like structures were directed after culturing two cell populations functionalized with oxyamine- and ketone-containing groups. Because this method is general, bio-orthogonal, chemically stable, and non-cytotoxic, patterned multi-layered tissue-like structures of different geometric shapes could also be fabricated without the use of 3D scaffolds to confine the cell populations. It has also been shown that this method has promising use in stem cell transplantation by co-culturing human mesenchymal stem cells (hMSCs) with fibroblasts (fbs) and inducing adipocyte differentiation while in a 3D multi-layered tissue-like structure. Also demonstrated was the inclusion of fluorescent, electroactive and photocleavable moieties in the functional group presenting molecules for further manipulation of cellular interactions.

Other functional groups, such as radioactive moieties, chelating moieties and spin labels are also delivered to the cell membrane using the methods of the application.

Accordingly, the present application includes a method of modifying a cell membrane comprising contacting the cell with a liposome comprising one of more compounds of the application under conditions for incorporation of the compounds into the cell membrane.

The present application also includes the use of one or more compounds of the application for modifying a cell membrane.

In another embodiment, the present application includes a method for promoting the adhesion of cells comprising:
(a) contacting a first cell population with a liposome of type A under conditions for the fusion of the liposome of type A with the first cell population;
(b) contacting a second cell population with a liposome of type B under conditions for the fusion of the liposome of type B with the second cell population; and
(c) contacting the fused first cell population with the fused second cell population,
wherein the liposomes of type A comprise a functional group that reacts with a functional group comprised in the liposomes of type B to form a chemical interaction that results in the adhesion of the first and second cell populations.

To promote the fusion of the liposomes to cells, a mixture of neutral, positively and/or negatively charged liposome-forming amphiphatic molecules are used depending on the cell type and corresponding membrane characteristics. For example, fusion to mammalian cells types, whose membranes comprise a negative charge, is promoted by incorporating positively charged lipids in to the liposome. While not wishing to be limited by theory, the positively charged lipid enhances membrane fusion via electrostatic destabilization.

In an embodiment, the liposomes of the application comprise a neutral lipid, a positively charged lipid and one or more compounds of the application. Such a liposome composition is useful, for example, for fusion with cell membranes having a negative charge, such as mammalian cells, and for forming complexes with negatively charged molecules, such as nucleic acids (see below). In an embodiment, a variation in the molar ratio of the neutral lipid to the positively charged lipid is made for different cells types. In an embodiment, the positively charged lipids are incorporated in an amount of 1 mol % to about 5 mol %, or about 2 mol %.

In an embodiment, the liposomes of the application comprise a neutral lipid, a negatively charged lipid and one or more compounds of the application. Such a liposome composition is useful, for example, for fusion with bacterial cell membranes or for forming complexes with molecules having a positive charge. In an embodiment, the negatively charged lipids are incorporated in an amount of 1 mol % to about 5 mol %, or about 2 mol %.

Promotion of liposome fusion to all cell types, including prokaryotic and eukaryotic, for example, mammals, plants, bacteria, viruses and the like, can be done using a similar strategy depending on the characteristics of the cell membrane.

The conditions for the fusion of the liposomes with the cell populations generally involve adding an aqueous buffered solution of the liposomes to the cells in culture and incubating the cells in the presence of the liposomes for example, for 6 to about 24 hours. In an embodiment the solution of the liposomes is added at a concentration of about 0.5 to 5 mM and about 1 to about 10 mL of this solution is added to about 1 to about 10 mL of the cultured cells. When the cell populations are incubated with the liposomes comprising a reactive functional group, membrane fusion occurs, resulting in the presentation of the reactive functional groups from the cell surfaces. These reactive functional groups are available for further reaction so that when these cell populations are contacted together, interconnected, 3D tissue-like structures form, mediated through chemoselective reactions between the complementary functional groups. These reactive functional groups are also available for further reaction with other molecules comprising the other member of the functional group pair, opening the door for a multitude of possible modifications to the cell's surface. Using the compounds of the application in which hydrophilic linker groups have been incorporated resulted in greater amounts of reactive functional groups presented at the cell's surface compared to corresponding compounds having hydrophobic linker groups (see FIGS. 1 and 2).

In an embodiment, the contacting of the fused first cell population with the fused second cell population can be done using any suitable means. For example, the cell populations may be combined in solution. As a representative example, oxyamine presenting rat2 fibroblasts were combined in solution with ketone-presenting Swiss albino 3T3 fibroblasts and, upon mixing, these two cell populations formed clusters and tissue-like masses. This is a significant finding as current methods to generate these types of structures require the support of a 3D hydrogen matrix and/or assisted assembly through an external stimulus.

Alternatively, one of the cell populations may be grown on a substrate and the second cell population added as a layer on top of the first population, followed by addition of alternate layers of the first and second population of cells. In this embodiment, larger, dense 3D tissue-like networks are formed with geometric control. In this embodiment, the 3D-tissue like networks are released from the substrate using, for example, agitation or washing, accordingly, this method provides the possibility for applications in tissue engineering and cellular transplantation.

Another alternative is to combine the two cell populations in a continuous fashion, for example, by flowing one stream comprising the first population of cells into a second stream comprising the second population of cells, using microfluidics. Using microfluidics in combination with the surface-modified cells of the present application, will allow that rapid generation of co-culture microtissue in flow. This will provide new ways to generate complex tissues and lead to new technologies to assemble and grow tissues that complement current bioreactor methods (see for example, FIG. 4).

Figure 4:
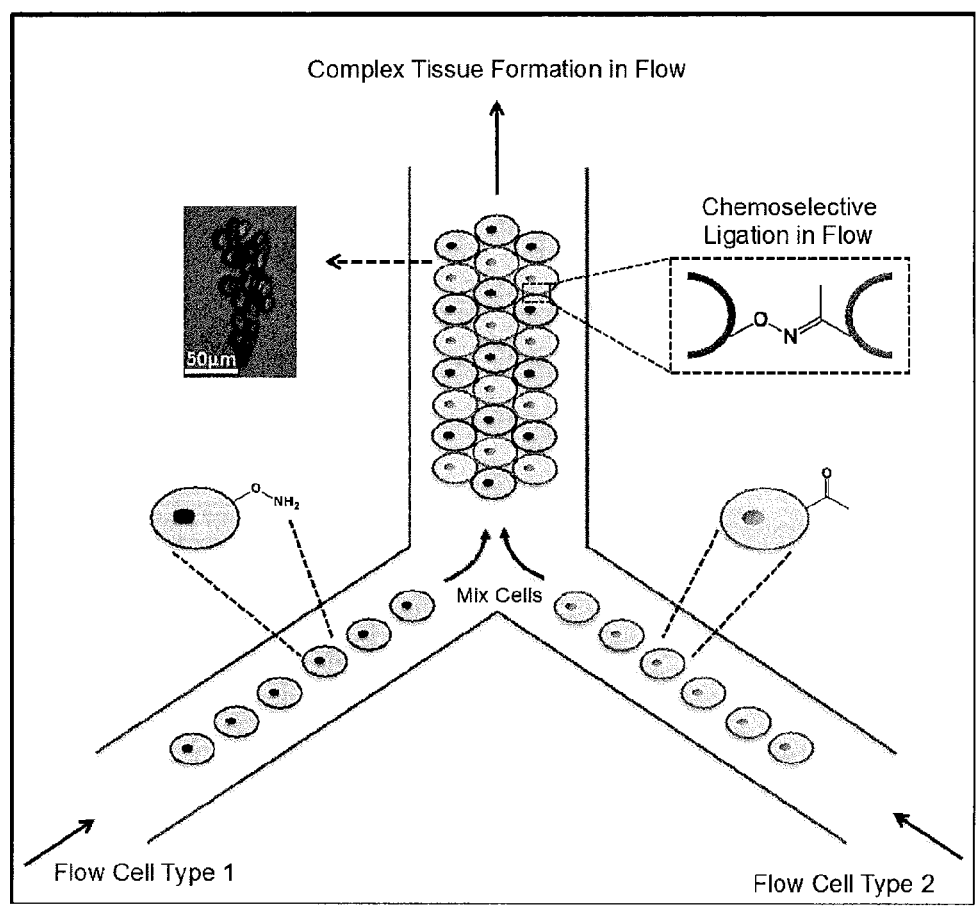
FIG. 4 shows a schematic of generating microtissue in flow in an exemplary embodiment of the present application. By using microfluidic channels engineered cells can rapidly form complex assemblies in flow. Multiple cell lines and polymers may be incorporated to generate tubular and multiple cell type core shell (onion) type tissues.

Using cell lines presenting complementary functional group pairs it has been shown that, upon cell-cell interaction in flow, microtissues could be grown via interfacial oxime chemistry. Two different fibroblast cell lines were generated that contained ketone and oxyamine groups respectively. Each cell line was introduced into a flow chamber and upon mixing a rapid, covalent and stable interaction occurred to assemble and grow microtissue (FIG. 4). Cells that did not possess the correct chemistry did not assemble into tissues. These results show the combination of surface-modified cells and microfluidics can generate complex tissues rapidly for a range of fundamental cell behavioural studies, biotechnologies and tissue formation.

The microfluidic technology is expanded to generate complex tissues that incorporate multiple cell lineages, as well as to generate more complex microfluidic chambers to introduce multiple different surface-modified cell lines at different stages of microtissue formation to generate shelled tissue structures, for example, using tubular biodegradable polymers.

In an embodiment, at least one of the populations of cells is a stem cell and adhesion of a second population of a specific cell type results in induced differentiation and proliferation of the stem cells as the second cell type. This result holds great potential for areas of regenerative medicine and stem cell transplantation.

In a further embodiment of the application, the liposomes of type A and/or B further comprise biologically active agents, such as nucleic acids, proteins, peptides, small molecule drugs, carbohydrates and the like, and mixtures thereof, and fusion of the liposomes with the cell population results in the delivery of the biological agents into the cells. The biologically active agents are either entrapped within the liposome and/or are incorporated into the liposome membrane.

In yet another embodiment, the liposomes of type A and/or B further comprise other functional molecules, such as fluorescent molecules, dyes and/or other indicator molecules, so that when the first and second cell populations are adhered, a physical or sensory change, such as a change in color or fluorescence occurs. These functional molecules are either entrapped within the liposomes and/or are incorporated into the liposome-forming amphiphatic molecules.

In another embodiment of the application, the liposomes of type A and type B further comprise fluorescent reporter molecules. In one embodiment, the fluorescent reporter molecules are incorporated into the liposome-forming amphiphatic molecules. When present in the liposome-forming amphiphatic molecules, it is an embodiment that these molecules are incorporated into the liposomes in an amount of about 0.5 mol % to about 5 mol %, or about 2 mol %. As a representative example, the fluorescent phospholipids, egg 1,2-diphytanoyl-sn-glycero-3-phosphoethanolamine-N-(7-nitro-2-1,3-benzoxadiazol-4-yl) (ammonium salt) (NBD-PE), and/or egg 1,2-dipalmitoyl-sn-glycero-3-phosphoethanolamine-N-(lissamine rhodamine B sulfonyl) (ammonium salt) (Rhod-PE), are used. The incorporation of fluorescent reporter molecules into the liposome-forming amphiphatic molecules allows for easy monitoring of liposome fusion and subsequent cell adhesion.

The ability to tailor cell surfaces with new functionalities allows for many new applications and studies. For example, when these cells are contacted with other entities, including cells, and/or other molecules or substrates, comprising a complementary functional group, chemical interaction occurs resulting in the joining of the entity with the cell, providing a vast array of possible methods for manipulating the cell. In an embodiment, the inclusion of at least one of a photocleavable moiety, fluorescent moiety, electroactive moiety, radioactive moiety, chelating moiety and spin label in the compounds of the application provides for further routes of cellular manipulation as described below.

Photocleavable Amphiphatic Molecules

Figure 5:
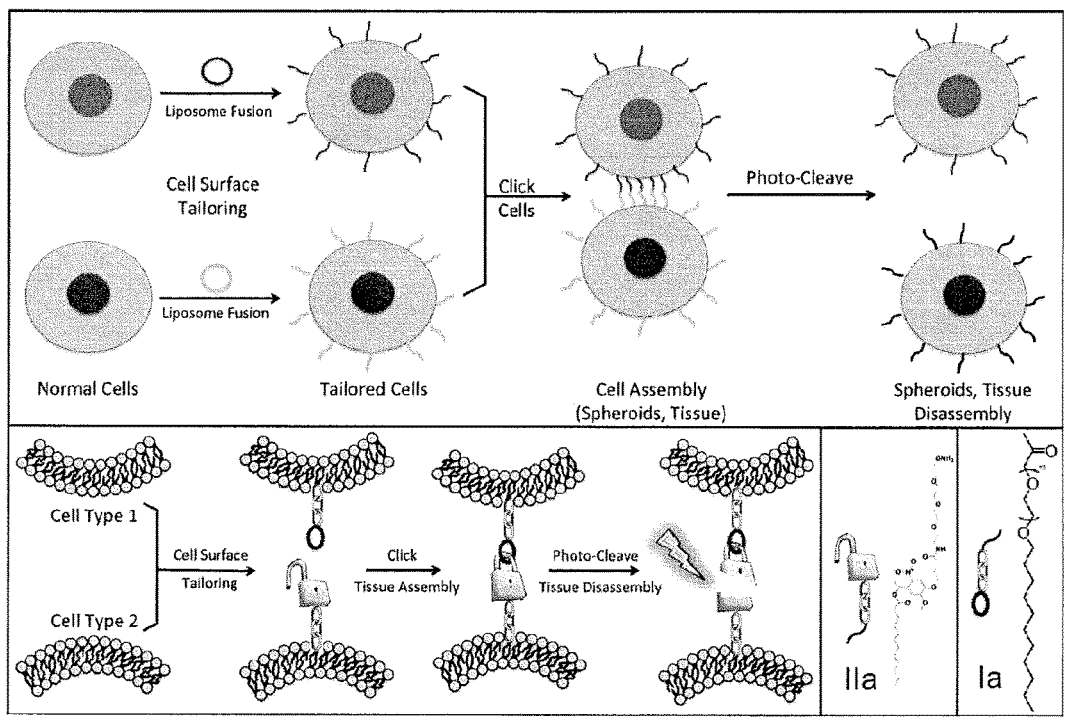
FIG. 5 is a schematic describing the molecular level control of tissue assembly and disassembly via a chemoselective, bio-orthogonal and photo-switchable cell surface engineering approach in an exemplary embodiment of the present application.
Figure 6:
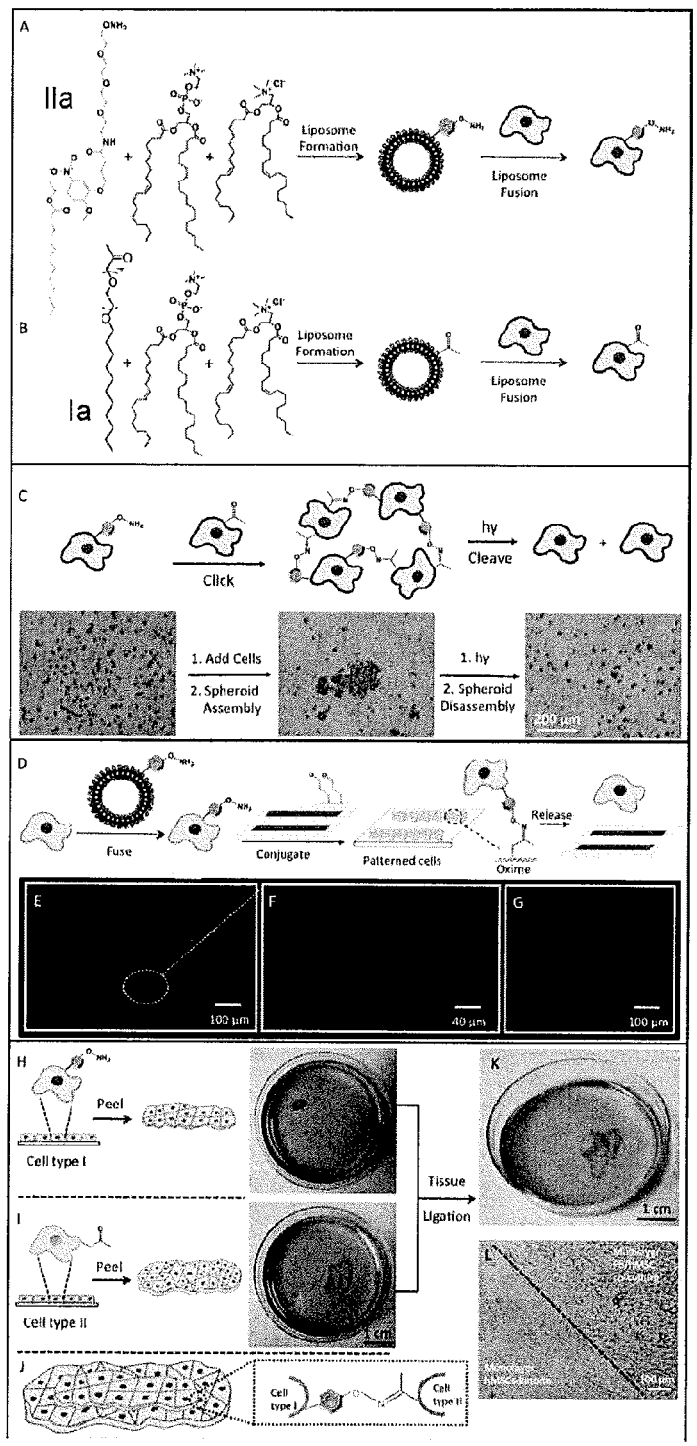
FIG. 6 shows the design of liposomes to deliver chemoselective, bio-orthogonal and photo-active groups to cell surfaces and the subsequent application to assemble and disassemble tissue structures on demand in solution and on materials in exemplary embodiments of the present application. (A) A photolabile oxyamine molecule is mixed with POPC and positively charged DOTAP to generate photoactive liposomes that are delivered to cell surfaces via liposome fusion. (B) Dodecanone is mixed with POPC and DOTAP molecules to generate ketone presenting liposomes that are delivered to cell surfaces via liposome fusion. (C) When non-adherent Jurkat cells presenting ketones and photo-oxyamine were mixed, 3D spheroid cell assemblies were formed due to oxime ligation between the cell lines. Upon UV illumination, the spheroids disassemble due to the cleavage of the intercellular oxime tether. (D) Fibroblasts presenting the photo-active oxyamine chemoselectively adhere to materials presenting aldehyde groups (E, F) through an interfacial oxime linkage. The rewired cells could then be selectively released from the material upon UV illumination (G). (H-L) Construction of multi-tissue co-culture systems. Two different types of cells (fibroblasts and hMSCs), tailored with photo-oxyamine (H) and ketone (I) respectively, were peeled from tissue culture plates and assembled via the oxime ligation (J, K) to form a stable multi-tissue co-culture system. (L) Phase contrast microscopy of the tissue showing portions of multilayer and monolayer. The cell layers only adhered if the complementary chemistry was present on their cell surfaces.
Figure 7:
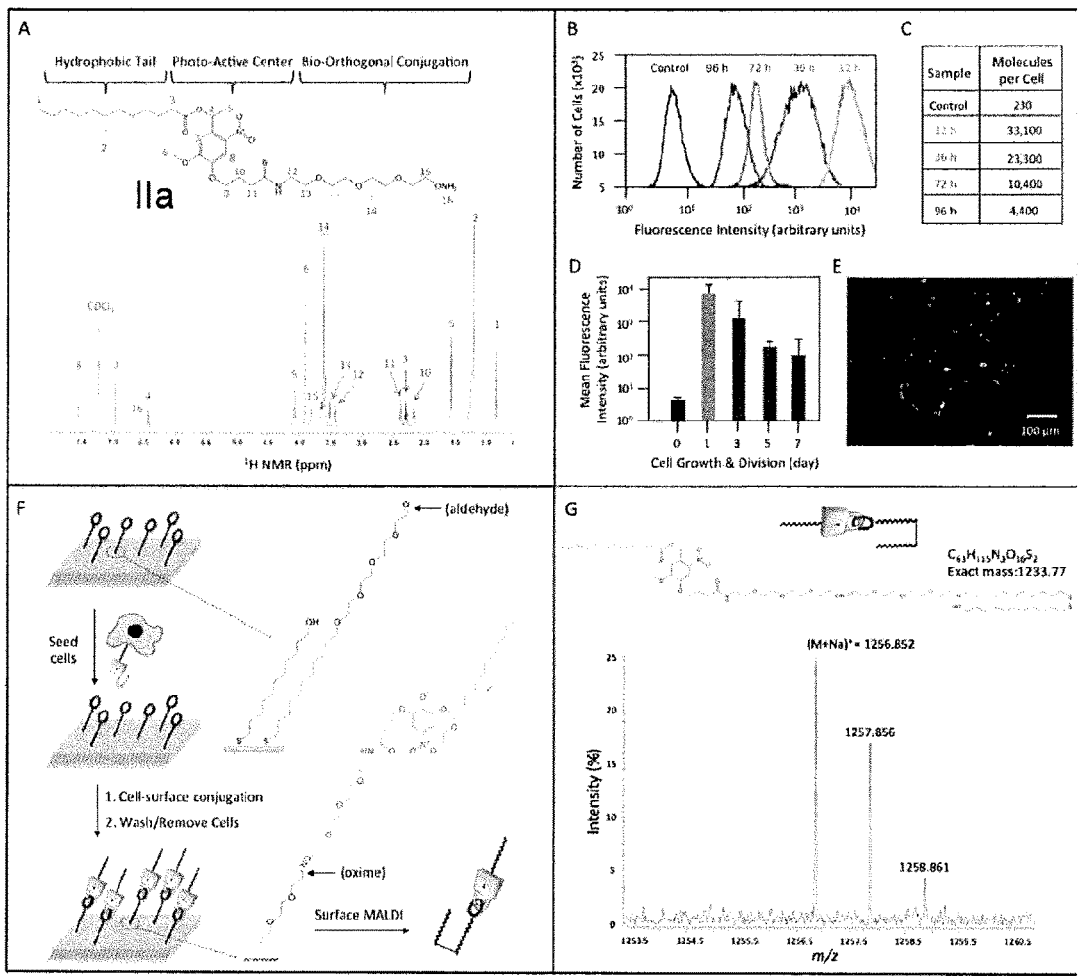
FIG. 7 shows the characterization of the photo-oxime reaction at cell surfaces in exemplary embodiments of the present application. (A) NMR characterization of the photo-oxyamine molecule. Each part of the molecule is designed to optimize membrane insertion, photo-cleavability and availability of the oxyamine group for intercellular ligation. (B) Flow cytometry analysis to determine the amount of photo-oxyamine molecules per cell surface. Fibroblast cells (fbs) were cultured with or without (control) photo-oxyamine containing liposomes for different time periods. The fbs were then reacted with a ketone containing fluorescent calcein dye. The fbs were then tested against a standard bead (~$10^7$ beads/mL) with known fluorescein molecule density. Approximately 25×$10^3$ cells were counted for all samples. Samples were run in triplicate, and the mean fluorescence intensity values are displayed. (C, D) Histograms relating the number of cells counted as a function of fluorescence intensity are shown and labeled as control (without photo-oxyamine) and 12 h, 36 h, 72 h, and 96 h (with photo-oxyamine). (E) Micrograph of fbs presenting photo-oxyamine reacted with calcein. When no photo-oxyamine is present in the cell surface, no fluorescence is observed. (F) A cartoon describing the interfacial reaction between the surface-engineered cells and a self-assembled monolayer (SAM) on a gold substrate. Cells tailored with the photo-oxyamine group are seeded onto a SAM presenting aldehyde groups to form an interfacial oxime ligation. After washing and removing the cells, the photo-oxyamine lipid is pulled out of the cell membrane and remains ligated to the SAM via the covalent oxime bond. (G) MALDI-MS characterization of the resulting substrate shows an interfacial reaction occurs between the rewired cell surfaces and the aldehyde substrate via oxime ligation.
Figure 8:
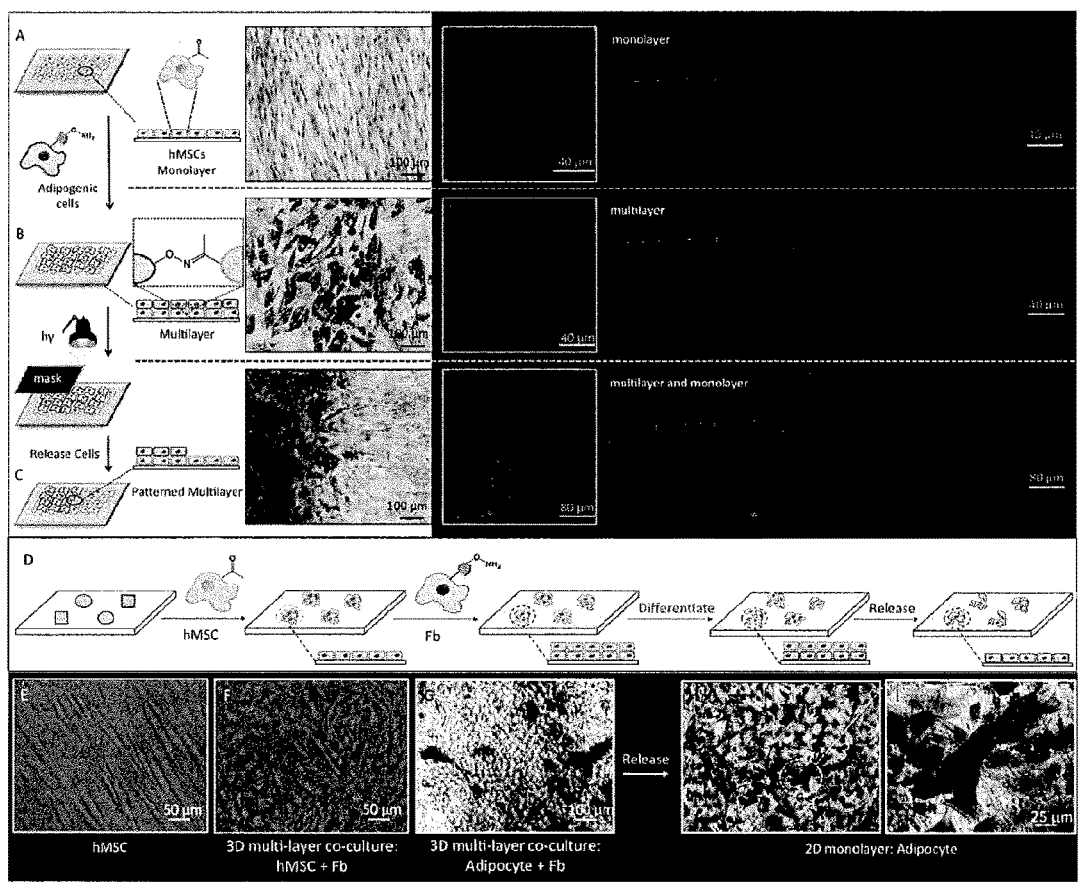
FIG. 8 shows a general schematic, and optical and confocal images of chemoselective and photo-switchable tissue assembly and disassembly in exemplary embodiments of the present application. (A) Top row. Two different cell populations (hMSCs and adipogenic cells) tailored with ketones and photo-oxyamine, respectively, were conjugated together via the chemoselective oxime ligation to form a multilayer co-culture system (B, middle row). (C) Bottom row. Select photo-disassembly of the tissue multilayer to a monolayer occurred upon uv exposure through a mask. After partially exposing to UV, the co-culture system was partially disassembled to form specially controlled monolayer again. (D) Schematic and corresponding phase contrast and optical images displaying the formation, differentiation, and release of 3D dynamic tissues using a Fb/hMSC co-culture. Ketone tailored hMSCs (8) were cultured on a substrate ($10^5$ cells/mL, 3 d) and formed a 2D monolayer as shown by the image in (E). Fbs presenting photo-oxyamine were then added ($10^5$ cells/mL, 2 d), producing a 3D multi-layered, interconnected co-culture tissue (F). When the appropriate induction media is used, the hMSCs differentiated into adipocytes, resulting in a 3D multi-layered co-culture of Fbs and adipocytes (G). Photo-release of Fbs from the co-culture left only the adhered adipocytes on the surface as a 2D monolayer shown by lower (H) and higher (I) magnified images. Adipocytes were stained for lipid vacuoles (red, Oil Red O) and nucleus (blue, Harris Hemotoxylin).

A general strategy has been developed that delivers photocleavable and bio-orthogonal chemistry via liposome fusion to cell surfaces for subsequent in-situ tailoring for on-demand micro-tissue assembly and disassembly (FIGS. 5-8). As a representative example, a novel liposome fusion system was developed to deliver bio-orthogonal photoactive oxyamine lipid and ketone-lipid like molecules to cell membranes. Upon mixing these cells in different formats, co-culture spheroids and multilayers could be generated due to an intercellular oxime ligation. Since the ligation tether contained a photocleavable group, remote control of disassembly could be achieved upon UV light illumination (FIGS. 6 and 7). This system was demonstrated in several cell lines to generate switchable co-culture spheroids and multi-layers. This photo-active cell surface engineering system was further demonstrated by conjugating and tracking cell surface ligands and applying a photocleavable oxime bond formation between cells for the spatial and temporal control of multilayer tissue assembly and disassembly for manipulating HMSC stem cell differentiation (FIG. 8).

In an embodiment, the photo-active lipid molecule is used to generate photo-switchable engineered stem cells for temporal studies of stem cell plasticity. It has been shown that HMSC stem cells can retain the photo-active lipid and form spheroid and tissue co-cultures with fibroblasts. HMSC-fibroblast co-cultures are generated and used to study the role of interaction duration on the rate of differentiation. Since the tissues can be cleaved, and the HMSC and fibroblast cells separated upon demand, each population's genomic and proteomic profile as a function of interaction duration can be studied. Straightforward gene microarrays and mass-spectrometry proteomics analysis are compared to control populations. The time course of HMSC differentiation to adipocytes and osteoblasts as a function of fibroblast or other cell type association can also be studied. These studies delineate the role of co-culture cell-cell interactions and provide an interaction map of stem cell differentiation for a range of different cell type-stem cell studies. Large co-culture tissues are made between fibroblasts and then microfiche masks and ultraviolet light illumination are used to generate patterned 3D structures. These studies are then combined with 3D printing technology and UV light illumination to generate more complex 3D tissues. This methodology, in conjunction with 3D printing, 3D laser imaging and bioreactor technology has the potential to generate myriad shapes of complex tissue of multiple-cell types. Programmable shapes and assemblies of any cell lines will provide new methods for a range of fundamental stem cell plasticity studies and the potential to engineer any complex tissue through automated 3D printers and lasers.

In summary, a novel liposome fusion system to deliver bio-orthogonal photo-active lipid and functional group-lipid like molecules to cell membranes has been developed. Upon mixing these cells in different formats, co-culture spheroids and multilayers were generated due to an intercellular bio-orthogonal bond formation. Since the ligation tether contains a photo-cleavable group, remote control of disassembly was achieved upon UV light illumination. This system was demonstrated in several cell lines to generate switchable co-culture spheroids and multi-layers. Flow cytometry and mass spectrometry analysis quantified and characterized the interfacial cell surface reaction. The ability to engineer cell surfaces with a straightforward and inexpensive liposome fusion strategy will find wide use in fundamental studies of membrane biophysics, paracrine signaling and adapted to generate new biomaterials and as a biotechnology platform for screening complex cell behaviors in tissue microarrays. Several other bio-orthogonal chemical ligation strategies including Diels-Alder, Huisgen, oxime, hydrazone, thiol-ene, imine, etc. may be used to tailor cell surfaces with nanoparticles, redox groups and a range of other molecules for targeted delivery and as cell tracking and imaging beacons. The spatial and temporal control of cell interactions between multiple different cell types will lead to new studies of dynamic cellular communication. Furthermore, the combination of bioreactor technologies with intercellular ligation methods provides new ways to generate large-scale complex multi-cell type tissues. When combined with traditional polymer scaffolds, molds or printing technologies, a range of complex 3D tissues and organs are possible for an array of biomedical diagnostic and transplantation applications.[71-73]

Fluorescent Moieties

A major theme in studying and manipulating interactions at cell surfaces is the ability to simultaneously visualize and tailor events that occur at cell membranes. These multimodal approaches are complex and a system where docking and changing cell surfaces are observed in real-time is desirable. A method that can provide a beacon on a cell surface that becomes fluorescent upon specific binding allows for many opportunities to image, track and manipulate cell and tissue behaviour in space and time.

Figure 9:
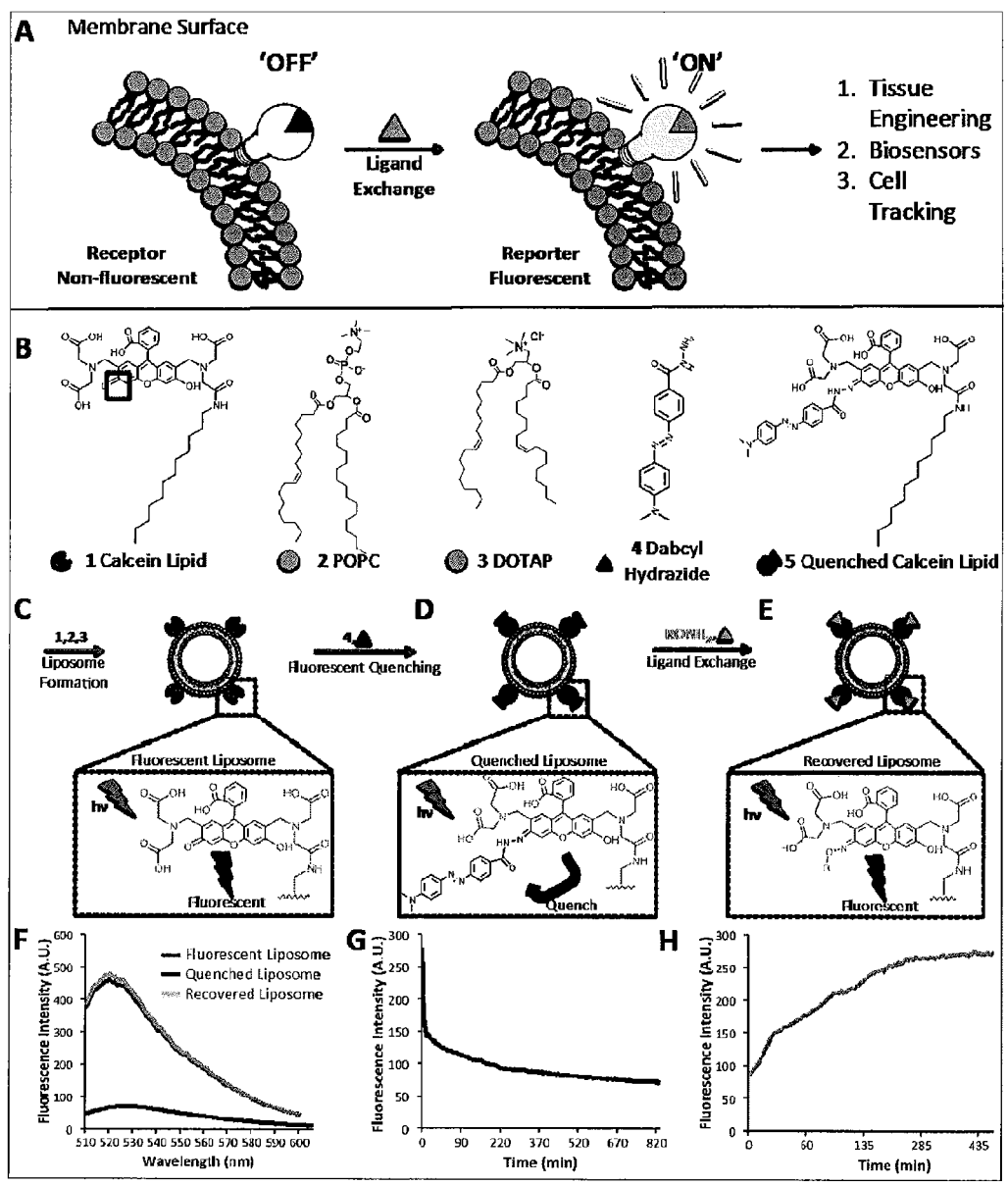
FIG. 9 shows the design and characterization of a dual cell surface fluorescent receptor and reporter system in exemplary embodiments of the present application. A) Cartoon of a cell membrane where a non-fluorescent reporter can be activated by ligand exchange to become a fluorescent reporter for cell surface engineering. B) List of molecules used in this study. C) Fluorescent liposomes were synthesized by sonication containing 1, 2 and 3. D) These fluorescent liposomes were quenched via a chemoselective and bio-orthogonal reaction with dabcyl hydrazide to generate 5. E) The fluorescence was activated by ligand-oxyamine exchange. F) Graph of fluorescent intensity vs. wavelength. Both the recovered and initial fluorescent liposomes were highly fluorescent. However, once reacted with the efficient quencher dabcyl hydrazide, the fluorescence from the liposomes was significantly reduced. G) Graph of fluorescent intensity vs. time for the liposome quenching reaction measured at 525 nm with 495 nm excitation. H) Graph of fluorescent intensity vs. time for the fluorescent recovery reaction measured at 525 nm with 495 nm excitation.
Figure 10:
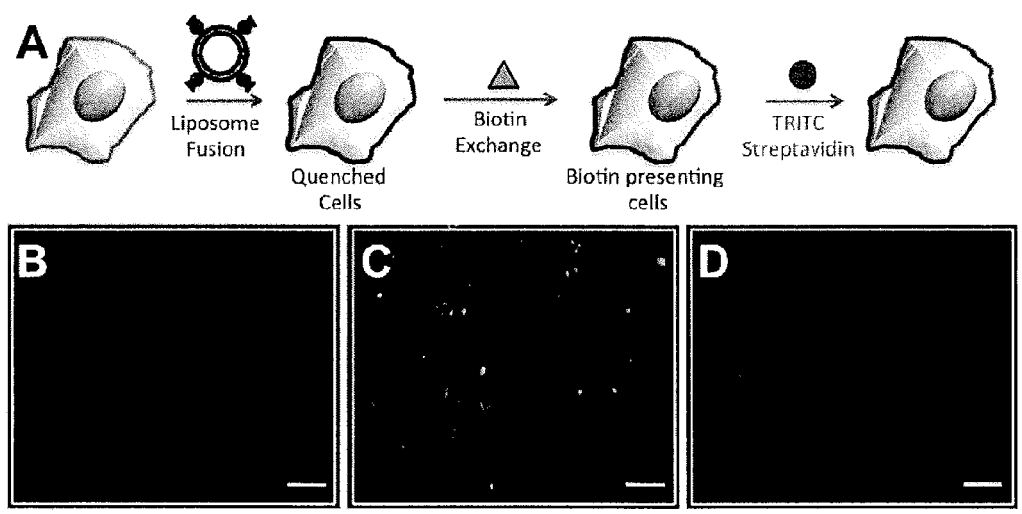
FIG. 10 shows the characterization of changing cell fluorescence by liposome fusion, ligand conjugation and protein binding to cell surfaces in exemplary embodiments of the present application. A) Cells were first fused with quenched liposomes followed by biotin hydrazide to exchange the dabcyl quencher and functionalize the cell surface with biotin. Then, TRITC labeled streptavidin was added and bound specifically to the biotin presenting cell surface. B) Fluorescent micrograph of cells fused with quenched liposomes. C) Fluorescence activation 12 h after media containing biotin hydrazide was added to the cells in order to exchange dabcyl and to label cell surfaces with biotin. D) Biotin presenting cells became red after 4 h of exposure to media containing TRITC labeled streptavidin.
Figure 11:
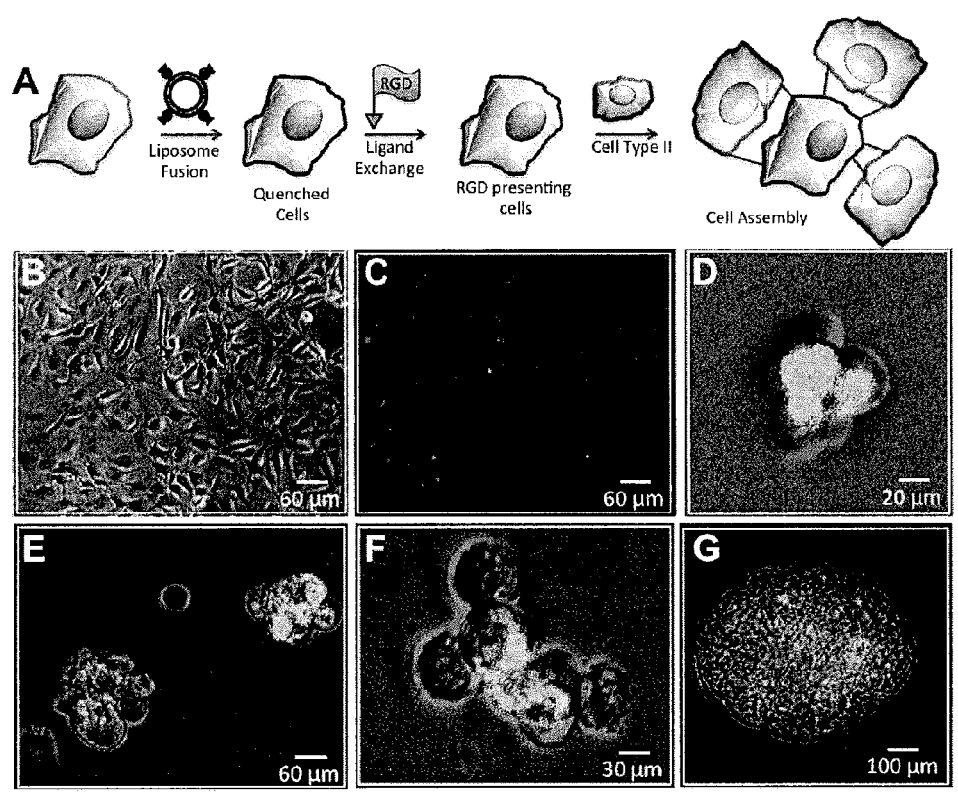
FIG. 11 shows the formation and characterization of cell assemblies by a dual receptor and reporter cell surface engineering strategy in exemplary embodiments of the present application. A) Cells are fused with quenched liposomes and then reacted with RGD-oxyamine to became fluorescent. These cells now present the RGD ligand on their cell surface. These cells were mixed with a second different population of cells (untreated) to which they rapidly formed cell assemblies due to RGD-integrin recognition between cells. B) Control experiment. A brightfield image of fibroblasts fused with quenched liposomes then reacted with a scrambled non-adhesive oxyamine peptide. C) Fluorescent micrograph of these cells demonstrating that cell surface fluorescence had been activated but no assemblies formed due to the lack of a bio specific interaction between the scrambled ligand and integrin receptors. D) Overlay images of cells treated with quenched liposomes then reacted with RGD-oxyamine. Upon addition of another non-labeled cell population cell assemblies formed through RGD-integrin interaction. Cells were allowed 1 h to form in solution. The same experiment repeated for E) 2 h, F) 4 h, and G) 8 h. The cell clusters grew in size and the RGD cells are marked by their fluorescence.
Figure 12:
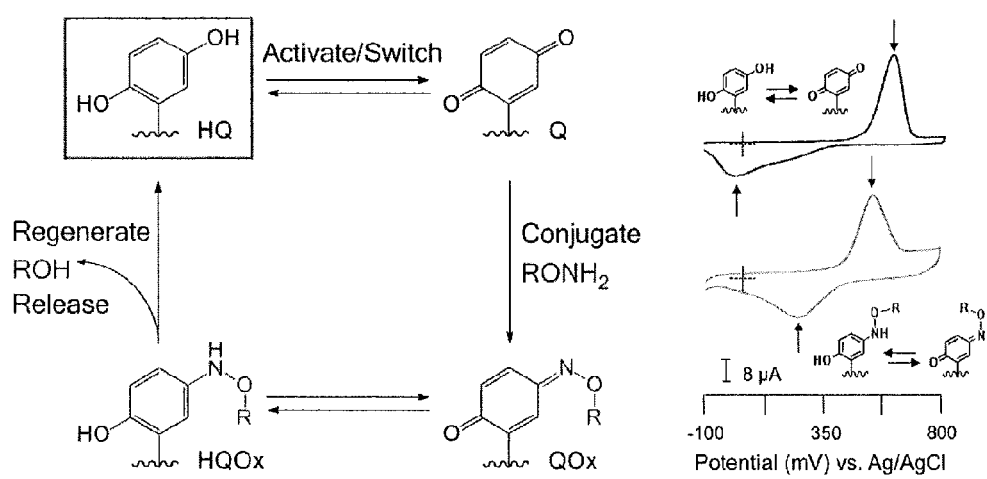
FIG. 12 shows the chemical cycle for redox active, oxime conjugation and release in exemplary embodiments of the present application. Hydroquinone (HQ) can be chemically (20 μL, 5 μM $CuSO_4.5H_2O$ in PBS at 10 mol %, 5 min) or electrochemically (−100 to 650 mV, pH 0, 100 $mVs^{-1}$) oxidized to Quinone (Q) for ligation with aminooxy (AO)-tethered ligands (R—$ONH_2$), resulting in a shift of the diagnostic reduction peak associated with the redox species (bottom cyclic voltammogram (CV)). The redox cycle of oxime (QOx to HQOx) is stable at pH<5 and does not cleave. When this redox cycle is performed at pH>5, the oxime bond is efficiently cleaved to regenerate HQ. The regenerated HQ can then continue the cycle for subsequent rounds of the conjugation and release of AO-tethered ligands (R—$ONH_2$).
Figure 13:
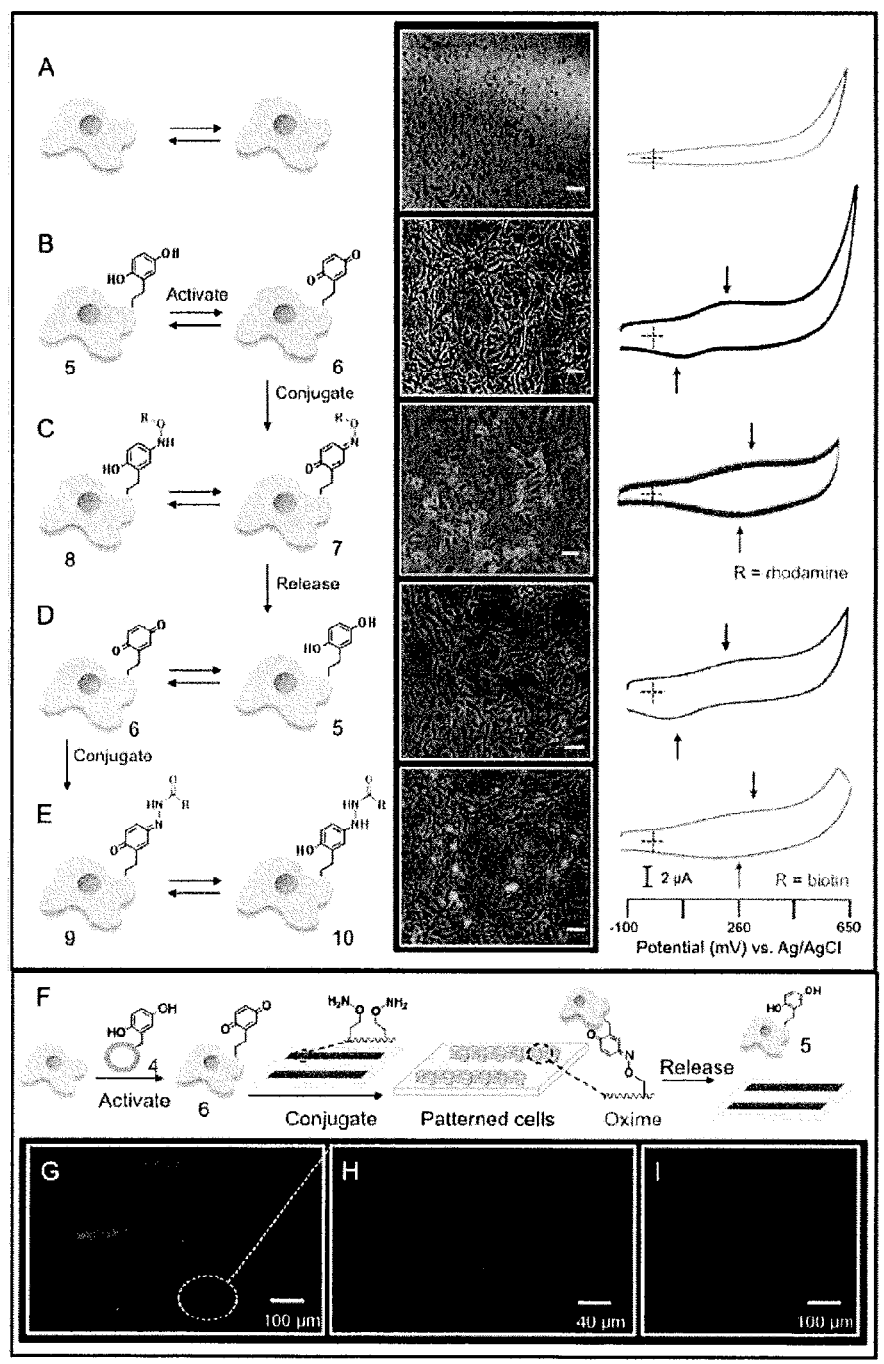
FIG. 13 shows fluorescent and electrochemical characterization of cyclical cell-surface tailoring and the release of ligands based on redox responsive chemoselective chemistry in exemplary embodiments of the present application. (A) Fibroblasts (Fb), not fused with liposomes presenting HQ groups show no redox signal or fluorescence. (B) HQ-containing liposomes (4) are added to Fbs (3 mM in tris buffer, 400 μL to 4 mL, 16 h), resulting in membrane fusion and presentation of HQ from the surface (5). The stable HQ (5) to Q (6) interconversion can be monitored by cyclic voltammetry (CV) (−100 to 650 mV, pH 0, 100 mVs$^{-1}$) due to its diagnostic redox peaks (black trace, HQ=130 mV, Q=258 mV). (C) Activated Q-presenting Fbs (6) can be chemoselectively reacted with rhodamine-AO (7 mM in $H_2O$, 100 μL to 4 mL, 30 min) for cell-surface tailoring (7 and 8). This results in stable, fluorescently labeled cells (red) and a diagnostic shift in redox signal (red trace, 252 my, 284 mV). (D) In a reductive environment (−100 mV, 10 s, pH 7.4), the oxime bond is cleaved with the release of rhodamine and the regeneration of HQ-presenting Fbs (5) as indicated by a loss in fluorescence and the redox peaks of the HQ to Q cycle (black trace). (E) Cell surfaces can once again be conjugated for a second time with hydrazide-tethered biotin (9 and 10) and fluorescein-presenting streptavidin (1 mg/mL in PBS, 0.5 mL to 2 mL, 1 h each), resulting in fluorescently labeled cells (green) and a shift in redox peaks (green trace). (Bottom) A general schematic and corresponding fluorescent images demonstrating dynamic control of cell adhesion and release from patterned substrates (F). Fbs were cultured with HQ-containing liposomes (4), resulting in membrane fusion and subsequent display of HQ from cell surfaces (5). Mild chemical oxidation (20 μL, 5 μM $CuSO_4 \cdot 5H_2O$ in PBS at 10 mol %, 5 min) converts the HQ to Q groups on the cell surface (6). Q-presenting Fbs (6) ($10^4$ cells/mL, 2 h) were then added to a substrate patterned with AO-terminated ligands (1 mM in EtOH, 1:9 AO/$EG_4$). Cells adhered to the substrate due to a biospecific interfacial oxime ligation and then proliferated (4 d) within the patterned region as shown in lower (G) and higher (H) magnified fluorescent micrographs. Upon electrochemical reduction, the interfacial oxime is cleaved and the cells are released from the substrate (I). Cells were stained for actin (red, phalloidin), nucleus (blue, DAPI), and anti-vinculin (green, Cy-2).
Figure 14:
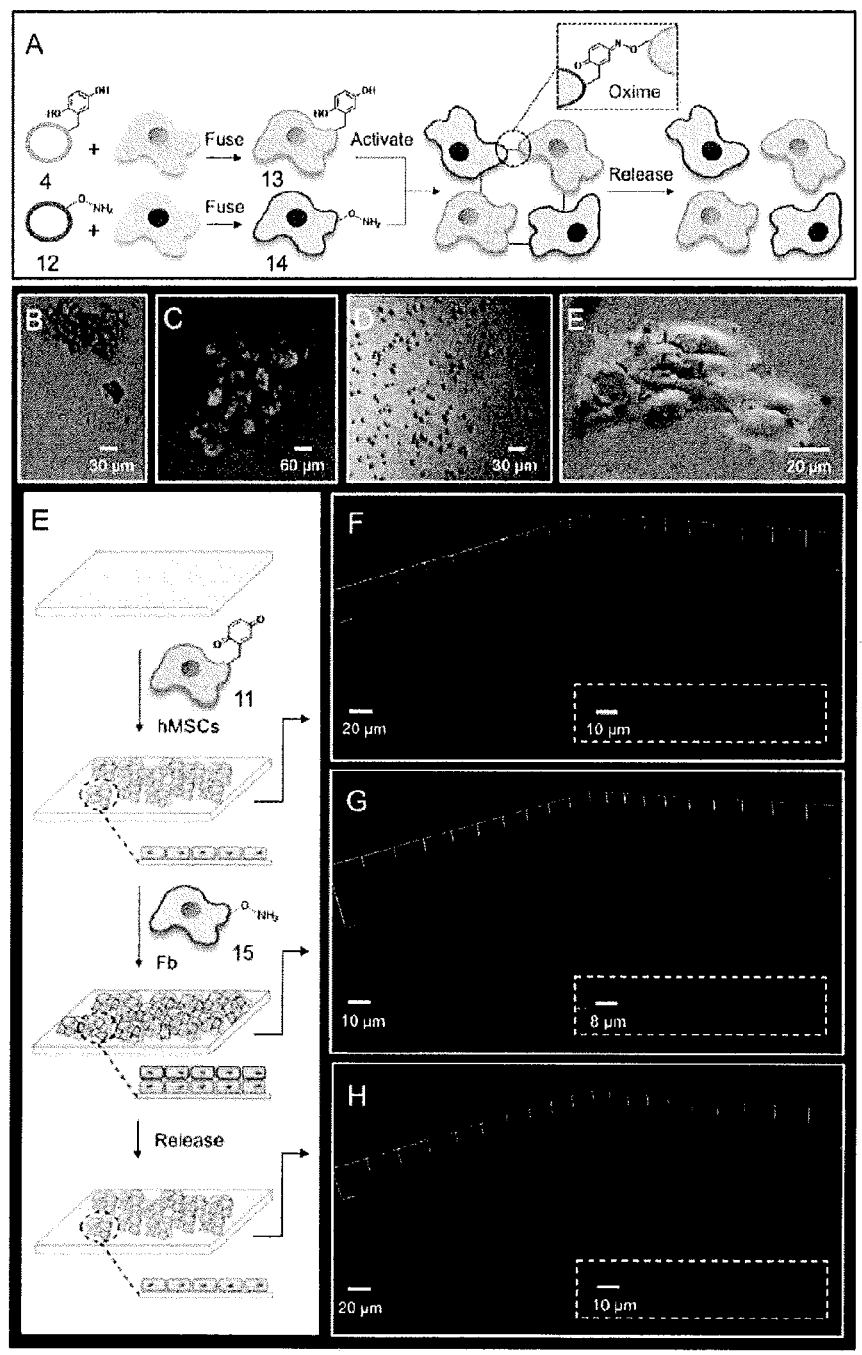
FIG. 14 shows a schematic and corresponding images of 3D dynamic spheroid and multi-layered tissue assembly and disassembly via liposome fusion and chemoselective cell-surface tailoring in exemplary embodiments of the present application. (A) Human mesenchymal stem cells (hMSCs) are functionalized with HQ groups (13) (3 mM in tris buffer, 400 μL to 4 mL, 16 h) after liposome fusion and are then activated to Q (11). Fbs presenting AO groups (14) are then co-cultured (1 mL, 1:1, 3 h) with Q-displaying hMSCs (11), producing (B and C) 3D spheroid assemblies, interconnected through chemoselective oxime chemistry. Mild electrochemical reduction (−100 mV, 10 s, pH 7.4) causes oxime cleavage and the dynamic disassembly of cells as shown in (D). (E) Activated, Q-tethered hMSCs (11) are cultured on a substrate ($10^5$ cells/mL, 3 d), resulting in a 2D cell monolayer (F). AO-presenting Fbs (15) are added ($10^5$ cells/mL, 2 d) to the hMSCs (11), and a 3D interconnected multi-layered structures (G). A reductive potential applied to the substrate cleaves the oxime bond and induces the dynamic release of Fbs from the multi-layer, regenerating the 2D monolayer of hMSCs (H). The nuclei of OA-tethered Fbs (14) shown in C are stained with m-cherry for enhanced visualization. HMSCs (11) and Fbs (15) displayed in F-H are stained for actin (red, phalloidin) and nucleus (blue, DAPI).
Figure 15:
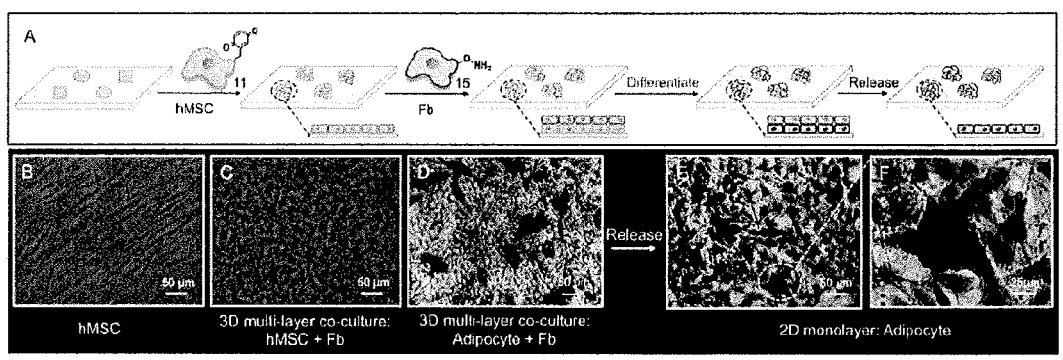
FIG. 15 shows a schematic and corresponding phase contrast images displaying the formation, differentiation, and release of 3D dynamic tissues using a Fb/hMSC co-culture in exemplary embodiments of the present application. (A) Activated, Q-tethered hMSCs (11) are cultured on a substrate ($10^5$ cells/mL, 3 d) and form a 2D monolayer as shown by the image in (B). AO-presenting Fbs (15) are then added ($10^5$ cells/mL, 2 d), producing a 3D multi-layered, interconnected co-culture (C). When the appropriate induction media is delivered to the co-culture, hMSCs differentiate into adipocytes, resulting in a 3D multi-layered co-culture of Fbs and adipocytes (D). A reductive potential (−100 mV, 10 s, pH 7.4) applied to the substrate results in oxime cleavage and the dynamic release of Fbs, leaving only the adhered adipocytes on the surface as a 2D monolayer shown by lower (E) and higher (F) magnified images. Adipocytes were stained for lipid vacuoles (red, Oil Red O) and nucleus (purple, Harris Hemotoxylin).

Therefore the present application also includes a novel receptor/reporter system based on liposome fusion to incorporate a unique bio-orthogonal lipid that has the dual ability to serve as a receptor for chemoselective cell surface tailoring and as a reporter to track cell behavior (FIG. 9). The bimodal amphiphatic molecule contains a FRET pair comprising a calcein dye joined with an efficient quencher dabcyl through an exchangeable linkage. While in a cell's membrane the non-fluorescent amphiphatic molecule can be turned on by the addition of an complementary functional group-containing ligand, which exchanges with the dabcyl quencher. This allows for the in situ simultaneous tailoring and fluorescent tracking of cells. The general utility of this strategy can be demonstrated by tailoring cells with small molecules and peptides for real-time analysis of cell surface modification (FIGS. 10 and 11).

Synthetic chemistry can be used to further explore the dual receptor and reporter system and then evaluate these systems for cell surface engineering applications in tissue imaging. A modified calcein dye has been prepared and a FRET quenched bio-orthogonal exchange version incorporated into cell membranes. There are currently over 20 dyes with similar structures to calcein but with different excitation and emission profiles that are amenable to this synthetic modification system. This provides a suite of different coloured receptor reporter systems that allows for the simultaneous tracking of multiple cell lines.

In an embodiment, the dual receptor reporter system is used to conjugate cell adhesive peptides (e.g. RGD-oxyamine peptide) to cell surfaces. This allows for the cell to become 'sticky' and upon introduction of another cell type generates complex tissue (based on RGD-integrin interactions). This methodology has been carried out on several cell lines (FIG. 11). The preparation of complementary functional group-containing peptides, such as oxyamine-containing peptides, is known to a person skilled in the art, for example, on a peptide synthesizer. One feature is that only cells that become fluorescent (exchange with the dabcyl quencher) have the peptide modification. These cells can therefore be selected for further manipulation or, in the presence of a non-modified second cell type, immediately form spheroids and tissue like structures. The RGD-complementary functional group-containing peptides are used in conjunction with the dual reporter receptor system to generate tissues containing fibroblasts and HMSC cells. The fibroblasts contain the dual receptor reporter amphiphatic molecule and the HMSC cells will not be modified. Upon mixing no spheroids or tissue like structures form, however, upon introduction of the RGD-complementary functional group-containing peptide the fibroblasts become fluorescent and form spheroids with itself and HMSC cells. These new tissues are then examined for changes in HMSC differentiation lineages (e.g. adipocytes, fibroblasts, osteoblasts, and/or chondrocytes) by addition of the appropriate induction media.

Electroactive Moieties

Engineered cells that are electroactive (bioelectronics) allow very sensitive electrochemical analytical techniques to probe and control cell behaviour. Generating electroactive cell surfaces immediately allows for cells to be manipulated by many bioanalytical methods and provides a continuous redox status of the changing local cell environment.

Cell surfaces can be rewired via an electroactive molecule for dynamic control of cell surface ligands and cell tissue interactions (FIGS. 12-15). This methodology allows for the modulation of cell-cell interactions to generate three-dimensional (3D) tissue structures applied to stem cell, cell-surface tailoring, and/or tissue engineering.

To study most cells in vitro it is desirable for cells to adhere to surfaces for cell culture expansion and for interrogation by fluorescently based microscopy staining and imaging techniques. Since most studied cells are adherent it is advantageous to study cell behaviour on a material that also is conductive. These materials are like a working electrode and can be modified with many different proteins and small molecules to induce cell adhesion and proliferation. The classic example is a gold surface presenting molecules in the form of self-assembled monolayers. Engineering cells to have electroactive and bio-orthogonal capabilities presents many new ways to analytically study and control cell behaviour when adhered to conducting substrates. As a representative example, the electroactive hydroquinone system is used to study the biophysics of membrane diffusion on a cell's surface and to conjugate and release cell-cell assemblies while adhered to a working electrode. Hydroquinone containing stem cells (HQ-HMSCs) are adhered to patterned gold electrodes at the size of single cells (20×20 microns). Since the hydroquinone form is in the off state (not a ketone and therefore not bio-orthogonal) the adhered HQ-HMSC cell will not react with fluorescent-oxyamine containing molecules in solution. When activated, (i.e. an electrical potential is applied to the gold substrate) and the HQ-HMSC converts to the quinone form (quinone is a ketone which is now bio-orthogonal and will react with oxyamine molecules in solution). It is noteworthy that only the hydroquinone molecules that are in close proximity to the gold surface will be converted to quinones. These quinones will immediately react with fluorescent oxyamines in solution and diffuse on the cell membrane. These events are monitored, for example, by TIRF microscopy and electrochemistry simultaneously and provide an unprecedented view of membrane diffusion events. This system is used, for example, to explore the differences in lipid diffusion depending on the fluidity of the membrane as a function of stem cell differentiation. Furthermore, a major challenge in stem cell plasticity model systems is that after co-culture tissue formation and stem cell differentiation, the cell lines are separated to study the newly differentiated stem cells. Co-culture tissues are generated between HMSC's and fibroblasts on working electrodes and after differentiation occurs the cells are separated by a simple electrochemical pulse that cleaves all the associations between the cells. Therefore, the electroactive engineered cells allow for co-culture tissue formation (bio-orthogonal) but also the on-demand electrical release of the cells. Preliminary data shows that the brief low potential electrochemical pulse does not alter cell viability. These types of studies are easily adapted to generate tissue arrays on gold fabricated microelectrodes and provide new biotechnologies to understand the role of temporal associations between cell types for a range of autocrine and paracrine signaling.

Tissue Building Using Polymer Scaffolds

Generating implantable biomaterials often involves the interaction of cells with non-natural materials and polymers. In a further embodiment, the surface modified cells generated using a method of the present application are combined with polymers and beads that contain complementary bio-orthogonal functional groups to generate new living biomaterials and hybrid polymer-multi-layer tissues with control of 3D architecture and vasculature. In this embodiment, tailored cells interact with tailored materials for example, for a range of stem cell-based biotechnology and tissue engineering applications.

Figure 16:
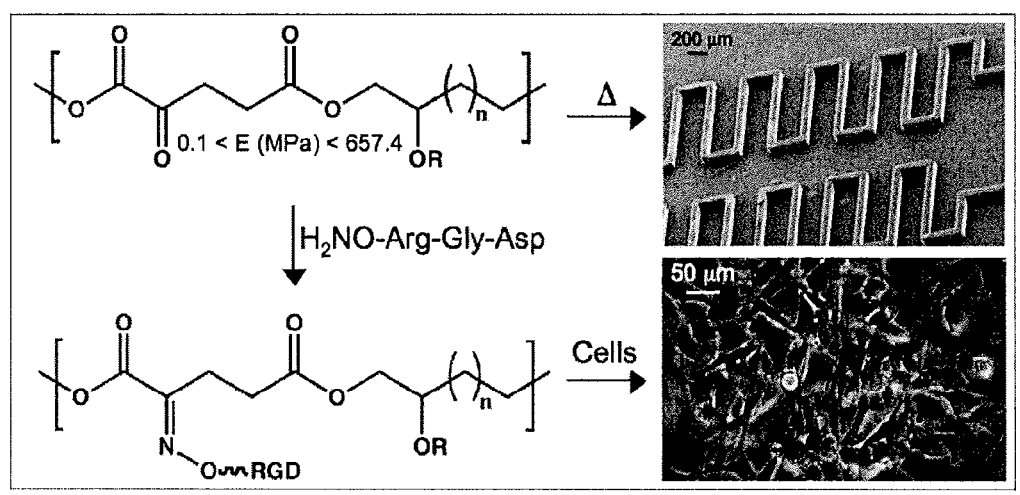
FIG. 16 shows poly(triol α-ketoglutarate) as biodegradable, chemoselective, and mechanically tunable elastomers in an exemplary embodiment of the present application. The design of several elastomers based on the thermal polycondensation of α-ketoglutaric acid and one of three triols: glycerol, 1,2,4-butanetriol, or 1,2,6-hexanetriol has been performed.[74-79] By varying the curing temperature and the duration of the curing process, a wide range of mechanical properties was achieved. The values of the Young's modulus (0.1-657.4 MPa), ultimate stress (0.2-30.8 MPa), and ultimate strain (22-583%) encompass the mechanical properties of many biological materials, increasing the probability of success for the use of poly(triol α-ketoglutarate) as a biomaterial. Furthermore, the poly(triol α-ketoglutarate) series hydrolytically degraded in as fast as 2 days and as long as 28 days in phosphate-buffered saline solutions. For post-polymerization modifications, the repeat units contain ketones, which are capable of reacting with a variety of oxyamine-terminated molecules to generate stable oxime linkages. Finally, the versatility and utility of these elastomers were demonstrated by creating micro-patterned structures and films for biospecific cell scaffold supports.

Several reports exist that highlight the development and use of polyketoesters as biodegradable biomaterials (FIG. 16).[74-79] These materials are non-cytotoxic, can be functionalized post polymerization and are compatible with cell culture. Furthermore, these polymers were implanted into rabbits and a complete blood and histology analysis was performed. These biodegradable polymers comprise a polyester backbone and a repeating ketone unit. The ketone group allows for bio-orthogonal oxime ligation which allows the integration of these polymers with the surface modified cell lines of the present application to generate hybrid living tissue-polymer biomaterials.

Accordingly, in another embodiment, polyketoester polymers are incorporated with the surface modified cells of the present application. For example, fibroblasts are generated that contain oxyamine groups these cells are seeded onto the polyketoester polymers. A covalent oxime ligation occurs between the cells and the polymers. The addition of HMSC cells with ketone groups then attaches to the fibroblast oxyamine cells. In this manner complex multi-cell type polymer hybrids are built. These living biomaterials are assessed for long-term stability and compatibility for implantable polymer devices. Furthermore, spheroid clusters of cells are generated based on the surface-modified cells of the present application and these clusters are seeded on to the polyketoester polymers. This allows for rapid seeding and dense tissue formation and a new way to generate dense cell coverage on materials that currently take many weeks of cell seeding to a polymer scaffold—followed by long term bioreactor growth. This system is used in bioreactor technology to enable a rapid method to seed dense clusters of cells to scaffolds. In a further embodiment, biodegradable polymer beads containing ketone groups are mixed with oxyamine presenting fibroblasts and ketone presenting HMSC cells. The cells covalently attach to each other and to the beads and dense tissues are formed with the beads encapsulated within the tissue. Over time the beads degrade and provide space for re-alignment or the generation of blood vessels within the tissue. This system is used to study tissue formation of blood vessels and as a potential method to screen drugs to inhibit the formation of these architectures. This particular strategy is general and provides new types of living biomaterial hybrids and new implantable tissue scaffolds for a range of transplantation and tissue engineering applications.

The present application also includes cell populations whose surfaces have been modified with reactive functional groups by fusion with the liposomes of type A and/or B, compositions comprising these cell populations and all uses thereof.

VI. Method for Simultaneous Transfection and Cell Surface Modification

In yet another embodiment, liposomes comprising one or more amphiphatic molecules having at least one of a functional group pair, are combined with one or more nucleic acid molecules to form a nucleic acid-liposome complex. These complexes, when delivered to cells result in simultaneous transfection of the cells with the nucleic acid molecule(s) and modification of the cell's surface with at least one of a complementary functional group pair. The transfected and cell surface modified cells can then undergo subsequent cell-cell assembly or reaction, for example, with a range of ligands, small molecules and proteins via bio-orthogonal ligation.

Accordingly, the present application also includes a method for the simultaneous transfection of one or more nucleic acid molecules into a cell and modification of the cell's membrane comprising:

(a) combining the one or more nucleic acid molecules with a liposome under conditions to form a liposome-nucleic acid complex wherein the liposome comprises one or more amphiphatic molecules; and (b) contacting the cell with the liposome-nucleic acid complex under conditions to simultaneously transfect the cell with the one or more nucleic acid molecules and incorporate the one or more compounds into the cell membrane, wherein the one or more amphiphatic molecules are selected from a compound of Formula V:

wherein $R^2$ and $R^3$ are each, independently selected from

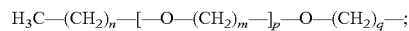

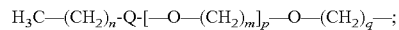

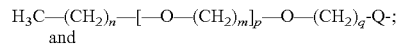

and

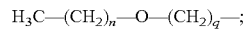

n is 5, 6, 7, 8, 9, 10, 11, 12, 13, 14, 15, 16, 17, 18, 19, 20, 21, 22, 23, 24, 25, 26, 27, 28 or 29;
m is 1, 2, 3, or 4;
p is 1, 2, 3, 4, 5, 6, 7, 8, 9 or 10;
q is 0, 1, 2, 3 or 46;
Q comprises at least one of a fluorescent moiety, an electroactive moiety, a photocleavable moiety, a radioactive moiety, a chelating moiety and a spin label; r and r' are each independently, 1, 2 or 3; and X and X' are each, independently, one of a complementary functional group pair; and
a compound of Formula VI:

$$R^4—X \qquad (VI)$$

wherein $R^4$ is selected from:

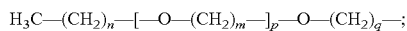

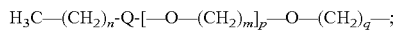

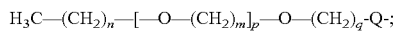

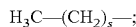

n is 5, 6, 7, 8, 9, 10, 11, 12, 13, 14, 15, 16, 17, 18, 19, 20, 21, 22, 23, 24, 25, 26, 27, 28 or 29;
m is 1, 2, 3, or 4;
p is 1, 2, 3, 4, 5, 6, 7, 8, 9 or 10;
q is 0, 1, 2, 3, 4, 5 or 6;
s is 6, 7, 8, 9, 10, 11, 12, 13, 14, 15, 16, 17, 18, 19, 20, 21, 22, 23, 24, 25, 26, 27, 28 or 30;
Q comprises at least one of a fluorescent moiety, an electroactive moiety, a photocleavable moiety, a radioactive moiety, a chelating moiety and a spin label; and
X is one of a complementary functional group pair.

The present application also includes the use of one or more compounds of Formula V or VI, or liposomes comprising one or more of the compounds of Formula V or VI, for simultaneous transfection of one or more nucleic acid molecules into a cell and modification of the cell's membrane.

In an embodiment, the conditions to form a liposome-nucleic acid complex comprise contacting positively charged liposomes of the present application with the nucleic acid in, for example, aqueous solution, at a temperature of about 20° C. to about 30° C. for about 5 min to about an hour. In an embodiment, the weight ratio of the liposome to nucleic acid is about 200:1 to about 75:1

In another embodiment, the conditions to simultaneously transfect the cell with the one or more nucleic acid molecules and incorporate the one or more compounds of Formula V or VI into the cell membrane comprise contacting the liposome-nucleic acid complex with a suitable culture medium in which the cells have been growing (for example have reached about 50% to about 90% confluency) for about one hour to about 48 hours. In culture the weight ratio of the liposomes to nucleic acid is about 20:1 to about 5:1.

Figure 22:
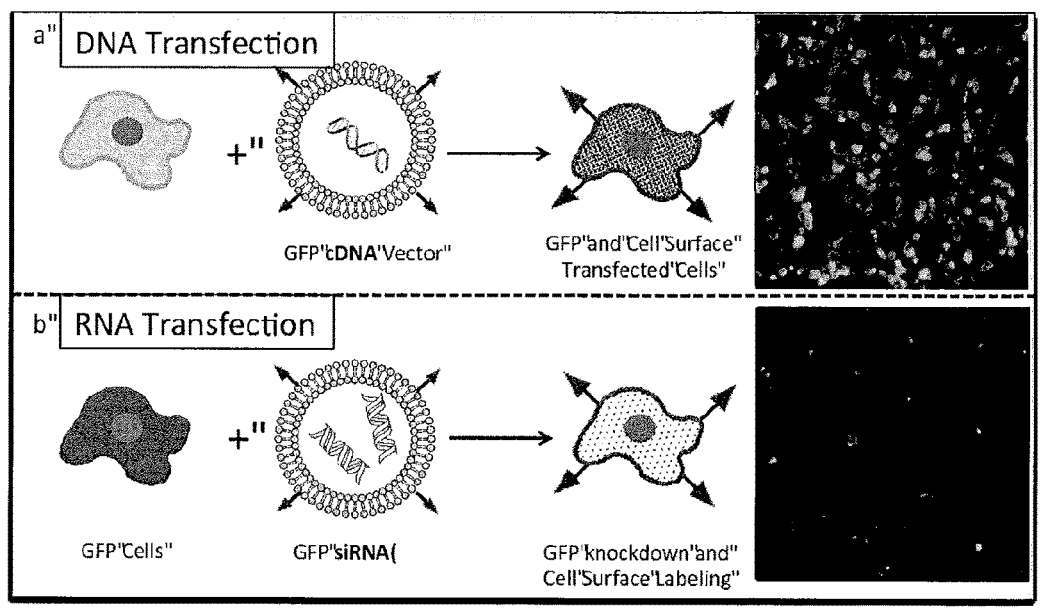
FIGS. 22a and 22b show a general schematic and imaging of cells transfected with either DNA or siRNA via the bio-orthogonal liposome fusion method in an exemplary embodiment of the present application. In (a), Swiss 3T3 Albino fibroblasts were transfected with Green Fluorescent Protein (GFP) resulting in fluorescent cells. In (b) GFP-expressing fibroblasts lost their fluorescence upon transfection with GFP siRNA.

The transfected and cell surface modified cells can undergo subsequent cell-cell assembly or reaction with a range of ligands, small molecules, proteins via bio-orthogonal reactions or ligation (see FIG. 22).

In an embodiment, X in the compounds of Formula V or VI is selected from a functional group comprising a ketone, an oxyamine, a hydrazine, a diene, a dienophile, an azide and an alkyne. In another embodiment, X in the compounds of Formula V or VI is selected from a functional group comprising a ketone, an oxyamine, an aldehyde, an amine, a hydrazine, a diene, a dienophile, an azide and an alkyne. It another embodiment, the complementary functional group pair in the compounds of Formula V or VI is a ketone and an oxyamine which react to form an oxime. Accordingly, it is an embodiment, that X is —C(O)$R^1$, wherein $R^1$ is $C_{1-2}$alkyl, or O—$NH_2$.

In a further embodiment of the application, the complementary functional group pair is a aldehyde and an amine which when contacted with each other, form a stable imine bond. Accordingly, in an embodiment of the application, X in the compounds of Formula V or VI is, independently, C(O)H or X in the compounds of Formula V or VI is $NH_2$. In another embodiment of the application, X and X' in the compounds of Formula V or VI are, independently, C(O)H or X and X' in the compounds of Formula V or VI are, independently, $NH_2$.

In an embodiment, n in the compounds of Formula VI is 8, 9, 10, 11, 12, 13, 14, 15, 16, 17, 18, 19, 20, 21, 22, 23, 24, 25, 26, 27, 28 or 29.

In an embodiment, s in the compounds of Formula VI is 8, 9, 10, 11, 12, 13, 14, 15, 16, 17, 18, 19, 20, 21, 22, 23, 24, 25, 26, 27, 28 or 29

In another embodiment, m in the compounds of Formula VI is 2 or 3.

In another embodiment, p in the compounds of Formula VI is 4, 5, 6, 7, 8, 9 or 10.

In another embodiment, q in the compounds of Formula VI is 1, 2, 3 or 4.

As noted above, Q in the compounds of Formula VI is group that comprises at least one of a fluorescent moiety, an electroactive moiety, a photocleavable moiety, a radioactive moiety, a chelating moiety and a spin label. In an embodiment, Q in the compounds of Formula VI is a group that comprises at least one of a fluorescent moiety, an electroactive moiety and a photocleavable moiety. In an embodiment, the fluorescent moiety is a calcein or rhodamine or fluorescein moiety. In another embodiment, the electroactive moiety (hydroquinone or ferrocene). In a further embodiment, the photocleavable moiety is a 4-(1-hydroxyethyl)-2-methoxy-5-nitrophenoxy moiety.

In the compounds of Formula V, it is an embodiment that $R^2$ and $R^3$ are independently selected from:

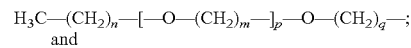
and

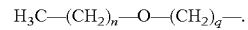

In a further embodiment, $R^2$ and $R^3$ in the compounds of Formula V are independently $H_3C$—$(CH_2)_n$—[—O—$(CH_2)_m$—$]_p$—O—$(CH_2)_q$—. In a further embodiment, $R^2$ and $R^3$ in the compounds of Formula V are both $H_3C$—$(CH_2)_n$—[—O—$(CH_2)_m$—$]_p$—O—$(CH_2)_q$—.

In an embodiment, n in the compounds of Formula V, is 8, 9, 10, 11, 12, 13, 14, 15, 16, 17, 18, 19, 20, 21 or 22.

In another embodiment, m in the compounds of Formula V is 2 or 3.

In another embodiment, p in the compounds of Formula V is 4, 5, 6, 7, 8, 9 or 10.

In another embodiment, q in the compounds of Formula V is 1 or 2.

In another embodiment of the application, X and X' in the compounds of Formula V are both C(O)$R^1$, wherein $R^1$ is $C_{1-2}$alkyl, or X and X' in the compounds of Formula V are both O—$NH_2$. In another embodiment of the application, X and X' in the compounds of Formula V are both C(O)H or X and X' in the compounds of Formula V are both $NH_2$. In another embodiment of the application, X and X' in the compounds of Formula V are both C(O)H.

In another embodiment of the application, r and r' in the compounds of Formula V are 1 or 2.

In a further embodiment, the compound of Formula VI is selected from:

$CH_3(CH_2)_{10}$—$[OCH_2CH_2]_3OCH_2C(O)CH_3$; (Ia)
$CH_3(CH_2)_{10}$—$[OCH_2CH_2]_4OCH_2CH_2CH_2SH$; (Ib)
$CH_3(CH_2)_{10}$—$[OCH_2CH_2]_3OCH_2CH_2ONH_2$; (Ic)
$CH_3(CH_2)_{10}$—$[OCH_2CH_2]_4OCH_2C\equiv CH$; (Id)
$CH_3(CH_2)_{10}$—$[OCH_2CH_2]_4OCH_2N_3$; (Ie)
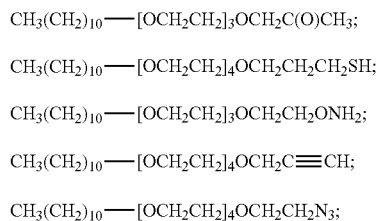
(If)
$CH_3(CH_2)_{10}$—$[OCH_2CH_2]_4OCH_2CH_2NH$—$NH_2$; (Ig)
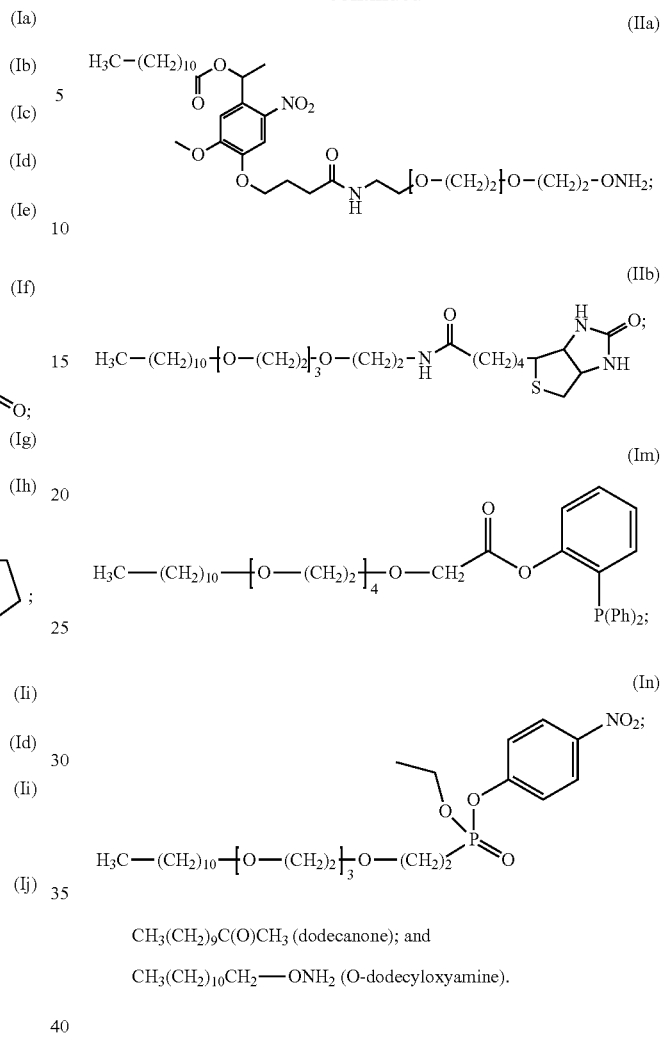
$CH_3(CH_2)_9C(O)CH_3$ (dodecanone); and
$CH_3(CH_2)_{10}CH_2$—$ONH_2$ (O-dodecyloxyamine).
In another embodiment of the compound of Formula V is selected from
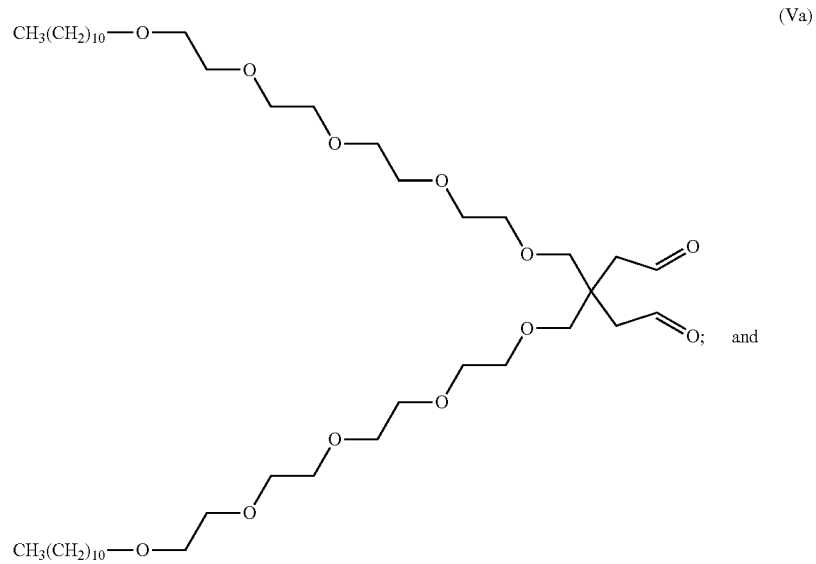

-continued (Vb)

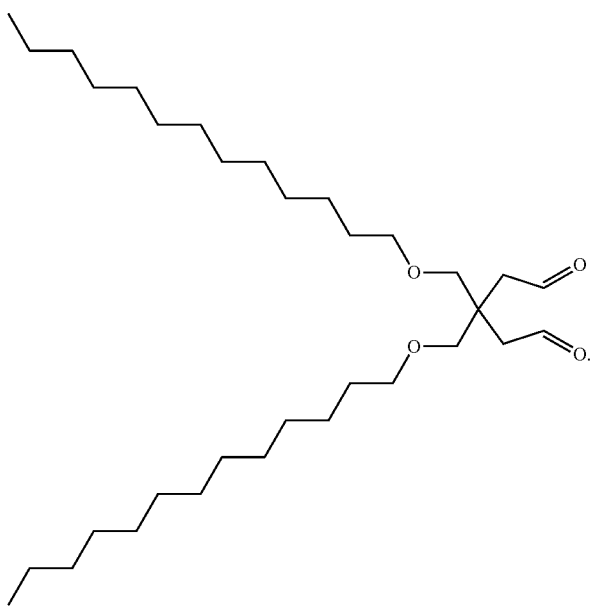

EXAMPLES

Materials and Methods

Egg palmitoyl-oleoyl phosphatidylcholine (egg-POPC) was purchased from Avanti Polar Lipids (Alabaster, Ala.), and all other chemicals were obtained from Sigma-Aldrich or Fisher. Swiss 3T3 albino mouse fibroblasts were obtained from the Tissue Culture Facility at the University of North Carolina (UNC). Human mesenchymal stem cells (hMSCs), basic medium, growth medium and differentiation medium were obtained from Lonza.

The following non-limiting examples are illustrative of the present application:

The photolabile molecule was prepared based on the synthetic protocols of similar molecules in the literature.[56-58] The synthetic scheme is shown below in Scheme 1.

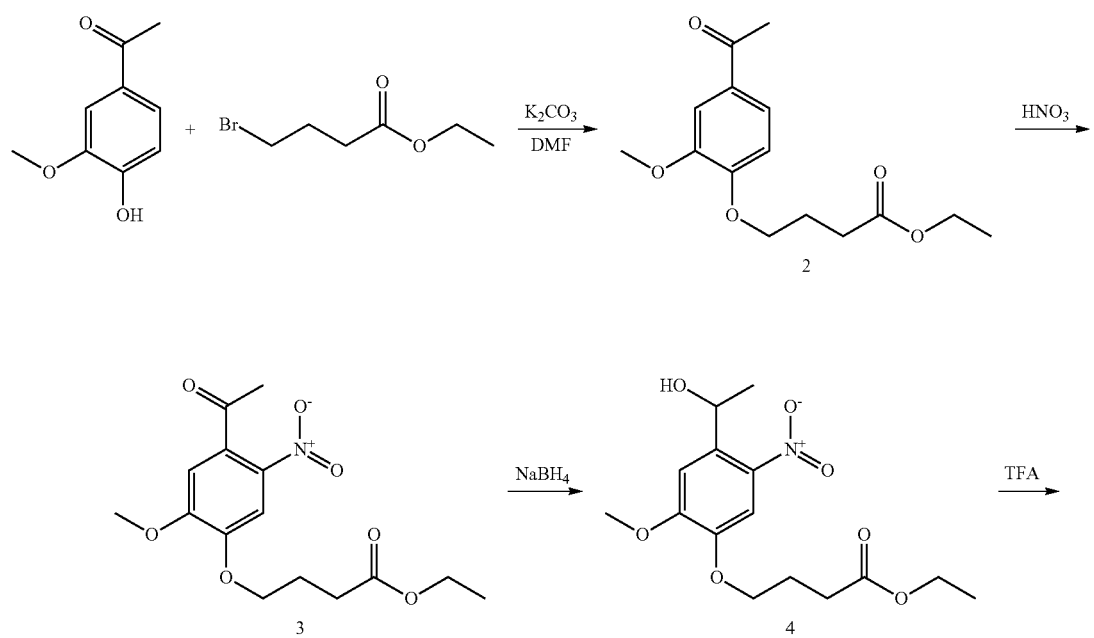

-continued
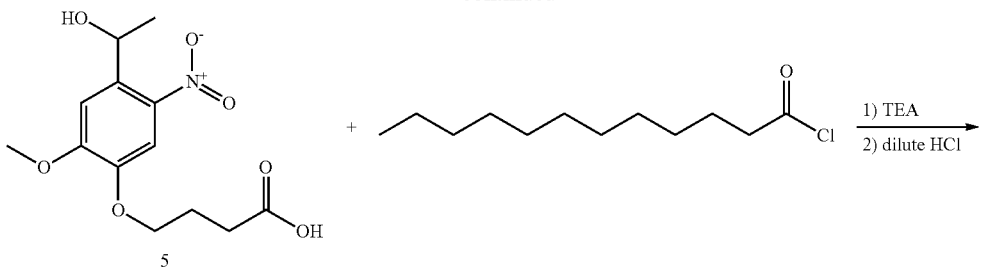
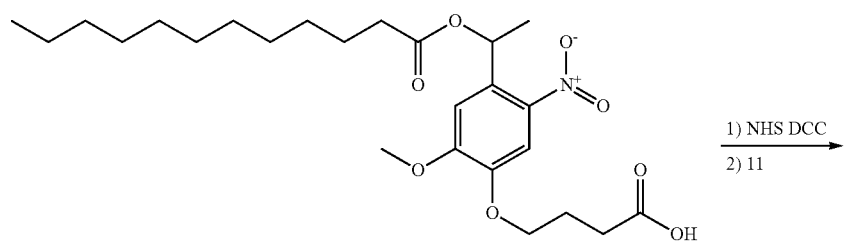
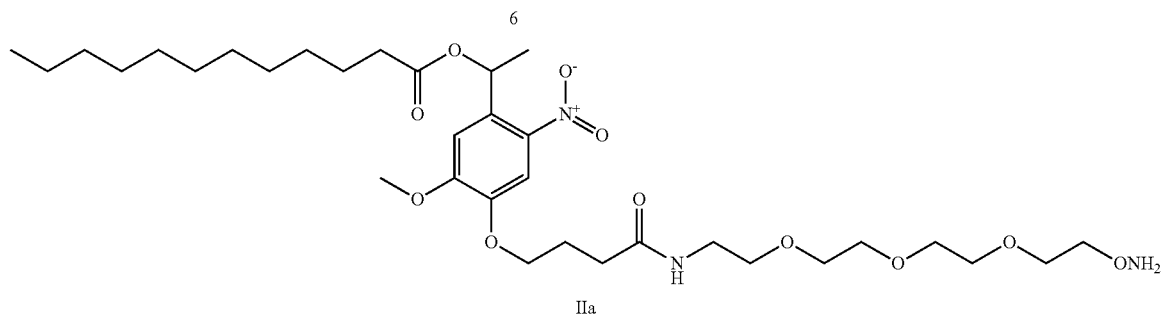
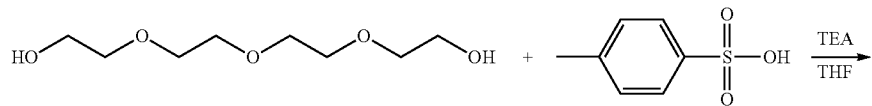
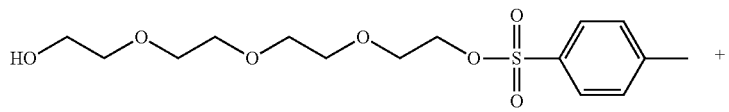
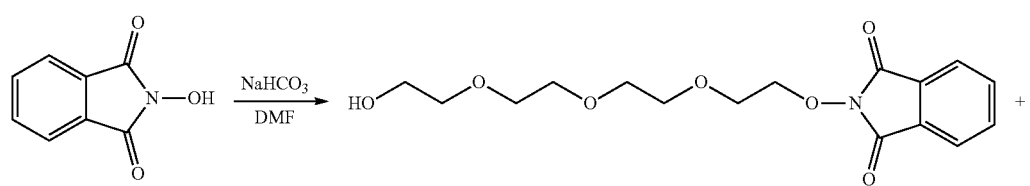
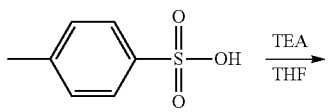
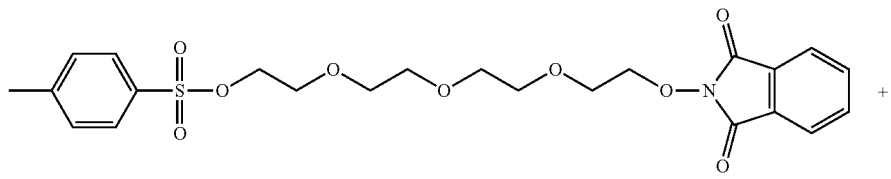

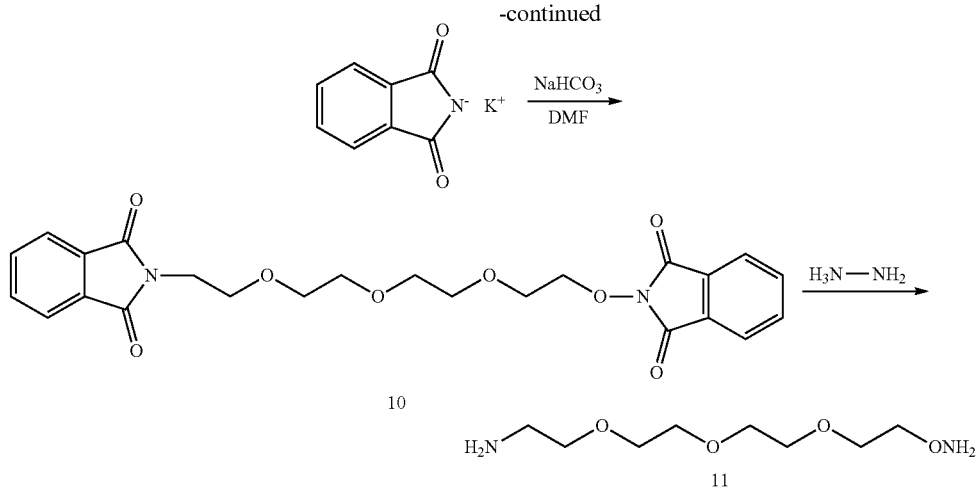

Example 1: Preparation of a Photolabile Amphiphatic Molecule (IIa)

(a) ethyl 4-(4-(1-hydroxyethyl)-2-methoxy-5-nitrophenoxy)butanoic acid (5)

In an Ar-purged flask with stir bar, acetovanillone and ethyl 4-bromobutyrate were dissolved in dimethyl formamide, and excess potassium carbonate was added. The reaction mixture was stirred overnight, precipitated in water, and filtered. The alkylated powder product (2) was subsequently nitrated with nitric acid at 0° C. for 1 h and at room temperature for 1 h, carefully monitoring the temperature (≤30° C.). The product was precipitated in water, filtered, recrystallized from ethanol, and dried under vacuum overnight. The nitrated powder product (3) in ethanol was reduced with excess sodium borohydride at 38° C. The reaction was stirred overnight, precipitated in water, filtered, and dried under vacuum. The alcohol powder product (4) was finely ground and reacted with aqueous trifluoroacetic acid (TFA) at 90° C. overnight. Additional TFA was added until reaction completion was verified by thin layer chromatography (10:1, methylene chloride:acetone). The reaction mixture was cooled, filtered, and dried under vacuum overnight. The product was purified by chromatography (10:1, methylene chloride:methanol). $^1$H NMR (($CD_3$)$_2$SO): δ=12.2 (s, $CH_2CO_2H$), δ=7.5 (s, Aromatic-H), δ=7.3 (s, Aromatic-H), δ=5.2 (m, Aromatic-$CH(CH_3)OH$), δ=4.1 (t, Aromatic-$OCH_2CH_2CH_2CO_2H$), δ=3.9 (s, Aromatic-$OCH_3$), δ=2.4 (t, Aromatic-$OCH_2CH_2CH_2CO_2H$), δ=2.0 (m, Aromatic-$OCH_2CH_2CH_2CO_2H$), and δ=1.3 (d, Aromatic-$CHCH_3$).

(b) 4-(4-(1-(dodecanoyloxy)ethyl)-2-methoxy-5-nitrophenoxy)butanoic acid (6)

The photolabile precursor 5 (0.01 mol) was suspended in anhydrous DCM (1.4 mol) and stirred in a flask purged with Ar. TEA (0.03 mol) was added, and lauroyl chloride (0.025 mol) in anhydrous DCM (0.3 mol) was added dropwise at 0° C. The reaction was stirred at room temperature overnight and subsequently washed with sodium bicarbonate (5 w/v % aq.), dilute hydrochloric acid (1 v/v % aq.), and DI water. The product was purified by flash chromatography (10:1, methylene chloride:acetone).

$^1$H NMR ($CDCl_3$): δ=12.2 (s, $CH_2CO_2H$), δ=7.6 (s, Aromatic-H), δ=7.0 (s, Aromatic-H), δ=6.4 (q, Aromatic-$CH(CH_3)OC(=O)C_{11}H_{23}$), δ=4.1 (t, Aromatic-$OCH_2CH_2CH_2CO_2H$), δ=3.9 (s, Aromatic-$OCH_3$), δ=2.4 (t, Aromatic-$OCH_2CH_2CH_2CO_2H$), δ=2.3 (m, Aromatic-$CH(CH_3)OC(=O)CH_2C_{10}H_{21}$), δ=2.1 (m, Aromatic-$OCH_2CH_2CH_2CO_2H$), δ=1.6 (d, Aromatic-$CHCH_3$), δ=1.1-1.3 (m, Aromatic-$CH(CH_3)OC(=O)CH_2C_9H_{18}CH_3$), δ=0.8 (m, Aromatic-$CH(CH_3)OC(=O)C_{10}H_{20}CH_3$).

(c) 2-(2-(2-(2-hydroxyethoxy)ethoxy)ethoxy)ethyl 4-methylbenzenesulfonate (7)

In an Ar-purged flask with stir bar, tetra(ethylene glycol) (77 mmol) and triethylamine (TEA) (90 mmol) were dissolved in anhydrous THF (50 ml), and then a THF solution of 4-toluenesulfonyl chloride (26 mmol) was added dropwise over 30 min. The reaction mixture was stirred at room temperature overnight, filtered, dried under vacuum, and purified by column chromatography.

$^1$H NMR ($CDCl_3$): δ=7.78 (d, Aromatic-H), δ=7.32 (d, Aromatic-H), δ=4.16 (t, Aromatic-$SO_3CH_2CH_2O$), δ=3.56-3.72 (m, Aromatic-$SO_3CH_2(CH_2OCH_2)_3CH_2OH$). δ=2.45 (s, Aromatic-$CH_3$), δ=2.08 (s, —$CH_2OH$).

(d) 2-(2-(2-(2-(2-hydroxyethoxy)ethoxy)ethoxy)ethoxy)isoindoline-1,3-dione (8)

To a mixture of N-hydroxyphthalimide (60 mmol) and sodium bicarbonate (60 mmol) in DMF (30 ml), 7 (19 mmol) was added. The reaction mixture was kept at 80° C. and stirred overnight. The mixture was filtered and washed with DCM, dried under high vacuum, and purified by column chromatography.

$^1$H-NMR ($CDCl_3$): δ=7.80 (m, Aromatic-H), δ=7.69 (m, Aromatic-H), δ=4.34 (t, Phthalimide-$OCH_2CH_2$), δ=3.81, (t, Phthalimide-$OCH_2CH_2O$), δ=3.56-3.72 (m, Phthalimide-$OCH_2CH_2O(CH_2CH_2O)_3H$

(e) 2-(2-(2-(2-(1,3-dioxoisoindolin-2-yloxy)ethoxy)ethoxy)ethoxy)ethyl 4-methylbenzenesulfonate (9)

In an Ar-purged flask with stir bar, 8 (15 mmol) and triethylamine (TEA) (15 mmol) were dissolved in anhydrous THF (20 ml), and 4-toluenesulfonyl chloride (30 mmol) was added. The reaction mixture was stirred at room temperature overnight, filtered, and dried under vacuum. The crude product was dissolved in ethyl acetate and extracted with saturated NH₄Cl, brine, evaporated under vacuum, and purified by column chromatography.

$^1$H-NMR (CDCl$_3$): δ=7.80 (m, Aromatic-H), δ=7.78 (d, Aromatic-H), δ=7.69 (m, Aromatic-H), δ=7.32 (d, Aromatic-H), δ=4.34 (t, Phthalimide-OCH$_2$CH$_2$), δ=4.16 (t, Aromatic-SO$_3$CH$_2$CH$_2$O), δ=3.81, (t, Phthalimide-OCH$_2$CH$_2$O), 3.50-3.68 (m, Phthalimide-OCH$_2$CH$_2$OCH$_2$CH$_2$OCH$_2$CH$_2$OCH$_2$CH$_2$SO$_3$), δ=2.45 (s, Aromatic-CH$_3$)

(f) 2-(2-(2-(2-(2-(1,3-dioxoisoindolin-2-yl)ethoxy)ethoxy)ethoxy)ethoxy)isoindoline-1,3-dione (10)

To a mixture of potassium phthalimide (30 mmol) and sodium bicarbonate (30 mmol) in DMF (20 ml), 9 (11 mmol) was added. The reaction mixture was kept at 80° C. and stirred overnight. The mixture was filtered and washed with DCM, extracted with saturated NH$_4$Cl, brine, dried under vacuum, and purified by column chromatography. $^1$H-NMR (CDCl$_3$): δ=7.78-7.83 (m, Aromatic-H), δ=7.66-7.72 (m, Aromatic-H), δ=4.34 (t, Phthalimide-OCH$_2$CH$_2$), δ=3.48-3.83, (t, Phthalimide-OCH$_2$(CH$_2$OCH$_2$)$_3$CH$_2$ (g) 2-(2-(2-(2-(aminooxy)ethoxy)ethoxy)ethoxy)ethanamine (11)

To a solution of 10 (8 mmol) in DCM, excess hydrazine was added. The reaction was kept under room temperature and stirred overnight. The resulting product was filtered and dried under vacuum.

$^1$H-NMR (CDCl$_3$): δ=3.79 (t, H$_2$NO—CH$_2$CH$_2$O), δ=3.46-3.65 (m, H$_2$NOCH$_2$(CH$_2$OCH$_2$)$_3$CH$_2$NH$_2$, δ=2.83 (t, H$_2$NCH$_2$CH$_2$O).

(h) 1-(4-(1-(aminooxy)-13-oxo-3,6,9-trioxa-12-azahexadecan-16-yloxy)-5-methoxy-2-nitrophenyl)ethyl dodecanoate (IIa)

To a DMF solution of N-hydroxysuccinimide (NHS) (0.005 mol) and 6 (0.002 mol), a DMF solution of DCC (0.005 mol), was added dropwise at 0° C. The mixture was stirred overnight, vacuumed, dissolved with DCM, filtered, purified by chromatography (10:1, methylene chloride:acetone). The product was then added to the DCM solution of 11 (0.02 mol). The mixture was stirred at room temperature overnight, and subsequently filtered, purified by flash chromatography (10:1, methylene chloride:methanol).

$^1$H NMR (CDCl$_3$): δ=7.55 (s, Aromatic-H), δ=6.95 (s, Aromatic-H), δ=6.4 (q, Aromatic-CH(CH$_3$)OC(=O)C$_{11}$H$_{23}$), δ=4.05 (t, Aromatic-OCH$_2$CH$_2$CH$_2$CO$_2$H), δ=3.9 (s, Aromatic-OCH$_3$), δ=3.8 (t, —CH$_2$ONH$_2$), δ=3.55-3.75 (m, —OCH$_2$CH$_2$OCH$_2$CH$_2$OCH$_2$CH$_2$ONH$_2$), δ=3.5 (t, —(C=O)NHCH$_2$CH$_2$OCH$_2$CH$_2$). δ=3.4 (t, —(C=O)NHCH$_2$CH$_2$OCH$_2$CH$_2$), δ=2.4 (t, Aromatic-OCH$_2$CH$_2$CH$_2$(C=O)NH), δ=2.3 (m, Aromatic-CH(CH$_3$)OC(=O)CH$_2$C$_{10}$H$_{21}$), δ=2.15 (m, Aromatic-OCH$_2$CH$_2$CH$_2$(C=O)NH), δ=1.6 (d, Aromatic-CHCH$_3$), δ=1.1-1.3 (m, Aromatic-CH(CH$_3$)OC(=O)CH$_2$C$_9$H$_{18}$CH$_3$), δ=0.8 (m, Aromatic-CH(CH$_3$)OC(=O)C$_{10}$H$_{20}$CH$_3$).

Example 2: Liposome Preparation

Liposomes were prepared as previously reported. To generate photo-oxyamine or ketone liposomes, photo-oxyamine IIa or dodecanone (2) (60 μL, 10 mM solution in CHCl$_3$) were dissolved with egg-POPC (450 μL, 10 mg/mL in CHCl$_3$) and 1,2-dioleoyl-3-trimethylammonium-propane (DOTAP, 10 μL, 10 mg/mL in CHCl$_3$) in chloroform followed by concentration under high vacuum for 4 h. The dried lipid samples were then reconstituted and brought to a final volume of 3 mL in PBS buffer, pH 7.4. The contents of the vial were warmed to 50° C. and sonicated for 20 min, in a tip sonicator, until the solution became clear, and liposomes containing photo-oxyamine or ketone groups were formed.

Example 3: Cell Culture

Human mesenchymal stem cells (hMSCs) were cultured as instructed by the vendor. After cells were washed with PBS and trypsinized for 3-5 minutes, they were centrifuged in serum containing medium and followed with gentle resuspending in serum-free medium. The cells were then seeded onto transparent glass substrates and then incubated at 37° C. in a humidified atmosphere of 5% CO$_2$ overnight. Adipogenic differentiation was induced by adipogenic induction medium and kept by induction/maintenance cycles as described in the Lonza protocol. Osteogenic differentiation was induced by osteogenic induction medium provided by Lonza.

Example 4: Immunohistochemistry

The substrates for confocal imaging were fixed with formaldehyde (3.2% in PBS) and permeated (PBS containing 0.1% Triton X-100). A fluorescent dye mixture, containing phalloidin-TRITC (actin) and DAPI (nucleus) was then made in PBS containing 5% normal goat serum and 0.1% Triton X-100. Cells were incubated with the dye solution for 2 h. The substrates were then secured in fluorescence mounting medium (Dako, Carpinteria, Calif., USA), which enhances the visualization of cells when viewed under a fluorescent microscope with a glass cover slip. The substrates for adipogenic differentiation were washed by PBS and fixed in 3.2% formaldehyde for 30 minutes, followed with sterile water and 60% isopropanol for 5 minutes. Samples were then stained by Oil Red O for 5 minutes followed by Harris Hematoxylin for 1 minute. The substrates for collagen differentiation were fixed with formaldehyde and permeated with 0.1% Triton X-100. Monoclonal antibody of collagen I was applied for 1 h, then incubated with secondary antibody anti-mouse IgG (FITC conjugate) for 30 min, and followed with DAPI for 30 min for nucleus staining. The substrates for osteogenic differentiation were stained with sigmal Alkaline Phosphatase (ALP) kit (sigmal kit 85).

Example 5: RT-PCR Analysis

Human mesenchymal stem cells (hMSCs) were induced to differentiation for 2 weeks. Total RNA was then extracted by RNA isolation kits (Qiagen). 1 μg of total RNA was converted to cDNA using AMV reverse transcriptase and random hexamer primers (Promega). The resulting cDNA was used in PCR with the following primer, LPL (sense 5'-GAG ATT TCT CTG TAT GGC ACC-3', antisense 5'-CTG CAA ATG AGA CAC TTT CTC-3'), PPARγ2 (sense 5'-GCT GTT ATG GGT GAA ACT CTG-3', antisense 5'-ATA AGG TGG AGA TGC AGG CTC-3'), Collagen I (sense 5'-TGC TGG CCA ACC ATG CCT CT-3', antisense 5'-TTG CAC AAT GCT CTG ATC-3'), Collagen II (sense 5'-ATG ACA ACC TGG CTC CCA AC-3', antisense 5'-GCC CTA TGT CCA CAC CGA-3'), RUNX2 (sense 5'-GAT GAC ACT GCC ACC TCT GAC TT-3', antisense 5'-CCC CCC GGC ACC ATG GGA AAC TG-3'), ALPL (sense 5'-CCA TTC CCA CGT CTT CAC ATT-3, antisense 5'-GAG GGC CAG CGC GAG CAG CAG GG-3'), at annealing temperatures of 52° C., 55° C., 53° C., 57° C., 61° C., 66° C., respectively. Amplification reactions were carried out for 1 minute through 30 cycles, and the reaction products were subjected to 1% agarose gel electrophoresis. The reaction products are 276 bp (Lpl), 351 bp (PPARγ2), 489 bp (Collagen I), 359 bp (Collagen II), 362 bp (RUNX2), and 418 bp (ALPL) respectively.

Example 6: Confocal Microscopy

Cell clusters and tissue formation were visualized with a Nikon Eclipse TE2000-E inverted microscope (Nikon USA, Inc., Melville, N.Y.). Data was analyzed by Metamorph software and a spectral confocal microscope (LeicaMicrosystems, Bannockburn, Ill.). Three-dimensional reconstructions of fluorescent images were generated using Volocity software.

Example 7: Flow Cytometry

Fluorescence-activated cell sorting (FACS) analysis was performed to quantify the approximate number of photo-oxyamine lipids at the cell surface after membrane fusion. Liposomes were cultured with Fbs (3 mM in tris buffer, 400 μL added to 4 mL) to present photo-active group on cell surface (Jurkat cells). Ketone-conjugated fluorescein was then reacted with the surface-modified cells (0.15 mM in tris buffer, 2 h). This time course assay was conducted to determine whether the chemistry was being carried on after cell growth and division. A control cell population (not displaying photolabile lipids) was incubated with the ketone-fluorescein (0.15 mM in tris buffer, 2 h). After culturing for the appropriated time, the different cell populations were washed with PBS (3×5 mL), trypsinized (1 mL, 5 min, 37° C., 5% $CO_2$), centrifuged (5 min, 1000 rpm), resuspended in RPMI (without phenol red), centrifuged (5 min, 1000 rpm), and resuspended in RPMI (~$10^7$ cells/2 mL). Fluorescence measurements were calibrated using RCP-5-30 beads (~$10^7$ beads/mL, Spherotech, Inc., Lake Forest, Ill.) of known fluorescein equivalent molecule density. Fluorescent intensities based on number of cells counted were compared to the standard bead and control cells lacking fluorescent molecule conjugation and approximate numbers of fluorescent compound bound to the surface was calculated. Flow cytometry was performed using a Dako CyAn ADP (Beckman-Coulter, Brea, Calif.), and data was analyzed with Summit 4.3 software. The error bars are represented as the mean fluorescence intensity SD of 3 trials.

Example 8: Matrix-Assisted Laser-Desorption/Ionization Mass Spectrometry (MALDI-MS)

Gold-coated MALDI sample plates (123×81 mm) (Applied Biosystems, Foster City, Calif.) were prepared by electron-beam deposition (Thermionics Laboratory Inc, Hayward, Calif.) of titanium (5 nm) and then gold (12 nm). In order to form self-assembled monolayers (SAM) of alkanethiolates on the plates, the slides were immersed in a 1 mM solution of 1:1 ratio mixture of 11-mercaptoundecanol and tetra(ethylene glycol)-terminated undecanethiol in EtOH for 12 h, rinsed with EtOH and dried, and then partially oxidized to aldehyde by mild oxidant pyridinium chlorochromate (PCC), as previously reported (S4, S5, S6). Once removed from solution, the surfaces were rinsed with EtOH and dried before use. Cells tailored with photolabile oxyamine group are seeded onto the SAM presenting aldehyde group to form oxime ligation between the cell membrane and gold substrate. After washing and removing the cells, the bonded residue on the gold substrate was traced by MALDI-MS. MALDI analysis was carried out using an AB SCIEX TOF/TOF™ 5800 System (Applied Biosystems, Foster City, Calif.).

Example 9: Cell Patterning

Self-assembled monolayers (SAMs) presenting aldehyde and tetra(ethylene glycol) ($EG_4$) groups were patterned at a ratio of 1:9 using microfluidic oxidation to ensure that fbs were only adhering to the patterned surface portions that presented 10% aldehyde groups. Fbs were cultured with photo-liposomes (4 h) and then seeded (~$10^2$ cells/mL, 2 h) to the patterned aldehyde surfaces. Media containing 10% calf bovine serum (CBS) and 1% penicillin/streptomycin was then added, and the substrates were incubated at 37° C. in 5% $CO_2$ for 4 d. Cells cultured with liposomes, not containing the key functional groups, did not attach to the patterned surfaces. Substrates were then imaged by brightfield microscopy with an exposure time of 400 ms.

Example 10: Comparison of Compounds of the Application with Compounds Containing Hydrophobic Linkers Flow cytometry was used to assess the amount of cell-surface conjugation that could be achieved using the compounds of the application having hydrophilic linking groups and corresponding compounds having hydrophobic linking groups. A depiction of the experimental hypothesis is shown in FIG. 1 and the results are shown in FIG. 2. From the flow cytometry data (FIG. 2A), it can been seen that cell surface conjugation was significantly greater when the hydrophilic ketone and oxyamine were utilized for liposome fusion. Cell surface conjugation was enhanced by 6.25× for the hydrophilic ketone and 7.4× for the hydrophilic oxyamine compared to their corresponding hydrophobic analogs.

Example 11: Cell Viability

Referring to FIG. 3: (A) ketone- and oxyamine-presenting Swiss 3T3 albino fibroblasts were mixed together in solution for 1, 2, 3, and 5 h, resulting in 3D spheroid formation and were then tested for viability using trypan blue dye (0.4% in PBS, 2 min). (B) Trypan blue linescans (fluorescence false-colored for enhanced visualization) of the spheroids generated after 5 h of culture were compared to a control population in which spheroids were generated for 5 h, fixed with formaldehyde, and stained with trypan blue under the same conditions. Greater than 99% of cells were determined to be viable. Similarly, 3D multi-layered tissue-like structures were generated and cultured for (C) 3 (D) 5, and (E) 7 days and tested for viability using trypan blue dye. (F) Again as a control, cells were grown in a multilayer for 7 days, then fixed with formaldehyde, and stained with trypan blue, and linescans were constructed for all samples and compared to the control. Cell viability decreased with time and number of cell layers from 3 to 5 to 7 days of culture with approximated viabilities of (C) 98, (D) 91, and (E) 84%, respectively. The scale bars represent 60 (A) and 30 μm (C-F).

Results and Discussion for Examples 1-11

As shown in FIG. 5, two or more different cell types were engineered via liposome fusion to present complementary and bio-orthogonal molecules on their cell surfaces. Upon interaction, a stable and covalent click (oxime) type reaction occurred and tissue-like assemblies were formed. After a defined period of time, tissue disassembly was remotely controlled by photo-cleavage of the intercellular ligation tether. The bottom image in FIG. 5 is a schematic showing the interfacial molecular lock and cleave sequence for conjugating and releasing cell associations. The lipid lock molecule contains both a photocleavable group and an aminooxy group for bio-orthogonal oxime ligation to ketone presenting cells. Disassociation of cell assemblies via photo-cleavage occurs upon UV illumination Remote controlled tissue disassembly proceeds by a programmed photo-initiated cleavage of the intercellular ligation tether. The features of this method are the delivery of synthetic chemical groups to cell surfaces (via liposome fusion), the intercellular oxime click ligation bond (bio-orthogonal) and a photo-cleavage site contained within the oxyamine lipid tether.

To demonstrate temporal control of tissue assembly, the complementary functional group pair was delivered to two different cell types (FIG. 6). Two liposome populations containing the photo-oxyamine lipid (IIa) and ketone lipid (Ia) respectively were generated. By mixing these lipid-like molecules with background lipids (palmitoyl-oleoyl phosphatidylcholine (POPC) and positively charged, 1,2-dioleoyl-3-trimethylammonium-propane (DOTAP)), liposomes were generated that easily fused with cell membranes to deliver the photo-oxyamine and ketone groups (FIGS. 6A-B). As a demonstration, two populations of non-adherent Jurkat cells containing the photo-oxyamine and ketone groups respectively were generated, and rapid multi-cell spheroid assemblies formed via the intercellular oxime click ligation (FIG. 6C). To show the assembly was due to the rewiring of cell surfaces, several key control experiments were performed. Upon liposome delivery without the bio-orthogonal lipids to the cells, no spheroids were generated. Liposome delivery without complementary chemistry or the delivery of the lipid groups directly (not in liposome form) also resulted in no spheroid assembly. Furthermore, no intercellular assembly occurred when cell surfaces presenting the aminooxy or ketone groups were first reacted (quenched) with complementary small molecule partners.

To generate and control the size of co-culture aggregate cell assemblies, the concentration of the mixed tailored cells in solution and duration of interaction were varied. As expected, higher concentrations of cells and longer durations resulted in larger co-culture spheroids. As an important control, cell viability studies showed no difference between cell populations that were tailored with and without functional groups via liposome fusion. Due to the photo-cleavable nature of the intercellular oxime bond, spheroid disassembly proceeded upon illumination with UV light (365 nm, 10 mW/cm$^2$, 5 min). The newly disassembled cells behaviors were indistinguishable from control cells. This strategy may allow for temporal control for a range of autocrine and paracrine signaling studies and provide new ways to study co-culture and multi-cell type associations and new co-culture screens (RNAi, small molecules, etc.).

As a further application, cells that were rewired with the photo-oxyamine were seeded onto patterned materials presenting aldehyde groups (FIG. 6D-G). Cells specifically attached to the material through the interfacial oxime bond formation bypassing non-specific associations used in regular tissue culture and native ligand-receptor based adhesion (integrin-extracellular matrix). Upon exposure to UV light (365 nm, 10 mW/cm$^2$ 5 min) the photo-oxime was cleaved and the cells detached from the substrate. This strategy allows for non-adherent cells to become adhesive to tailored materials and in combination with microfluidic technology may allow for new cell sorting, cell patterning and tissue capture/release biotechnologies.[59-60]

FIG. 6H-L shows the construction of a multi-layered tissue co-culture system based on rewiring cell surfaces via liposome fusion. Two different types of cells (hMSCs and fibroblasts), tailored with ketone and photo-oxyamine respectively, were peeled from tissue culture plates and assembled via the oxime bond formation to form a stable multi-layered tissue co-culture system. Images of the co-culture tissue showed portions of multilayer and monolayer. The cell layers only adhered if the complementary chemistry was present on their cell surfaces. These results show that large tissues can be easily assembled via specific cell surface ligation and may provide new efficient and inexpensive bio-reactor routes to generate complex tissues and organs.[61-64]

Since the linkage between cell layers contained a photo-cleavage site, the co-culture tissue could be separated upon UV exposure. These results demonstrate that the oxime bond formation between cells can be scaled from initial liposome fusion (nanometer scale) to small clusters of cells (micrometer scale), to large tissue patches (centimeter scale). Furthermore, upon addition of induction media, the ligated tissue patches containing hMSCs could differentiate to adipocytes, fibroblasts and osteoblasts.[65-68] Because a range of cell lines may be integrated with stem cells to generate co-culture multi-layers, new stem cell plasticity studies and higher order multi-functional 3-dimensional tissues may be possible.[69-70] This strategy is general and may be used to produce complex multi-cell type structures for a range of regenerative medical applications (organs, stem cell plasticity, tissue grafts, etc.) and as a high-throughput tissue chip screening technology.

Flow cytometry was use to quantify and characterize the amount of photo-oxyamine lipid delivered to cells via liposome fusion, for subsequent photo-oxime bond formation-induced microtissue assembly (FIG. 7). The photo-oxyamine was designed to have 3 components that are useful for spatial and temporal control of cell interconnectivity (FIG. 7A). A lipid lipophilic component to insert into membranes, a photo-cleavable center and a bio-orthogonal oxyamine group for cell surface ligation of a range of ligands or other cells presenting ketone groups.

Liposomes containing the photo-oxyamine lipid were synthesized and then delivered to fibroblasts in culture. To measure the amount of photo-oxyamine incorporated, the cells chemoselectively reacted via oxime formation with a fluorescent calcein dye containing a ketone group. FACS analysis determined the amount of photo-oxyamine molecule present at the cell surface after various time points after liposome fusion (FIG. 7B-E). As expected, the cells initially had the highest amounts of photo-oxyamine molecule, which gradually decreased over time as the cells grew and divided. This decrease is due to multiple cell divisions and therefore dilution of the photo-oxyamine lipid molecule over subsequent generations of cells. Depending on the cell line, this dilution took weeks and many rounds of cell divisions. After dilution, the cell lines were indistinguishable from untreated cells and could again be used in normal cell culture or for future liposome fusion enhancement or new cell surface tailoring. These results and observations are analogous to classical cDNA transient transfections but in this case with photo-active bio-orthogonal lipids being the transfected biomolecule. Furthermore, FACS analysis was able to quantitate the amount of lipid at different time points and showed the amount of lipid can be controlled by adjusting the liposome fusion conditions (duration, concentration) and allows for multiple fusions of different lipid like molecules (for. eg. different bio-orthogonal lipids for hydrazone, Huisgen, Diels-Alder, thiol-ene type conjugations or lipids with fluorescent, spin label, radiolabel etc. properties) or serial fusions at different time points.

As further characterization of cell surface presenting photo-oxyamine groups, a novel mass spectrometry method was developed (FIG. 7F). Lipid transfected cells were added to SAM surfaces presenting aldehyde groups, which allow cells to attach to the surface via the interfacial oxime bond formation. Cells were then removed from the surface with agitation through a stream of PBS solution and $H_2O$. Due to the covalent nature of the interfacial oxime bond between the cells and SAM surface, the lipid was essentially pulled out of the membrane and remained conjugated to the substrate. Because the substrate is conductive, MALDI mass spectrometry could be performed directly on the substrate to characterize the interfacial reaction. FIG. 7G shows MALDI analysis and clearly shows the presence of the oxime molecule on the substrate. This strategy may be used to characterize a range of lipid presenting molecules on cell surfaces and as a new pull-down method of proteins if the lipid molecule spans the plasma membrane and covalently associates with cytoplasmic proteins.

To demonstrate the spatial and temporal control of tissue assembly using the intercellular photo-oxime strategy, multilayers of adipogenc and hMSC cells were generated (FIG. 8). A dodecanone liposome was first added to hMSCs, which readily presented the ketone from the cell surface. Addition of adipogenic cells presenting photo-oxyamine to the hMSCs rapidly generated multilayers. In comparison, no multi-layers are formed without the complementary chemistry presented from either cell type. FIG. 4A-C shows images and confocal representations of the multilayers. Upon UV illumination through a mask, the adipogenic cells were released from the hMSCs due to the cleavage of the intercellular photo-oxime ligation tether.

In order to extend this strategy for potential stem cell plasticity and tissue engineering applications, multilayers were generated through the photo-oxime ligation between hMSCs and fibroblasts (FIG. 8D-I). After incubating in stem cell induction media, the hMSCs differentiated to adipocytes and subsequent UV illumination and media exchange resulted in the release of the fibroblasts generating relatively pure adipogenic cells. It should be noted that the liposome fusion method is general and can be introduced to many cell lines.

Example 12: Engineering Bacteria Cell Surfaces with Bio-Orthogonal Groups Using Liposome Fusion (a) Liposome Preparation.

Liposomes were prepared with DPPC,DMPG and the corresponding bio-orthogonal pair in 15:1:4 ratios. 160 ul of DPPC 10 mg/ml stock, 10 ul DMPG 10 mg/ml and 55 ul of 10/mg ketone/oxyamine were mixed in chloroform. After thorough evaporation of the organic solvent, content was re-suspended in a buffer of choice and sonicated for 4 h using tip-sonicator (b) Functionalized Fluorescent Assay.

Bacteria E. coli Bcl2 were grown to $OD^{650}=0.6$, corresponding to approximately $4 \times 10^8$ CFU/mL. The cells were harvested by centrifugation at 6000 rpm for 10 min, washed with 100 mM $CaCl_2$ and resuspended in 6 ml of 100 mM $CaCl_2$ for 2 h at 4° C. Aliquot cells were suspended in 10 mL of 0.5 mMol HEPES buffer pH 4.3. Cells were then treated with 6 ul EDTA 50 mM pH 8.4 and incubated at 37° C. for 1 h. Liposome fusion was attempted by addition of various concentrations of Ketone-SUV (5%, 10% and 15%) to the competent cells at 37° C. for 1 h. Aliquot samples were withdrawn and washed with PBS buffer pH 7.0. 5 ul of 1.6 mMol FITC-PEG-oxyamine was added to the suspension for 5 min at 4° C. Unbound probe was washed thoroughly three times with PBS buffer to reduce non-specific binding to cells. The extent of fusion was assessed by measuring fluorescence signal using a Nikon camera fluorescent microscopy at $\Delta$ex 492 nm and $\Delta$em 518 nm along with Beckman Coulter Flow Cytometer at $\Delta$ex 600 nm for FITC based probe. Control experiment was conducted parallel to other trials, with addition of plain liposomes deficient of bio-orthogonal pairs.

(c) Profile Biotin/Streptavidin Analysis.

Bacteria E. coli Bcl2 were grown to $OD^{650}=0.6$, corresponding to approximately $4 \times 10^8$ CFU/mL. The cells were harvested by centrifugation at 6000 rpm for 10 min, washed with 100 mM $CaCl_2$ and resuspended in 6 ml of 100 mM $CaCl_2$ for 2 h at 4° C. Aliquot cells were suspended in 10 mL of 0.5 mMol HEPES buffer pH 4.3. Cells were then treated with 6 ul EDTA 50 mM pH 8.4 and incubated at 37° C. for 1 h. Liposome fusion was attempted by addition of various concentrations of Ketone-SUV (5%, 10% and 15%) to the competent cells at 37° C. for 1 h. Aliquot samples were withdrawn and washed with PBS buffer pH 7.0. Series of different volume 20, 40, 60, 80, 100, 120 uL of Biotin-PEG-oxtamine 50 mg/mL were added to the suspension and incubated for 3 h min at 4° C. Unbound biotin was washed thoroughly three times with PBS buffer to reduce non-specific binding to cells. Conjugated cells were then treated with 50 uL of Streptavidin-FITC for 30 min at 37° C. The extent of fusion was assessed by measuring fluorescence signal using a Beckman Coulter Flow Cytometer at $\Delta$ex 600 nm and for FITC based probe. Control experiment was conducted parallel to other trials, with addition of plain liposomes deficient of bio-orthogonal pairs.

(d) Surface Adhesion Analysis.

Bacteria E. coli Bcl2, were grown to $OD^{650}=0.6$, corresponding to approximately $4 \times 10^8$ CFU/mL. The cells were harvested by centrifugation at 6000 rpm for 10 min, washed with 100 mM $CaCl_2$ and resuspended in 6 ml of 100 mM $CaCl_2$ for 2 h at 4° C. Aliquot cells were suspended in 10 mL of 0.5 mMol HEPES buffer pH 4.3. Cells were then treated with 6 ul EDTA 50 mM pH 8.4 and incubated at 37° C. for 1 h. Liposome fusion was done by addition of oxyamine-SUV 5% or ketone-SUV 5% to the competent cells. Aliquot samples were withdrawn and washed with PBS buffer pH 7.0. Indium tinoxide plates coated with aldehyde functionality were submerged in 10 ml of cell suspension for 4 h. Plates were removed and washed thoroughly with PBS buffer and gram stained for phase contrast microscopic analysis. Surface adhesion experiment was replicated with ArrayIt® Premium Superaldehyde and Streptavidin/Avidin substrate.

Results and Discussion

Figure 17:
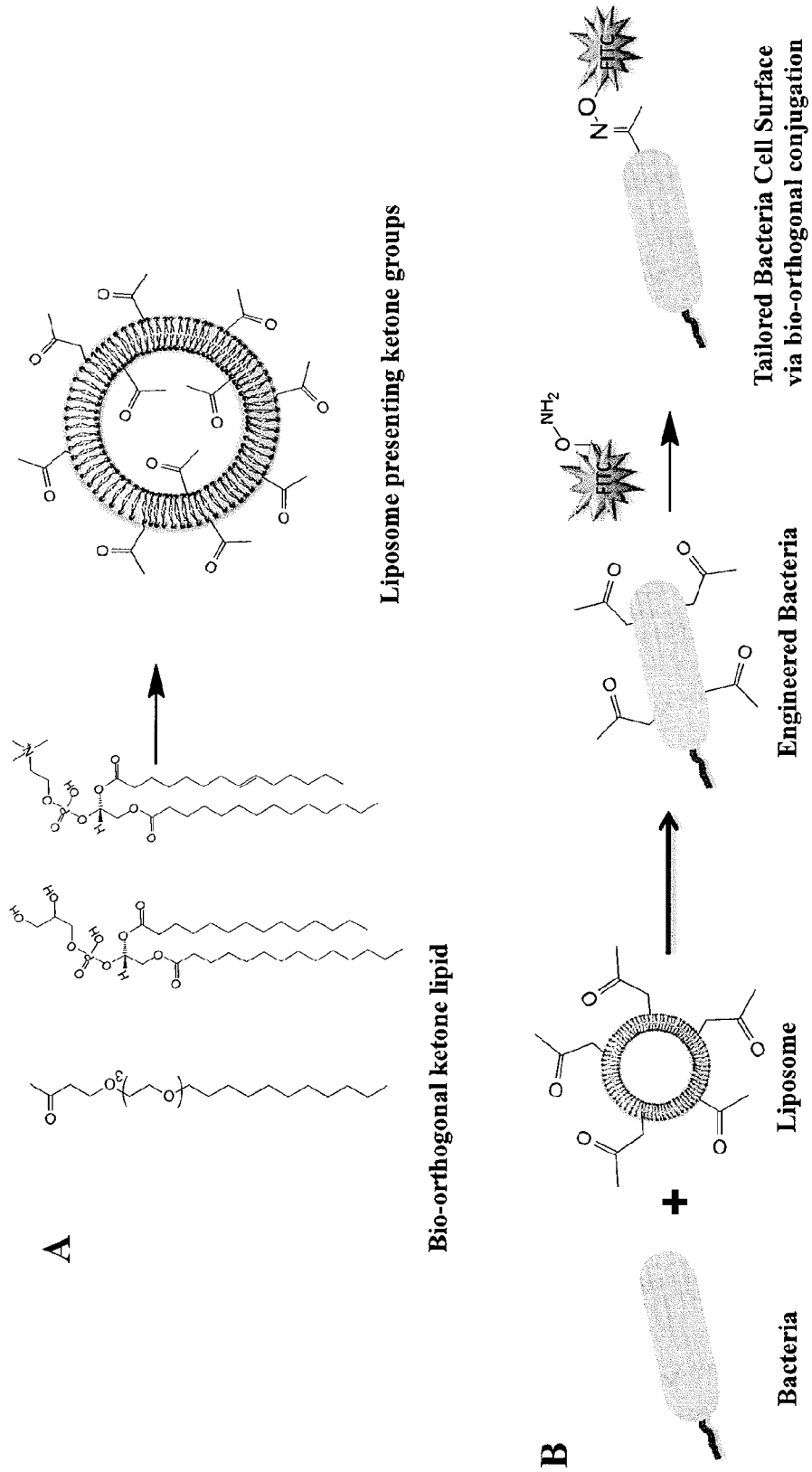
FIGS. 17A and 17B show general schemes for generating liposomes presenting ketone groups and then subsequent delivery and incorporation of the ketones in bacteria membranes via liposome fusion in accordance with an exemplary embodiment of the present application.

In this example liposomes were generated with bio-orthogonal lipids and were fused to gram negative bacteria cell surfaces, thereby delivering the bio-orthogonal lipid to the cell surface (see FIG. 17). FIG. 17A is a general scheme depicting liposome preparation for redecorating the surface of the cell. The ketone terminated lipid-like molecule (Ia) was mixed with 1,2-dipalmitoyl-sn-glycero-3-phosphocholine (DPPC) and anionic 1,2-dimyristoyl-sn-glycero-3-phospho-(1'-rac-glycerol) (DMPG) to form liposomes containing the ketone functional group. FIG. 17B shows how bacteria cells were incubated with the prepared liposome containing ketone molecules in buffer at 4.5 pH, 37° C. for 1 h. The liposomes adhered and fused to the bacteria delivering the bio-orthogonal lipid ketone molecule to the cell surface.

Figure 18:
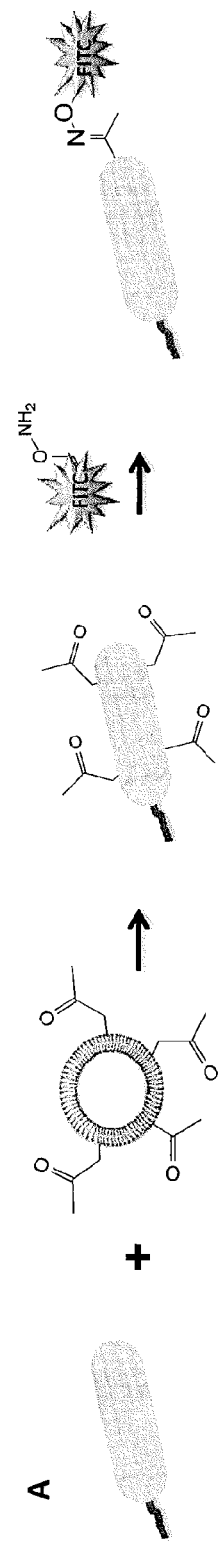
FIG. 18A shows a general scheme to conjugate fluorescent ligands to the engineered ketone-presenting bacterial cells via bio-orthogonal chemistry in an exemplary embodiment of the present application.
FIGS. 18B-D show the results of the characterization of these cells with flow cytometry.
Figure 18:
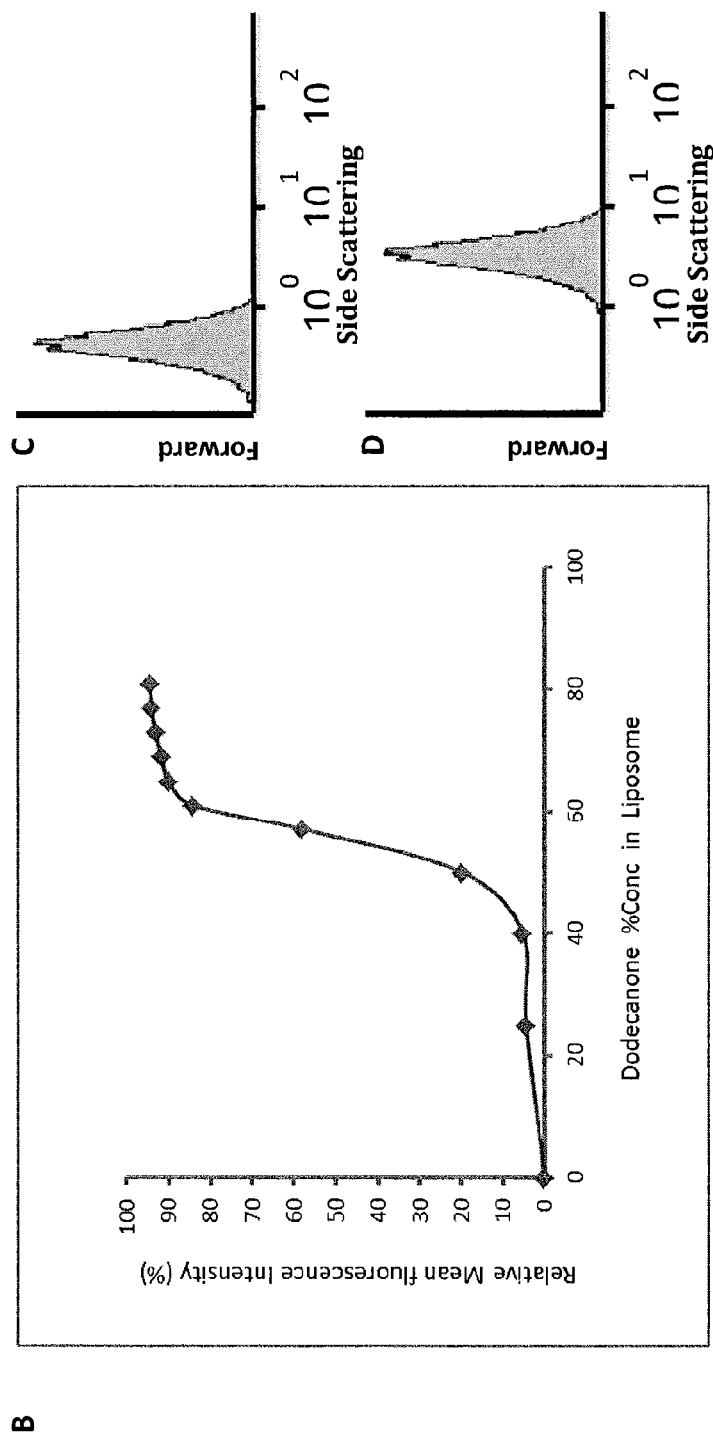

The engineered cell surface of the bacteria presenting bio-orthogonal groups underwent subsequent reaction with a range of molecules, ligands, proteins and probes. For example, as shown in FIG. 18A, ketone presenting bacteria were reacted with the fluorescent dye (FITC) oxyamine to generate oxime conjugated fluorescent bacteria. FIG. 18B shows the flow cytometry characterization of the relationship between ketone incorporated into the cell surface versus ketone concentration in the liposome. From the plot it is clear that the increase in ketone concentration in the liposome results in an increase in ketone on the cell surface. FIG. 18C shows the flow cytogram for cells treated with liposomes not containing ketone and then fluorescent dye FITC-$ONH_2$. Since no oxime reaction was possible at the cell surface, these cells showed no fluorescence. The flow cytogram of cells treated with liposomes containing ketone and then conjugated with the fluorescent dye FITC-$ONH_2$ is shown in FIG. 18D where fluorescence was seen. Flow cytometry was also used assess the number of ketone molecules on a bacteria cell surface as a function of incubation time and the amount of ketone in the liposome. The number of ketone molecules on the cell surface was determined by exposing the cells to FITC-$ONH_2$ and then using flow cytometry to measure the fluorescence intensity relative to known fluorescent bead standards. Results showed that the number of fluorescent molecules on the surface were directly proportional to the ketone content in the liposome. Increasing the ketone content in the liposome and incubation time (liposome fusion time) resulted in increasing the ketone amount on the cell surface.

Figure 19:
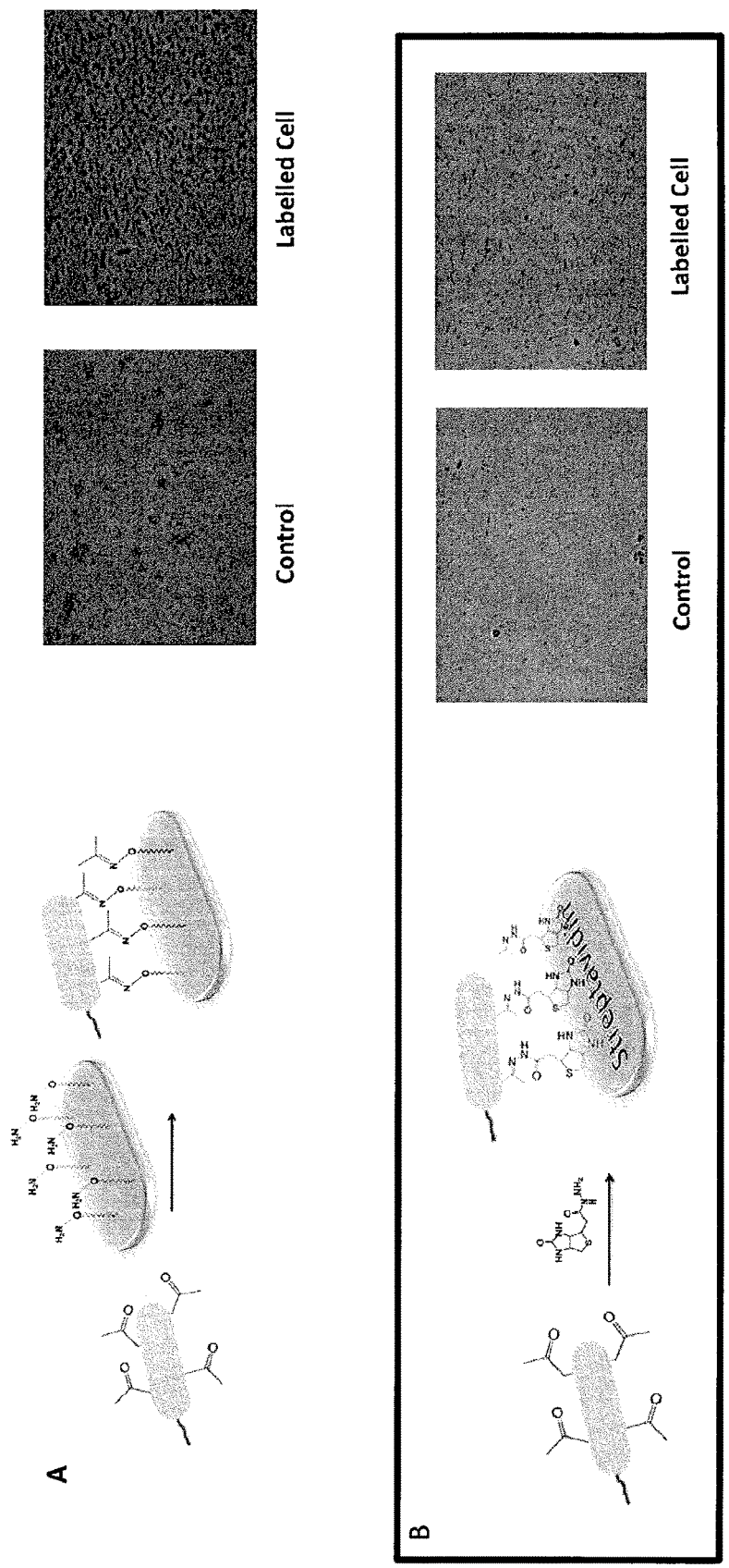
FIG. 19A shows a general schematic of engineered ketone-presenting bacterial cells conjugating to materials presenting oxyamine groups, along with microscopic analysis of resulting materials along with controls in an exemplary embodiment of the present application.
FIG. 19B shows a general schematic of engineered ketone presenting bacterial cells reacted with biotin to generate biotin presenting bacteria followed by immobilization on streptavidin coated materials in an exemplary embodiment of the present application. Also shown is the microscopic analysis of the resulting materials along with controls.

Bacteria presenting ketones were added to materials (substrates) presenting oxyamine groups. The Bacteria with ketones immobilized to the substrates presenting oxyamines via the oxime ligation method. FIG. 19A shows Indium Tin Oxide materials presenting oxyamine groups. When either the ketone group or oxyamine group was not present on the surface of the cell or the material, no cell adhesion occurred. Ketone presenting cells were also reacted with the small molecule biotin to generate biotin presenting bacteria. These bacteria then immobilized specifically to streptavidin coated materials (FIG. 19B). It is well known that the small molecule biotin binds tightly to its partner protein streptavidin. Bacteria cells did not adhere to streptavidin coated materials when no biotin was present on the bacteria cell surface (control).

Figure 20:
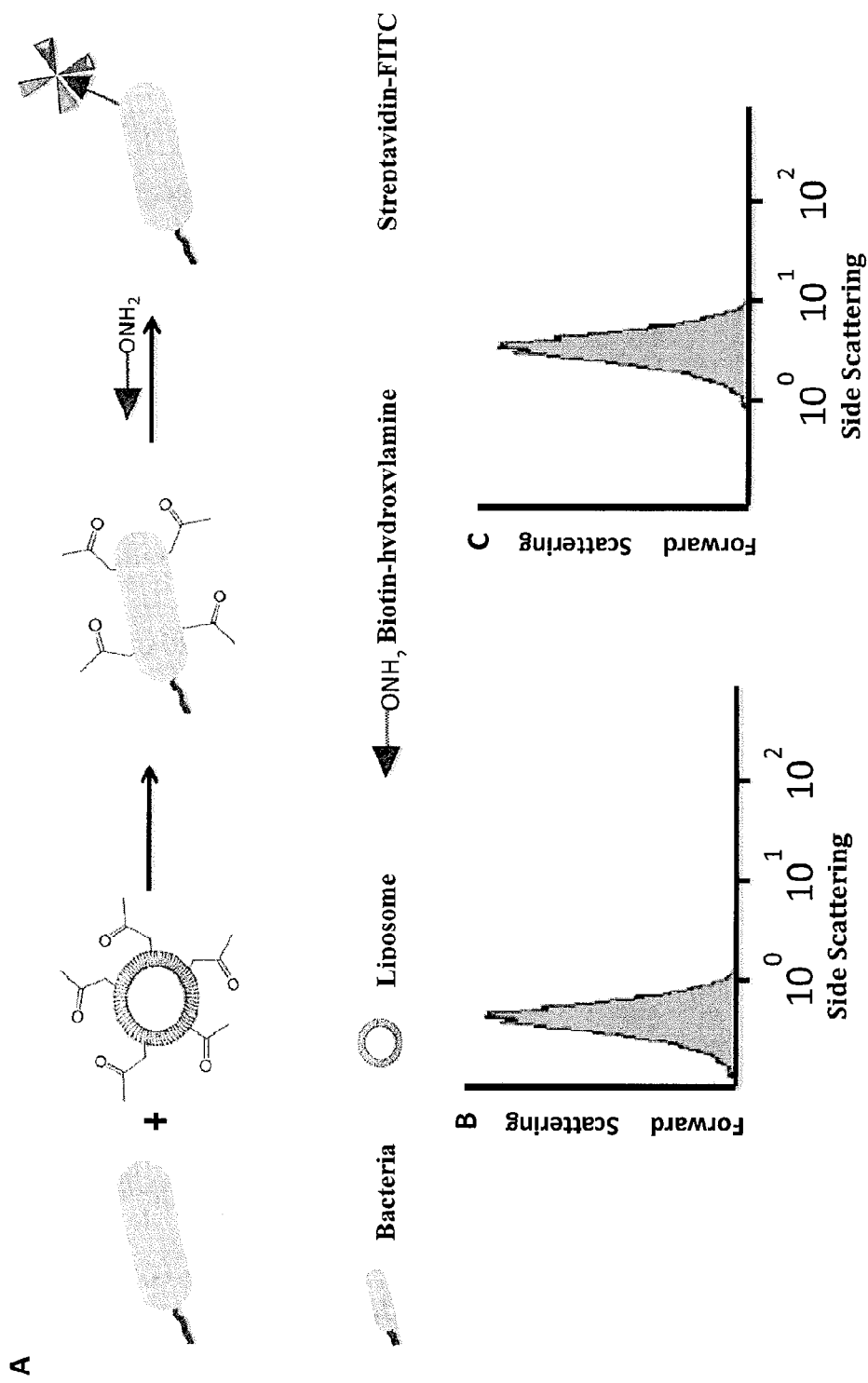
FIG. 20A shows a general schematic of the preparation of biotin-presenting bacteria and subsequent conjugation to streptavidin that was conjugated to a fluorescent dye in an exemplary embodiment of the present application.
FIGS. 20B and 20C show the flow cytometry characterization of the resulting cells.

The biotin ligand was presented on the bacteria cell surface via oxime conjugation and streptavidin was added to the cells and specifically bound to the biotin presenting bacteria (FIG. 20A). Streptavidin was conjugated with a fluorescent dye and the amount of fluorescence was determined via flow cytometry for cells presenting no biotin (FIG. 20B) and for cells presenting biotin (FIG. 20C). The data clearly show that only cells presenting the biotin ligand are fluorescent.

This allows for the modification of the bacteria cell surface with new types of molecules which is important for fundamental studies of bacteria behavior and may be used to generate vaccines and as probes for bacteria imaging and as methods to study pathogenicity. Western blot and mass spectrometry analysis of engineered bacteria cells presenting streptavidin bound to the biotin ligand was also performed. Western blot and mass spectrometry analyses of cell lysates showed the presence of peptides derived from streptavidin on the biotin presenting engineered cells.

Example 13: Dual Nucleic Acid Transfection and Cell Surface Engineering (a) Methods and Materials O-Dodecyloxyamine was synthesized as reported in U.S. Patent Application Publication No. US 2013/0302891. 1-palmitoyl-2-oleoyl-sn-glycero-3-phosphocholine (POPC) and 1,2-dioleoyl-3-trimethylammonium-propane (DOTAP) were purchased from Avanti Polar Lipids (Alabaster, Ala.), and all other chemicals were obtained from Sigma-Aldrich or Fisher. 3T3 Swiss Abino Fibroblasts were purchased from ATCC. RFP Expressing Human Neonatal Dermal Fibroblasts (RFP-HNDFs) were purchased from Olaf Pharmaceuticals. NIH3T3/GFP cell line was purchased from Cell Biolabs, Inc. These cell lines were transferred by Cedarlanelabs (Burlington, Canada). C3H/10T1/2 cell line was from McDermott group at York University. DNase-free, RNase-free and protease-free water and siRNA buffer were purchased from fisher. Monster Green phMGFP Vector was purchased from Promega. Corresponding siRNA was designed and synthesized from Life Technologies.

Liposomes were prepared as described in as reported in U.S. Patent Application Publication No. US 2013/0302891 3T3 Swiss Abino Fibroblasts were purchased from ATCC. RFP Expressing Human Neonatal Dermal Fibroblasts (RFP-HNDFs) were purchased from Olaf Pharmaceuticals. NIH3T3/GFP cell line is purchased from Cell Biolabs, Inc. These cell lines were transferred by Cedarlanelabs (Burlington, Canada). C3H/10T1/2 cell line was available from McDermott group at York University, Toronto, Canada. DNase-free, RNase-free and protease-free water and siRNA buffer were purchased from Fisher. Monster Green phMGFP Vector was purchased from Promega. Corresponding siRNA was designed and synthesized by Life Technologies.

(b) Preparation of Functionalized Liposomes

Liposomes were prepared as described in Example 2. To generate functionalized liposomes presenting oxyamine or ketone, O-dodecyloxyamine or 2-dodecanone (60 µL, 10 mM solution in $CHCl_3$) were mixed with POPC (220 µL, 10 mg/mL in $CHCl_3$) and DOTAP (220 µL, 10 mg/mL in $CHCl_3$), followed by thoroughly drying with $N_2$. The dried lipid samples were then suspended in 3 mL PBS buffer (pH 7.4) and sonicated with a tip sonicator (fisher scientific) for 15 min to form a clear liposome suspension (1.5 mg/mL).

(c) Preparation of Functionalized Liposome-DNA Complex

Functionalized liposomes from (b) (5 µL, 1.5 mg/mL) and phMGFP Vector (5 µL, 10 µg/mL) were mixed for 30 min at room temperature to form liposome-DNA complex, which was then added to DMEM media containing 10% FBS to reach a final volume of 100 µL (75 µg/mL liposome, 0.5 µg/mL GFP-DNA)

(d) Simultaneously Transfect and Engineer Cell (STEC): Simultaneous Cell Transfection and Cell Surface Engineering with Functionalized Liposome-DNA Complex To a 96-well microplate, 100 µL liposome-DNA complex media was added when cells reach 70% confluency. Cells were maintained in liposome-DNA complex media for up to 36 hours before changing media to regular media.

(e) Preparation of Functionalized Liposome-siRNA Complex

Functionalized liposomes from (b) (0.5 µL, 1.5 mg/mL) and siRNA (5'-CCGUGUUCGACUACGGUAATT-3', 5'-UUACCGUAGUCGAACACGGTT-3') (0.5 µL, 20 µM) were mixed for 30 min at room temperature to form liposome-siRNA complex, which was then added to DMEM media containing 10% FBS to reach a final volume of 100 µL (7.5 µg/mL liposome, 100 nM siRNA).

(f) Simultaneously Transfect and Engineer Cell (STEC): Simultaneous Cell Transfection and Cell Surface Engineering with Functionalized Liposome-siRNA Complex After 3T3 Swiss Abino Fibroblasts were successfully transfected with phMGFP vector, 100 µL corresponding liposome-siRNA complex was added to each well of 96-well microplate for up to 2 days.

(g) Cell Culture

3T3 Swiss Abino Fibroblasts, RFP Expressing Human Neonatal Dermal Fibroblasts, and C3H/10T1/2 cells were cultured in Dulbecco's modified Eagle medium (DMEM) with 10% fetal bovine serum (FBS) and 1% penicillin/streptomycin. NIH3T3/GFP cells were cultured in DMEM containing 10% FBS, 0.1 mM MEM Non-Essential Amino Acids, 2 mM L-glutamine, 10 µg/mL Blasticidin, and 1% penicillin/streptomycin. These cells were incubated at 37° C. in a humidified atmosphere of 5% $CO_2$, and released from tissue culture plates using 0.05% trypsin in 0.53 mM EDTA.

(h) Confocal Microscopy

The cell samples for confocal microscopy were fixed with formaldehyde (3.2% in PBS) for 20 min, rinsed with PBS, and then secured in fluorescence mounting medium (Dako, Carpinteria, Calif., USA), which enhances the visualization of cells when viewed under a fluorescent microscope, with a thin glass cover slip. The mounted samples were imaged by Zeiss LSM 700 laser scanning confocal microscope and analyzed by ZEN 2010 imaging software.

(i) Discussion

Figure 21:
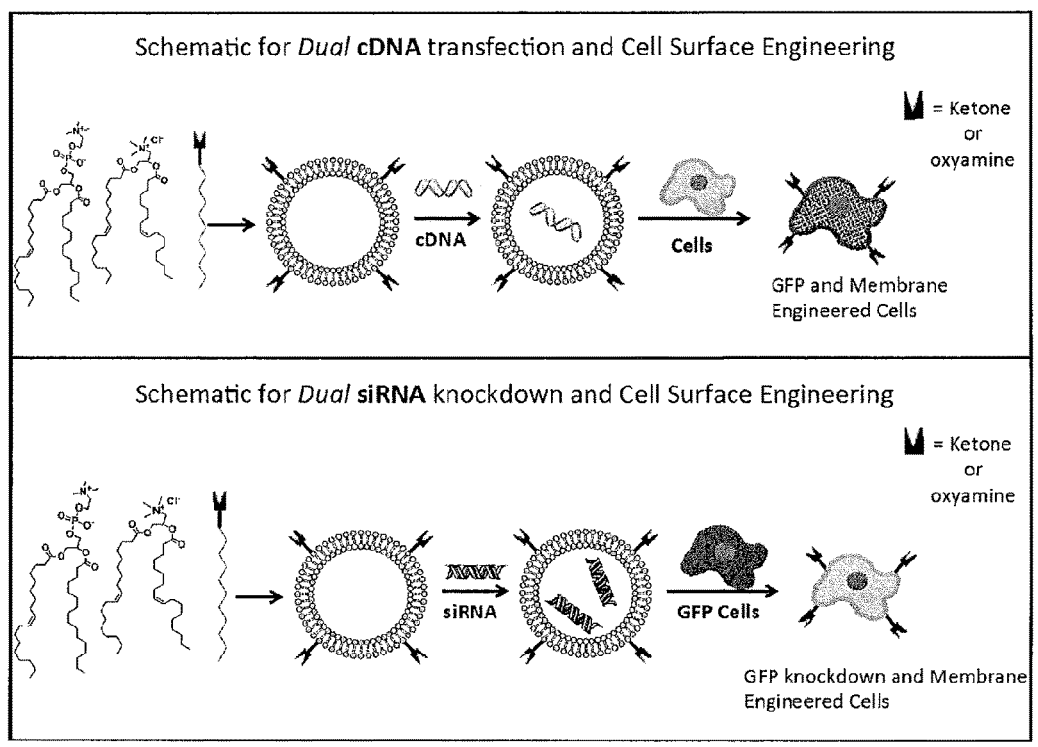
FIG. 21 shows a general schematic of the dual nucleic acid transfection and cell surface engineering method in an embodiment of the present application.

A schematic showing the dual nucleic acid transfection and cell surface engineering method of the present application is provided in FIG. 21. First, liposomes comprising a bio-orthogonal functional group, such as ketone, aldehyde, amine or oxyamine groups are prepared. Second, nucleic acids are added and a complex is formed with the liposomes. Third, the nucleic acid liposome complex is then delivered to mammalian cells to simultaneously transfect the cells and label the plasma membrane with the bio-orthogonal functional groups. The transfected and cell-surface engineered cells can then undergo further modification due to the new bio-orthogonal functional groups on the cell's surface for a range of applications.

Figure 23:
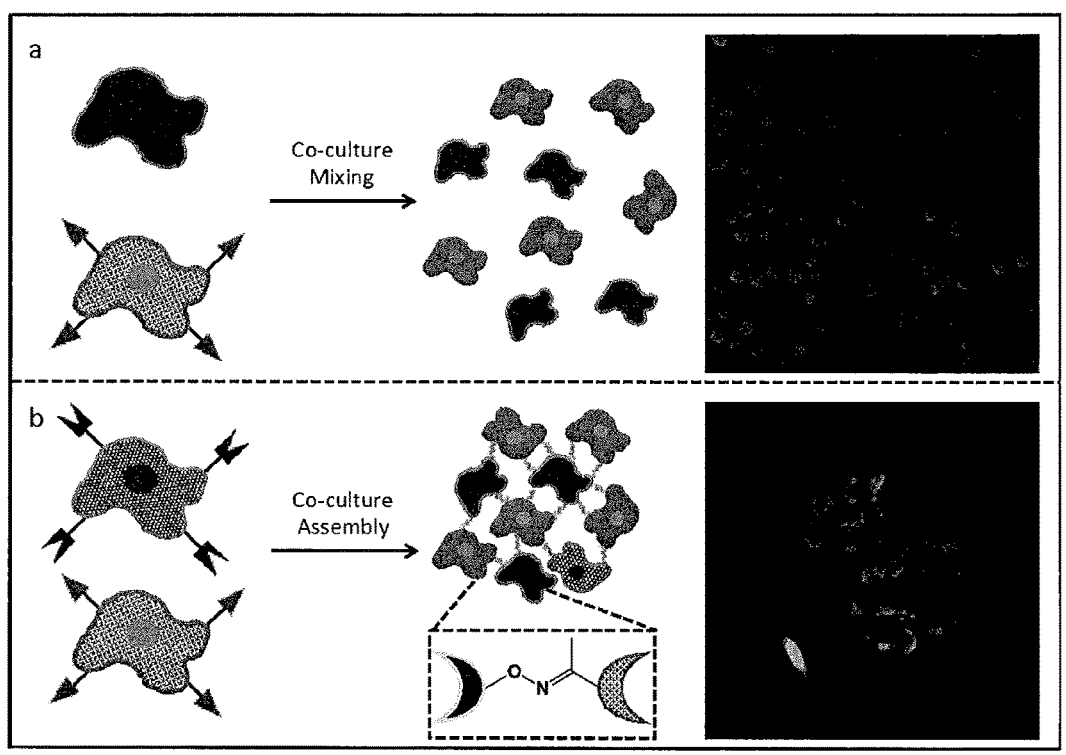
FIGS. 23a and 23b show a general schematic and images of cells transfected with bio-orthogonal groups resulting in cell-cell assemblies. In (a), controls are depicted showing that transfected Red Fluorescent Protein (RFP) and GFP cells do not form cell-cell assemblies due to only the GFP cells having bio-orthogonal groups on their surface. In (b) cell-cell assemblies, formed via bio-orthogonal conjugation between RFP and GFP cells when each has one of the bio-orthogonal pair, are depicted.

The method has been successfully applied using functionalized liposomes presenting oxyamine and ketone groups from O-dodecyloxyamine and 2-dodecanone. Specifically, Swiss 3T3 Albino fibroblasts were transfected with Green Fluorescent Protein (GFP) resulting in fluorescent cells (FIG. 22a) and GFP expressing fibroblasts lost their fluorescence upon transfection with GFP siRNA (FIG. 22b). Further examples included the transfection of 10T1/2 embryonic stem cells with GFP and transfection of red fluorescent protein (RFP)-expressing epidermal fibroblasts with GFP. As time increased, the RFP cells became increasingly green due to the GFP transfection and expression. Cell-cell assemblies were formed via bio-orthogonal conjugation between RFP and GFP cells when each had one of the bio-orthogonal pair on its surface (FIG. 23b). In a control, transfected GFP and RFP cells did not form cell-cell assemblies when only the GFP cells had a bio-orthogonal group on its cell surface.

Example 14: Dialdehyde Conjugation Method

The synthesis of the compounds of the dialdehyde lipid-like molecules of Formula IV is shown in Scheme 2.

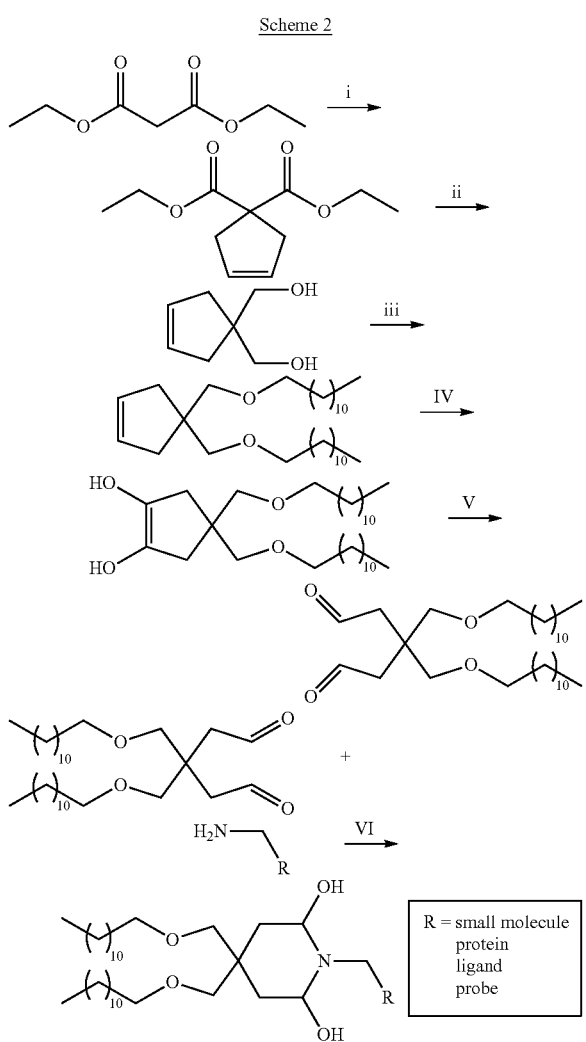

Scheme 2

The reagents and conditions used in the preparation, along with the percent yield of the product, are as follows: (i) cis-1,4-Dichloro-2-butene (1.0 eq), Na (2.2 eq), t-butanol 12 h, 80%. (ii) LiAlH₄ (5.0 eq), −78° C., Dry THF, 2 h, NaOH/H₂O 1M, 3 h, 95%. (iii) 1-bromododecane (3 eq), NaH (excess), Dry THF, Ar, 24 h, 80%. (IV) OsO₄, N-methylmorpholine N-oxide (excess), acetonitrile:acetone:H₂O, 12 h, 90%. (V) NaIO₄, acetone:H₂O, 5 h, 40%. (VI) 1 (eq) of amine-ligand in H₂O (20 min) results in rapid and stable conjugation 95%.

Figure 24:
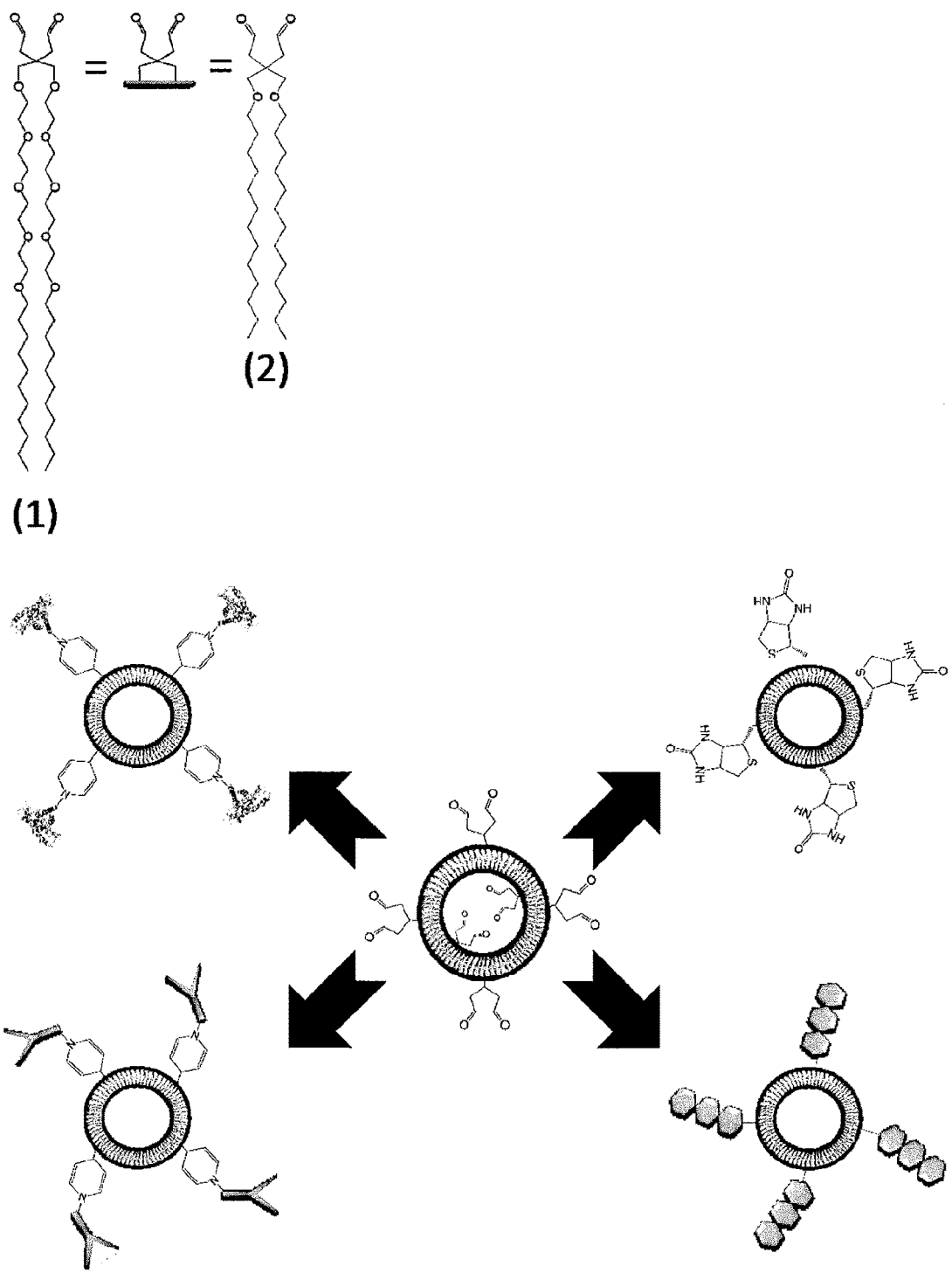
FIG. 24 is a general schematic of the dialdehyde conjugation strategy in accordance with one embodiment of the present application.

FIG. 24 shows schematically how the dialdehyde reacts with primary amine containing small molecules, ligands, probes, proteins, etc., to generate a stable covalent six member ring conjugate that can be delivered to cell surfaces via liposome fusion. The dialdehyde can be used in either the ethylene glycol (1) or alky-chain (2) forms for liposome formation.

Figure 25:
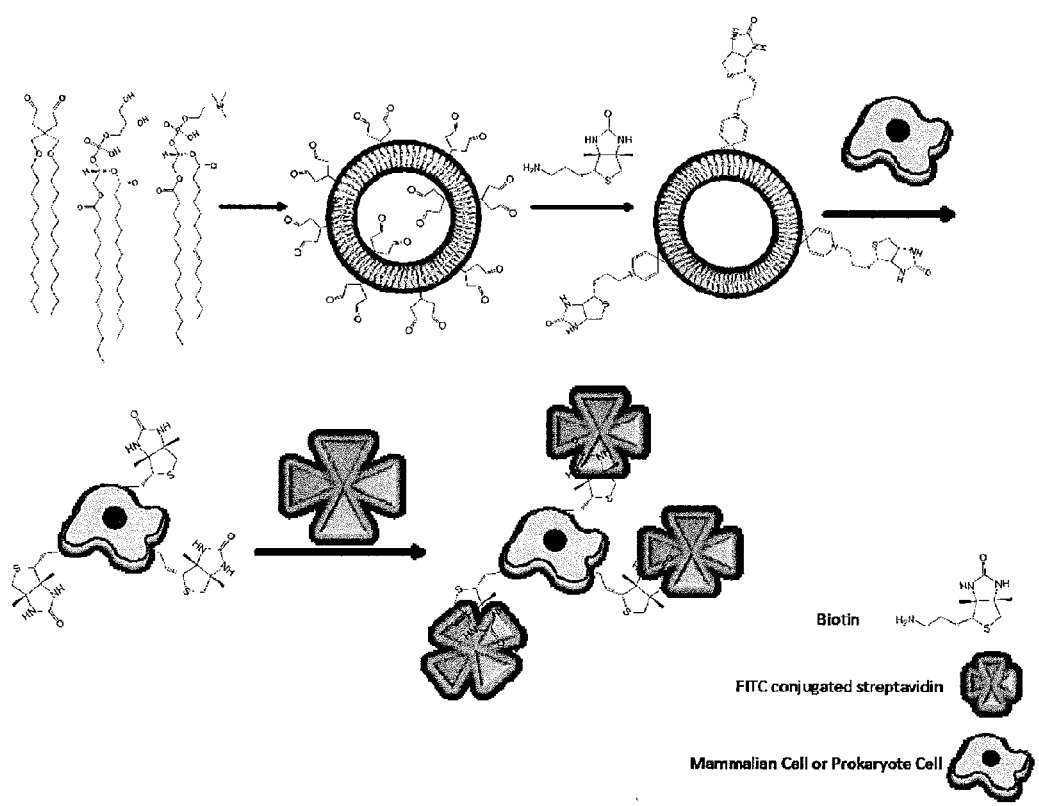
FIG. 25 show a schematic of dialdehyde (compound of Formula V) liposome formation followed by ligand conjugation in an exemplary embodiment of the present application. The liposome conjugate was added to cells to deliver the biotin ligand to the cell surface. A fluorescently tagged streptavidin protein was then added and binds specifically to the biotin presenting cell.
Figure 26:
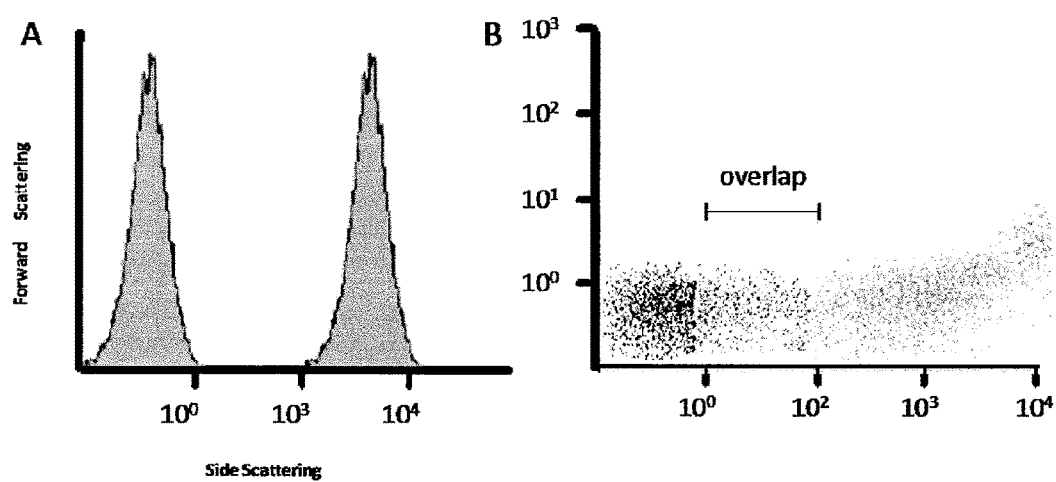
FIGS. 26A and 26B present flow cytometry data showing biotin delivered to fibroblast cells via the dialdehyde linker in an exemplary embodiment of the application. Fluorescent-streptavidin binding to Biotin presenting cells is measured by flow cytometry. (A) The left histogram shows the control where no biotin is added to the dialdehyde liposome followed by fusion to fibroblast cells and streptavidin exposure (no fluorescence is observed). The right histogram shows fluorescent cells due Streptavidin recognition of biotin-dialdehyde presenting cells. (B) Flow cytometry data showing the distribution between the control and biotin presenting cells.

FIG. 25 depicts the incorporation of the dialdehyde lipid like compounds of Formula V into liposomes followed by ligand conjugation. The liposome conjugate was added to cells and used to deliver the biotin ligand to the cell surface. A fluorescently tagged streptavidin protein was then added and bound specifically to the biotin presenting cell FIG. 25. Flow cytometry data confirmed that biotin was delivered to fibroblast cells via the dialdehyde linker (FIGS. 26A and 26B).

Advantages of the dialdehyde lipid-like compounds are as follows:

1. The dialdehyde in a 1.5 arrangement will react rapidly with primary amines to generate a six member ring that is covalent and stable at physiological conditions (pH 7.0, 37° C., aqueous)
2. The coupling reaction is fast at physiological conditions (half life less than 5 minutes)
3. The protein or ligand does not need to be manipulated (needs only a primary amine (e.g. lysine)) to conjugate proteins, ligands, molecules, etc.
4. When the dialdehyde is incorporated into a liposome—it can conjugate many molecules, ligands, proteins, probes etc., to the liposome.
5. Either the ethyleneglycol tail dialdehyde (Formula Va) or the long alkyl chain dialdehyde (Vb) are capable of amine conjugation.
6. Liposomes comprising the dialdehyde compounds can be delivered to cells for surface presentation of ligands, proteins, etc., in minutes. This provides transient transfection without manipulating the cell genome. Many applications are possible, ranging from immunotherapy to vaccines to cancer to fundamental studies of cell behavior.
7. The compounds represent new tool for chemists and cell biologists to conjugate a range of probes, proteins, ligands and small molecules to the surface of many cell types. For example, this dialdehyde liposome strategy has been used to conjugate both biotin and anti-flag peptide to bacteria and swiss 3T3 albino fibroblasts. Biotin was recognized by streptavidin on both bacteria and fibroblasts. Anti-flag peptide was recognized by the flag antibody to both bacteria and fibroblasts.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE SPECIFICATION

1. Nelson, C. M.; Bissel, M. J. *Annu. Rev. Cell Dev. Biol.* 2006, 22, 287-309.
2. Meshel, A. S.; Wei, Q.; Adelstein, R. S.; Sheetz, M. P. *Nat. Cell Biol.* 2005, 7, 157-164.
3. Isenberg, B. C.; Williams, C.; Tranquillo, R. T. *Annu. Biomed. Eng.*, 2006, 34, 971-985.
4. Hollister, S. J. (2005). *Nature Mater.* 4:518-524.
5. Gillette, B. M.; Jensen, J. A.; Tang, B.; Yang, G. J.; Bazargan-Lari, A.; Zhong, M.; Sia, S. K. *Nat. Mater.* 2008, 7, 636-640.
6. Tanaka, H.; Murphy, C. L.; Murphy, C.; Kimura, M.; Kawai, S.; Polak, J. M. *J. Cell Biochem.* 2004, 93, 454-462.
7. Gartner, Z. J.; Bertozzi, C. R. *Proc. Natl. Acad. Sci. U.S.A.* 2009, 106, 4606-4610.
8. Albrecht, D. R.; Underhill, G. H.; Wassermann, T. B.; Sah, R. L.; Bhatia, S. N. *Nat. Methods* 2006, 3, 369-375.
9. Gray, D. S.; Tan, J. L.; Voldman, J.; Chen, C. S. *Biosens. Bioelectron.* 2004, 19, 1765-1774.
10. Odde, D. J, Renn, M. J. *Biotechnol. Bioeng.* 2000, 67, 312-318.
11. Nahmias, Y.; Odde, D. J. *Nat. Protocol* 2006, 1, 2288-229626.
12. Barron, J. A.; Krizman, D. B.; Ringeisen, B. R. *Annu. Biomed. Eng.* 2005, 33, 121-130.
13. Inaba, R.; Khademhosseini, A.; Suzuki, H.; Fukuda, J. *Biomaterials* 2009, 30, 3573-3577.
14. Ringeisen, B. R.; Othon, C. M.; Barron, J. A.; Young, D.; Spargo, B. *J. Biotechnol.* 2006, 1, 930-948.
15. Chiou, P. Y.; Ohta, A. T.; Wu, M. C. *Nature* 2005, 436, 370-372.
16. Falconnet, D.; Csucs, G.; Grandin, H. M.; Textor, M. *Biomaterials* 2006, 27, 3044-3063.
17. Khademhosseini, A.; Langer, R.; Borenstein, J.; Vacanti, J. P. *Proc. Natl. Acad. Sci. U.S.A.* 2006, 103, 2480-2487.
18. Luo, W.; Chan, E. W. L.; Yousaf, M. N. *J. Am. Chem. Soc.* 2010, 132, 2614-2621.
19. Mahal, L. K.; Yarema, K. J.; Bertozi, C. R. *Science* 1997, 276, 1125-1128.
20. Prescher, J. A.; Bertozzi, C. R. *Nat. Chem. Biol.* 2005, 1, 13-21.
21. Chen, I.; Howarth, M.; Lin, W.; Ting, A. Y. *Nat. Methods* 2005, 2, 99-104.
22. Keppler, A.; Pick, H.; Arrivoli, C.; Vogel, H.; Jonhsson, K. *Proc. Natl. Acad. Sci. U.S.A.* 2004, 101, 9955-9959.
23. Miller, L. W.; Sable, J.; Goelet, P.; Sheetz, M. P.; Cornish, V. W. *Angew. Chemie. Int. Ed.* 2004, 43, 1672-1675.
24. Kellam, B.; De Bank, P. A.; Shakesheff, K. M. *Chem. Soc. Rev.* 2003, 32, 327-337.
25. Rabuka, D.; Forstner, M. B.; Gravers, J. T.; Bertozzi, C. R. *J. Am. Chem. Soc.* 2008, 130, 5947-5953.
26. Mayer, A. (2002) Membrane fusion in eukaryotic cells. *Annu. Rev. Cell. Develop. Biol.* 18, 289.
27. Rowan, A. (2006) Clamping down on exocytosis. *Nat. Rev. Mol. Cell Biol.* 7, 555-561.
28. Ellens, H., Bentz, J., and Szoka, F. C. (1985) Proton- and calcium-induced fusion and destabilization of liposomes. *Biochemistry*, 24, 3099-3106.
29. Dennison, S. M., Greenfield, N., Lenard, J., and Lentz, B. R. (2002) VSV Transmembrane domain (TMD) peptide promotes PEG-mediated fusion of liposomes in a conformationally sensitive fashion. *Biochemistry*, 41, 14925-14934.
30. Evans, K. O., and Lentz, B. R. (2002) Kinetics of lipid rearrangements during poly(ethylene glycol)-mediated fusion of highly curved unilamellar vesicles. *Biochemistry*, 41, 1241-1249.

31. Jahn, R., Lang, T., and Sudhof, T. C. (2003) Membrane fusion. *Cell,* 112, 519-533.
32. McNew, J. A., Weber, T., Parlati, F., Johnston, R. J., Melia, T. J., Sollner, T. H., and Rothman, J. E. (2000) Close is not enough: Snare-dependent membrane fusion requires an active mechanism that transduces force to membrane anchors. *J. Cell Biol.* 150, 105-117,
33. Soolner, T. H. (2004) Intracellular and viral membrane fusion: An uniting mechanism. *Curr. Opin. Biol.* 16, 429-435.
34. Parlati, F., Weber, T., McNew, J. A., Westermann, B., Sollner, T. H., and Rothman, J. E. (1999) Rapid and efficient fusion of phospholipid vesicles by the α-helical core of a SNARE complex in the absence of an N-terminal regulatory domain. *Proc. Natl. Acad. Sci. U.S.A.* 96, 12565-12570.
35. Paumet, F., Rahimian, V., and Rothman, J. E. (2004) The specificity of SNARE-dependent fusion is encoded in the SNARE motif. *Proc. Natl. Acad. Sci. U.S.A.* 101, 3376-3380.
36. Richard, A., Marchi-Artzner, V., Lalloz, M-N., Brienne, M-J., Artzner, F., Gulik-Krzywicki, T., Guedeau-Boudeville, M-A., and Lehn, J.-M. (2004) Fusogenic supramolecular vesicle systems induced by metal ion binding to amphiphilic ligands. *Proc. Natl. Acad. Sci. U.S.A.* 101, 15279-15284.
37. Marchi-Artzner, V., Gulik-Krzywicki, T., Guedeau-Boudeville, M-A., Gosse, C., Sanderson, J. M., Dedieu, J.-C., and Lehn, J-M. (2001) Selective adhesion, lipid exchange and membrane-fusion processes between vesicles of different sizes bearing complementary molecular recognition groups. *ChemPhysChem* 2, 367-376.
38. Marchi-Artzner, V., Jullien, L., Gulik-Krzywicki, T., and Lehn, J.-M. (1997) Molecular recognition induced aggregation and fusion between vesicles containing lipids bearing complementary hydrogen bonding head groups. *Chem. Commun.* 1, 117-118.
39. Paleos, C. M., and Tsiourvas, D. (2006) Interaction between complementary liposomes: A process leading to multicompartment systems formation. *J. Mol. Recognition,* 19, 60-67.
40. Chan, Y.-H. M., Lengerich, B., and Boxer, S. G. (2009) Effects of linker sequences on vesicle fusion mediated by lipid-anchored DNA oligonucleotides. *Proc. Nat. Acad. Sci. U.S.A.* 106, 979-984.
41 Gong, Y., Luo, Y., and Bong, D. (2006) Membrane activation: Selective vesicle fusion via small molecule recognition. *J. Am. Chem. Soc.* 128, 14430-14431.
42. Wilson, J. T.; Krishnamurthy, V. R.; Cui, W.; Qu, Z.; Chaikof, E. L. *J. Am. Chem. Soc.* 2009, 131, 18228-18229.
43. Csiszar, A.; Hersch, N.; Dieluweit, S.; Biehl, R.; Merkel, R.; Hoffmann, B. *Bioconjugate Chem.* 2010, 21, 537-543.
44. Pale-Grosdemange, C., Simons, E. E., Prime, K. L., and Whitesides, G. M. (1991) Formation of self-assembled monolayers by chemisorption of derivatives of oligo (ethylene glycol) of structure $HS(CH_2)_{11}(OCH_2CH_2)_m$ OH on gold *J. Am. Chem. Soc.* 113, 12-20.
45. Park, S., and Yousaf, M. N. (2008) *Langmuir,* 24, 6201-6207.
46. Csiszar, A.; Hersch, N.; Dieluweit, S.; Biehl, R.; Merkel, R., and Hoffmann, B. (2010) Novel fusogenic liposomes for fluorescent cell labeling and membrane modification. *Bioconjugate Chem.* 21, 537-543.
47. Beigel, M., Keren-Zur, M., Laster, Y., and Loyter, A. (1988) Poly(aspartic acid)-dependent fusion of liposomes bearing the quaternary ammonium detergent [[[(1,1,3,3-tetramethylbutyl)cresoxy]ethoxy]ethyl]dimethylbenzyl ammonium hydroxide. *Biochemistry* 1988, 27, 660-666.
48. Westcott, N. P., Pulsipher, A., Lamb, B. M., and Yousaf, M. N. (2008) Expedient generation of patterned surface aldehydes by microfluidic oxidation for chemoselective immobilization of ligands and cells. *Langmuir,* 24, 9237-9240.
49. Lamb, B. M., Barrett, D. G., Westcott, N. P., and Yousaf, M. N. (2008) Microfluidic lithography of SAMs on gold to create dynamic surfaces for directed cell migration and contiguous cell cocultures. *Langmuir,* 24, 8885-8889.
50. Harder, P., Grunze, M., Dahint, R., Whitesides, G. M., and Laibinis, P. E. (1998) Molecular conformation in Oligo(ethylene glycol)-terminated self-assembled monolayers on gold and silver surfaces determines their ability to resist protein adsorption. *J. Phys. Chem. B,* 102, 426-436.
51. Hsiao, S. C., Shum, B. J., Onoe, H., Douglas, E. S., Gartner, Z., Mathies, R. A., Bertozzi, C. R., and Francis, M. B. (2009) Direct cell surface modification with DNA for the capture of primary cells and the investigation of myotube formation on defined patterns. *Langmuir,* 25, 6985-6991.
52. Love, J. C.; Estroff, L. A.; Kriebel, J. K.; Nuzzo, R. G.; Whitesides, G. M. *Chem. Rev.* 2000, 105, 1103-1170.
53. Hsiao, S. C.; Shum, B. J.; Onoe, H.; Douglas, E. S.; Gartner, Z.; Mathies, R. A.; Bertozzi C. R.; Francis, M. B. *Langmuir* 2009, 25, 6985-6991.
54. Dutta, D.; Pulsipher, A.; Luo, W.; Mak, H.; Yousaf, M. N. *Bioconjugate Chemistry* 2011, 22, 2423-2433.
55. Dutta, D.; Pulsipher, A.; Luo, W.; Yousaf, M. N. *J. Amer. Chem. Soc.* 2011, 2133, 8704-8713.
56. Y. R. Zhao, Q. Zheng, K. Dakin, K. Xu, M. L. Martinez, W. H. Li, *J. Am. Chem. Soc.* 126, 4653 (2004).
57. M. Alvarez, A. Best, S. Pradhan-Kadam, K. Koynov, U. Jonas, M. Kreiter, *Adv. Mater.* 20, 4563 (2008).
58. A. M. Kloxin, A. M. Kasko, C. N. Salinas, K. S. Anseth. *Science* 324, 59 (2009).
59. A. Pulsipher, N. P. Westcott, W. Luo, M. N. Yousaf, *J. Am. Chem. Soc.* 131, 7626 (2009).
60. S. Nagrath et al., *Nature* 450, 1235 (2007).
61. K. L. Schmeichel, M. J. Bissell, *J. Cell Sci.* 116, 2377 (2003).
62 C. R. Nuttelman, S. M. Henry, K. S. Anseth, *Biomaterials* 23, 3617 (2002).
63. D. R. Albrecht, G. H. Underhill, T. B. Wassermann, R. L. Sah, S. N. Bhatia, *Nat. Methods* 3, 369 (2006).
64. R. Inaba, A. Khademhosseini, H. Suzuki, J. Fukuda, *Biomaterials* 30, 3573 (2009).
65. F. Dazzi, N. J. Horwood, *Curr. Opin. Oncol.* 19, 650 (2007).
66. M. F. Pittenger, A. M. Mackay, S. C. Beck, R. K. Jaiswal, R. Douglas, J. D. Mosca, M. A. Moorman, D. W. Simonet, S. Craig, D. R. Marshak, *Science* 284, 143 (1999).
67. R. K. Jaiswal, R. K. Jaiswal, N. Jaiswal, S. P. Bruder, G. Mbalaviele, D. R. Marshak, M. F. Pittenger, *J. Biol. Chem.* 275, 9645 (2000).
68. H. B. Fana, H. F. Liva, S. L. Toh, J. C. H. Goh, *Biomaterials* 29, 1017 (2008).
69. G. M. Keller, *Curr. Opin. Cell Biol.* 7, 862 (1995).

70. M. Schuldiner, O. Yanuka, J. Itskovitz-Eldor, D. A. Melton, N. Benvenisty, *Proc. Natl. Acad. Sci. USA* 97, 11307 (2000).
71. M. M. Stevens, J. H. George, *Science* 310, 1135 (2005).
72. T. H. Petersen, E. A. Calle, L. P. Zhao, E. J. Lee, L. Q. Gui, M. B. Raredon, K. Gavrilov, T. Yi, Z. W. Zhuang, C. Breuer, E. Herzog, L. E. Niklason, Science 329, 538 (2010).
73. V. Mironov, R. P. Visconti, V. Kasyanov, G. Forgacs, C. J. Drake, R. R. Markwald, *Biomaterials* 30, 2164 (2009).
74. D. G. Barrett, T. Merkel, C. Luft, M. N. Yousaf, *Macromolecules* 43, 9660 (2010)
75. D. G. Barrett, M. N. Yousaf, *Soft Matter,* 6, 5026 (2010)
76. D. G. Barrett, M. N. Yousaf, *Polym. Chem.,* 1, 296. (2010)
77. D. G. Barrett, M. N. Yousaf, *Biomacromolecules* 9, 2029 (2008)
78. D. G. Barrett, M. N. Yousaf, *Macromolecules* 41, 6347 (2008).
79. D. G. Barrett, M. N. Yousaf, *ChemBioChem* 9, 62 (2008).

I claim:

1. A compound of the Formula IV:

$$R-X \quad (IV)$$

wherein R is selected from:

$H_3C-(CH_2)_n-[-O-(CH_2)_m-]_p-O-(CH_2)_q-$;

$H_3C-(CH_2)_n$-Q-$[-O-(CH_2)_m]_p-O-(CH_2)_q-$; and $H_3C-(CH_2)_n-[-O-(CH_2)_m]_p-O-(CH_2)_q$-Q-;

n is 5, 6, 7, 8, 9, 10, 11, 12, 13, 14, 15, 16, 17, 18, 19, 20, 21, 22, 23, 24, 25, 26, 27, 28 or 29;
m is 1, 2, 3, or 4;
p is 1, 2, 3, 4, 5, 6, 7, 8, 9 or 10;
q is 0, 1, 2, 3, 4, 5 or 6;
Q comprises at least one of a fluorescent moiety, hydroquinone, ferrocene, a photocleavable moiety, a radioactive moiety, a chelating moiety and a spin label; and
X is selected from C(O)H, C(O)R$^1$ and O—NH$_2$ and R$^1$ is C$_{1-2}$alkyl,
provided that when R is $H_3C-(CH_2)_n-[-O-(CH_2)_m-]_p-O-(CH_2)_q-$ and X is C(O)H or C(O)R$^1$, m is 1, 3 or 4.

2. The compound of claim 1 wherein the compound is a compound of Formula I:

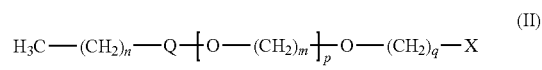

wherein:
n is 5, 6, 7, 8, 9, 10, 11, 12, 13, 14, 15, 16, 17, 18, 19, 20, 21, 22, 23, 24, 25, 26, 27, 28 or 29;
m is 1, 2, 3, or 4;
p is 1, 2, 3, 4, 5, 6, 7, 8, 9 or 10;
q is 0, 1, 2, 3, 4, 5 or 6; and
X is selected from C(O)H, C(O)R$^1$ and O—NH$_2$ and R$^1$ is C$_{1-2}$alkyl,
provided that when X is C(O)H or C(O)R$^1$, m is 1, 3 or 4.

3. The compound of claim 1 wherein the compound is a compound of Formula II:

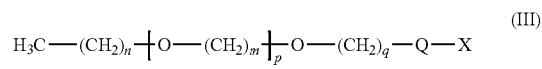

wherein:
n is 5, 6, 7, 8, 9, 10, 11, 12, 13, 14, 15, 16, 17, 18, 19, 20, 21, 22, 23, 24, 25, 26, 27, 28 or 29;
m is 1, 2, 3, or 4;
p is 1, 2, 3, 4, 5, 6, 7, 8, 9 or 10;
q is 0, 1, 2, 3, 4, 5 or 6;
Q comprises at least one of a fluorescent moiety, hydroquinone, ferrocene, a photocleavable moiety, a radioactive moiety, a chelating moiety and a spin label; and
X is selected from C(O)H, C(O)R$^1$ and O—NH$_2$ and R$^1$ is C$_{1-2}$alkyl.

4. The compound of claim 1 wherein the compound is a compound of Formula III:

$$H_3C-(CH_2)_n-[O-(CH_2)_m]_p-O-(CH_2)_q-Q-X \quad (III)$$

wherein:
n is 5, 6, 7, 8, 9, 10, 11, 12, 13, 14, 15, 16, 17, 18, 19, 20, 21, 22, 23, 24, 25, 26, 27, 28 or 29;
m is 1, 2, 3, or 4;
p is 1, 2, 3, 4, 5, 6, 7, 8, 9 or 10;
q is 0, 1, 2, 3, 4, 5 or 6;
Q comprises at least one of a fluorescent moiety, hydroquinone, ferrocene, a photocleavable moiety, a radioactive moiety, a chelating moiety and a spin label; and
X is selected from C(O)H, C(O)R$^1$ and O—NH$_2$ and R$^1$ is C$_{1-2}$alkyl.

5. The compound of claim 1 wherein the compound is selected from:

$$CH_3(CH_2)_{10}-[OCH_2CH_2]_3OCH_2CH_2ONH_2 \quad (Ic); \text{ and}$$

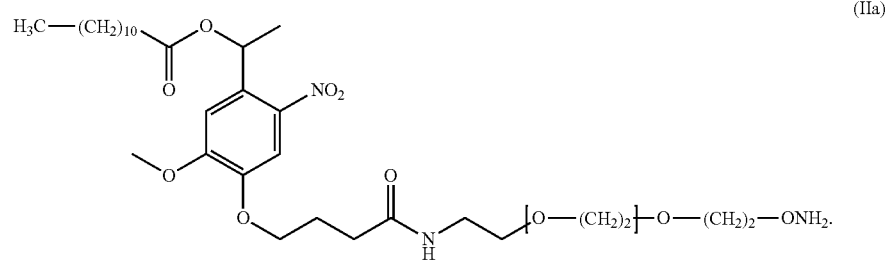

(IIa)

6. A liposome comprising one or more compounds of claim 1.

7. The liposome of claim 6, wherein the amount of the compound in the liposome is about 1 mol % to about 10 mol %.

8. The liposome of claim 6, further comprising reporter molecules and/or biologically active agents.

9. The liposome of claim 8, wherein the biologically active agent is one or more nucleic acids and the nucleic acids form a complex with the liposome.

10. A composition comprising one or more of the liposomes of claim 6 and a solvent, diluent or carrier.

11. A method of modifying a cell membrane comprising contacting the cell with a liposome comprising one of more compounds of claim 1 under conditions for incorporation of the compounds into the cell membrane.

12. A method for promoting the adhesion of cells comprising:
   (a) contacting a first cell population with a liposome of type A under conditions for the fusion of the liposome of type A with the first cell population;
   (b) contacting a second cell population with a liposome of type B under conditions for the fusion of the liposome of type B with the second cell population; and
   (c) contacting the fused first cell population with the fused second cell population,
   wherein the liposomes of type A comprise a compound of claim 1 having an X group that is complementary to an X group on a compound of claim 1 comprised in the liposomes of type B to form a chemical interaction that results in the adhesion of the first and second cell populations.

13. A method for the simultaneous transfection of one or more nucleic acid molecules into a cell and modification of the cell's membrane comprising:
   (a) combining the one or more nucleic acid molecules with a liposome under conditions to form a liposome-nucleic acid complex wherein the liposome comprises one or more amphipathic molecules; and
   (b) contacting the cell with the liposome-nucleic acid complex under conditions to simultaneously transfect the cell with the one or more nucleic acid molecules and incorporate the one or more compounds into the cell membrane,
   wherein the one or more amphipathic molecules are selected from a compound of Formula IV as defined in claim 1.

14. The compound of claim 1, wherein
n is 8, 9, 10, 11, 12, 13, 14, 15, 16, 17, 18, 19, 20, 21, 22, 23, 24, 25, 26, 27, 28 or 29;
m is 2 or 3;
p is 4, 5, 6, 7, 8, 9 or 10; and
q is 1, 2, 3 or 4.

15. The compound of claim 1, wherein the fluorescent moiety is calcein, rhodamine or fluorescein; the electroactive moiety is hydroquinone or ferrocene; and the photocleavable moiety is 4-(1-hydroxyethyl)-2-methoxy-5-nitrophenoxy.

16. A compound of the Formula V:

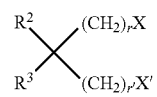

(V)

wherein $R^2$ and $R^3$ are each, independently selected from

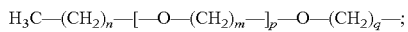

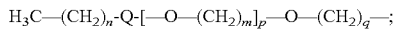

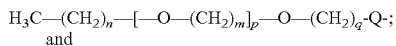
and

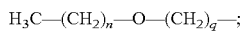

n is 5, 6, 7, 8, 9, 10, 11, 12, 13, 14, 15, 16, 17, 18, 19, 20, 21, 22, 23, 24, 25, 26, 27, 28 or 29;
m is 1, 2, 3, or 4;
p is 1, 2, 3, 4, 5, 6, 7, 8, 9 or 10;
q is 0, 1, 2, 3 or 4;
Q comprises at least one of a fluorescent moiety, hydroquinone, ferrocene, a photocleavable moiety, a radioactive moiety, a chelating moiety and a spin label;
r and r' are each independently, 1, 2 or 3; and
X and X' are each, independently, one of a complementary functional group pair.

17. The compound of claim 16, wherein $R^2$ and $R^3$ are independently selected from:

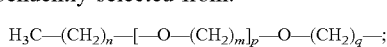
and

18. The compound of claim 17, wherein $R^2$ and $R^3$ are both $H_3C-(CH_2)_n-[-O-(CH_2)_m-]_p-O-(CH_2)_q-$.

19. The compound of claim 16, wherein
n is 8, 9, 10, 11, 12, 13, 14, 15, 16, 17, 18, 19, 20, 21 or 22;
m is 2 or 3;
p is 4, 5, 6, 7, 8, 9 or 10;
q is 1 or 2; and
r and r' are both 1 or 2.

20. The compound of claim 16, wherein
X and X' are both $C(O)R^1$, and $R^1$ is $C_{1-2}$alkyl;
X and X' are both $O-NH_2$;
X and X' are both $C(O)H$;
X and X' are both $NH_2$; or
X and X' are both $C(O)H$.

21. A liposome comprising one or more compounds of claim 16.

22. A method of modifying a cell membrane comprising contacting the cell with a liposome comprising one of more compounds of claim 16 under conditions for incorporation of the compounds into the cell membrane.

* * * * *